(12) United States Patent
Rudnicki et al.

(10) Patent No.: US 7,384,784 B2
(45) Date of Patent: Jun. 10, 2008

(54) PAX-ENCODING VECTOR AND USE THEREOF

(75) Inventors: Michael A. Rudnicki, Gloucester (CA); Patrick Seale, Brookline, MA (US)

(73) Assignee: Ottawa Health Research Institute, Ontario (CA)

( * ) Notice: Subject to any disclaimer, the term of this patent is extended or adjusted under 35 U.S.C. 154(b) by 345 days.

(21) Appl. No.: 10/835,898

(22) Filed: Apr. 30, 2004

(65) Prior Publication Data

US 2005/0042637 A1  Feb. 24, 2005

Related U.S. Application Data

(63) Continuation-in-part of application No. 10/245,171, filed on Sep. 17, 2002, now abandoned.

(60) Provisional application No. 60/322,923, filed on Sep. 17, 2001.

(51) Int. Cl.
    C12N 5/00 (2006.01)
    C12N 15/63 (2006.01)
(52) U.S. Cl. .................... 435/325; 435/320.1; 435/455
(58) Field of Classification Search ................ 435/325, 435/320.1, 455
    See application file for complete search history.

(56) References Cited

U.S. PATENT DOCUMENTS

| 5,197,985 | A | 3/1993 | Caplan et al. |
| 5,226,914 | A | 7/1993 | Caplan et al. |
| 5,328,695 | A | 7/1994 | Lucas et al. |
| 5,604,090 | A | 2/1997 | Alexander et al. |
| 5,736,396 | A | 4/1998 | Bruder et al. |
| 2003/0124102 | A1 | 7/2003 | Rudnicki et al. |
| 2005/0042637 | A1 | 2/2005 | Rudnicki et al. |

FOREIGN PATENT DOCUMENTS

CA   2 357 403   3/2003

OTHER PUBLICATIONS

Seale et al. (2000) Cell, vol. 102, 777-786.*
Schafer et al. (1994) Nuc. Acids Res. vol. 22, 4574-4582.*
Kochanek et al. (1996) Proc. Natl. Acad. Sci., vol. 93, 5731-5736.*
Bennicelli et al., "PAX3 and PAX7 Exhibit Conserved *cis*-acting Transcription Repression Domains and Utilize a Common Gain of Function Mechanism in Alveolar Rhabdomyosarcoma," *Oncogene* 18:4348-4356 (1999).
Braissant et al., "Differential Expression of Peroxisome Proliferator-Activated Receptor-α, -β and -γ During Rat Embryonic Development," *Endocrinology* 139:2748-2754 (1998).
Goulding et al., "Pax-3, A Novel Murine DNA Binding Protein Expressed During Early Neurogenesis," *The EMBO Journal* 10:1135-1147 (1991).
Gussoni et al., "Dystrophin Expression in the *mdx* Mouse Restored by Stem Cell Transplantation," *Nature* 401:390-394 (1999).
Hubank et al., "Identifying Differences in mRNA Expression by Representational Difference Analysis of cDNA," *Nucleic Acids Research* 22:5640-5648 (1994).
Jackson et al., "Hematopoietic Potential of Stem Cells Isolated From Murine Skeletal Muscle," *PNAS* 96:14482-14486 (1999).
Jostes et al., "The Murine Paired Box Gene, *Pax7*, is Expressed Specifically During the Development of the Nervous and Muscular System," *Mechanisms of Development* 33:27-38 (1991).
Kay et al., "Alternate *Pax7* Paired Box Transcripts Which Include a Trinucleotide or a Hexanucleotide are Generated by use of Alternate 3' Intronic Splice Sites which are not Utilized in the Ancestral Homologue," *Gene* 230:55-60 (1999).
Kay et al., "Association of an Unusual Form of a *Pax7*-like Gene with Increased Efficiency of Skeletal Muscle Regeneration," *Gene* 163:171-177 (1995).
Kay et al., "Pax7 Includes Two Polymorphic Homeoboxes Which Contain Rearrangements Associated with Differences in the Ability to Regenerate Damaged Skeletal Muscle in Adult Mice," *The International Journal of Biochemistry & Cell Biology* 30:261-269 (1998).
Kay et al. "Variation in the Methylation Profile and Structure of *Pax3* and *Pax7* Among Different Mouse Strains and During Expression," *Gene* 184:45-53 (1997).
Mansouri et al., "*Pax* Genes and Their Roles in Cell Differentiation and Development," *Current Opinion in the Cell Biology* 8:851-857 (1996).
Mansouri et al., "*Pax* Genes in Development," *Journal of Cell Science* 18:35-42 (1994).
Mansouri et al., "*Pax* Genes and Their Role in Organogenesis," *Cancer Research* 59:1707s-1710s (1999).
Maroto et al., "Ectopic *Pax-3* Activates *MyoD* and *Myf-5* Expression in Embryonic Mesoderm and Neural Tissue," *Cell* 89:139-148 (1997).
Megeney et al., "MyoD is Required for Myogenic Stem Cell Function in Adult Skeletal Muscle," *Gene & Development* 10:1173-1183 (1996).
Noll, "Evolution and Role of *Pax* Gene," *Current Opinion in Genetics and Development* 3:595-605 (1993).
Schäfer et al., "Molecular Cloning and Characterization of a Human PAX-7 cDNA Expressed in Normal and Neoplastic Myocytes," *Nucleic Acids Research* 22:4574-4582 (1994).
Seale et al., "The Potential of Muscle Stem Cells," *Developmental Cell* 1:1-10 (2001).
Seale et al., "Pax7 is Required for the Specification of Myogenic Satellite Cells," *Cell* 102:777-786 (2000).
Seale et al., "A New Look at the Origin, Function, and "Stem-Cell" Status of Muscle Satellite Cells," *Developmental Biology* 218:115-124 (2000).

(Continued)

*Primary Examiner*—Anne Marie S Wehbe
(74) *Attorney, Agent, or Firm*—Clark & Elbing LLP

(57) ABSTRACT

The present invention provides cells transformed with a nucleotide sequence encoding Pax7, Pax3 or both. The present invention also pertains to Pax-encoding vector that comprises a sequence encoding Pax7, Pax3 or an active variant or fragment thereof, which can be used to induce myogenic differentiation of stem cells. The present invention further pertains to methods of preparing the Pax-encoding vector. Also provided is a method of inducing myogenic differentiation in stem cells and treating a subject with the cells.

10 Claims, 31 Drawing Sheets

OTHER PUBLICATIONS

Strachan et al., "PAX Genes," *Current Opinion in Genetics and Development* 4:427-438 (1994).

Tajbakhsh et al., "Redefining the Genetic Hierarchies Controlling Skeletal Myogenesis: *Pax-3* and *Myf-5* Act Upstream of *MyoD,*" *Cell* 89:127-138 (1997).

Tajbakhsh et al., "Gene Targeting the *myf-5* Locus with *nlacZ* Reveals Expression of This Myogenic Factor in Mature Skeletal Muscle Fibres as Well as Early Embryonic Muscle," *Developmental Dynamics* 206:291-300 (1996).

Allen et al., "Hepatocyte Growth Factor Activates Quiescent Skeletal Muscle Satellite Cells In Vitro," *Journal of Cellular Physiology*. 165:307-312 (1995).

Appell et al. "Satellite Cell Activation in Human Skeletal Muscle After Training: Evidence for Muscle Fiber Neoformation," *International Journal of Sports Medicine*. 9:297-299 (1988).

Asakura et al. "Myogenic specification of side population cells in skeletal muscle," *The Journal of Cell Biology*. 159: 123-134 (2002).

Asakura et al. "The Regulation of MyoD Gene Expression: Conserved Elements Mediate Expression in Embryonic Axial Muscle," *Developmental Biology*. 171: 386-398 (1995).

Bendall et al. "Msx1 antagonizes the myogenic activity of Pax3 in migrating limb muscle precursors," *Development*. 126, 4965-4976 (1999).

Bischoff, "The Satellite Cell and Muscle Regeneration," in *Myology: Basic and Clinical*. vol. 1, Ch 3: 97-118 (1994).

Borycki et al., "Muscle determination: Another key player in myogenesis?" *Current Biology*. 7:R620-R623 (1997).

Borycki et al., "*Pax3* functions in cell survival and in *pax7* regulation," *Development*. 126: 1665-1674 (1999).

Broxmeyer et al., "Human umbilical cord blood as a potential source of transplantable hematopoietic stem/progenitor cells," *Proceedings of the National Academy of Sciences*. 86: 3828-3832 (1989).

Burt et al., "Embryonic Stem Cells As an Alternate Marrow Donor Source: Engraftment without Graft-Versus-Host-Disease," *Journal of Experimental Medicine*. 199: 895-904 (2004).

Cao et al., "Muscle stem cells differentiate into haematopoietic lineages but retain myogenic potential," *Nature Cell Biology*. 5: 640-646 (2003).

Charge and Rudnicki, "Cellular and Molecular Regulation of Muscle Regeneration," *Physiol Review*. 84:209-238 (2004).

Conway et al., "Development of a lethal congenital heart defect in the *splotch* (*PAX3*) mutant mouse," *Cadiovascular Research*. 36: 163-173 (1997).

Cornelison and Wold, "Single-Cell Analysis of Regulatory Gene Expression in Quiescent and Activated Mouse Skeletal Muscle Satellite Cells," *Developmental Biology*. 191: 270-283 (1997).

Cossu, "Activation of different myogenic pathways: myf-5 is induced by the neural tube and MyoD by the dorsal ectoderm in mouse paraxial mesoderm," *Development* 122: 429-437 (1996).

Dahl et al., "Pax genes and organogenesis," *BioEssays*. 19: 755-765 (1997).

Daston et al., "*Pax-3* is necessary for migration but not differentiation of limb muscle precursors in the mouse," *Development* 122: 1017-1027 (1996).

De Angelis et al., "Skeletal Myogenic Progenitors Originating from Embryonic Dorsal Aorta Coexpress Endothelial and Myogenic Markers and Contribute to Postnatal Muscle Growth and Regeneration," *The Journal of Cell Biology*. 147: 869-877 (1999).

Delfini et al., "Delta 1-activated Notch inhibits muscle differentiation without affecting *Myf5* and *Pax3* expression in chick limb myogenesis," *Development*. 127: 5213-5224 (2000).

Epstein et al., "Pax3 Inhibits Myogenic Differentiation of Cultured Myoblast Cells," *The Journal of Biological-Chemistry*. 270: 11719-11722 (1995).

Epstein et al., "Pax3 modulates expression of the c-Met receptor during limb muscle development," *Proceedings of the National Academy of Sciences*. 93: 4213-4218 (1996).

George-Weinstein et al., "In Vitro and in Vivo Expression of α7 Integrin and Desmin Define the Primary and Secondary Myogenic Lineages," *Developmental Biology*. 156: 209-229 (1993).

Gibson and Schultz, "Age-Related Differences in Absolute Numbers of Skeletal Muscle Satellite Cells," *Muscle and Nerve*. 6: 574-580 (1983).

Goodell et al., "Dye efflux studies suggest that hematopoietic stem cells expressing low or undetectable levels of CD34 antigen exist in multiple species," *Nature Medicine*. 3: 1337-1345 (1997).

Goodell et al., "Isolation and Functional Properties of Murine Hematopoietic Stem Cells that are Replicating In Vivo," *Journal of Experimental Medicine*. 183: 1797-1806 (1996).

Goulding et al., "Regulation of *Pax-3* expression in the dermomyotome and its role in muscle development," *Development*. 120: 957-971 (1994).

Grounds, "The Proliferation and Fusion of Myoblasts In Vivo," in *Myoblast Transfer Therapy*. (Eds. Eastwood A.B., Karpati G. and Griggs R.). Proceedings of the 1$^{st}$ International Conference on myoblast transfer trerapy held in New York City, Jun. 10-11, 1989. Plenum Press pp. 101-106 (1990).

Grounds and Yablonka-Reuveni, "Molecular and cell biology of skeletal muscle regeneration," *Molecular and Cell Biology of Muscular Dystrophy*. 210-256 (1993).

Heanue et al., "Synergistic regulation of vertebrate muscle development by Dach2, Eya2, and Six1, homologs of genes requried for Drosophila eye formation," *Genes and Development*. 13: 3231-3243 (1999).

Heslop et al., "Evidence for a myogenic stem cell that is exhausted in dystrophic muscle," *Journal of Cell Science*. 113: 2299-2308 (2000).

Holst et al., "A binding site for Pax proteins regulates expression of the gene for the neural cell adhesion molecule in the embryonic spinal cord," *Proceedings of the National Academy of Sciences*. 94: 1465-1470 (1997).

Hurko and Walsh, "Human fetal muscle-specific antigen is restricted to regenerating myofibers in diseased adult muscle," *Neurology*. 33: 737-743 (1983).

Irintchev et al., "Expression Pattern of M-Cadherin in Normal, Denervated, and Regenerating Mouse Muscles," *Developmental Dynamics*. 199: 326-337 (1994).

Jostes et al., "The murine paired box gene, *Pax7*, is expressed specifically during the development of the nervous and muscular system," *Mechanisms of Development*. 33: 27-38 (1991).

Khan et al., "cDNA microarrays detect activation of a myogenic transcription program by the PAX3-FKHR fusion oncogene," *Proceedings of the National Academy of Sciences*. 96: 13264-13269 (1999).

Leenen et al., "Markers of mouse macrophage development detected by monoclonal antibodies," *Journal of Immunological Methods*. 174: 5-19 (1994).

Mansouri et al., "Follicular cells of the thyroid gland require *Pax8* gene function," *Nature Genetics*. 19: 87-90 (1998).

Mauro, "Satellite Cell of Skeletal Muscle Fibers," *Journal of Biophysical and Biochemical Cytology*. 9: 493-495 (1961).

McKinney-Freeman et al., "Muscle-derived hematopoietic stem cells are hematopoietic in origin," *Proceedings of the National Academy of Sciences*. 99: 1341-1346 (2002).

Montarras et al., "Cultured *myf5* null and *myoD* null muscle precursor cells display distinct growth defects," *Biology of the Cell*. 92: 565-572 (2002).

Morlet et al., "Muscle precursor replication after repeated regeneration of skeletal muscle in mice," *Anatomy and Embryology*. 180: 471-478 (1989).

Münsterberg and Lassar, "Combinatorial signals from the neural tube, floor plate and notochord induce myogenic bHLH gene expression in the somite," *Development*. 121: 651-660 (1995).

Nutt et al., "Commitment to the B-lymphoid lineage depends on the transcription factor Pax5," *Nature*. 401: 556-562 (1999).

Nutt et al., "Essential Functions of Pax-5 (BSAP) in pro-B Cell Development," *Immunobiology*. 198: 227-235 (1997).

Parker et al., "Looking Back to the Embryo: Defining Transcriptional Networks in Adult Myogenesis," *Nature Reviews: Genetics*. 4: 495-505 (2003).

Peters et al., "Pax1 and Pax9 synergistically regulate vertebral column development," *Development*. 126: 5399-5408 (1999).

Petropoulos and Skerjanc, "β-Catenin Is Essential and Sufficient for Skeletal Myogenesis in P19 Cells," *The Journal of Biological Chemistry*. 277: 15393-15399 (2002).

Polesskaya et al., "Wnt Signaling Induces the Myogenic Specification of Resident CD45+ Adult Stem Cells during Muscle Regeneration," *Cell*. 113: 841-852 (2003).

Qu-Petersen et al., "Identification of a novel population of muscle stem cells in mice: potential for muscle regeneration," *The Journal of Cell Biology*. 157: 851-864 (2002).

Relaix and Buckingham, "From insect eye to vertebrate muscle: redeployment of a regulatory network," *Genes & Development*. 13: 3171-3178 (1999).

Robertson, "Embryo-derived stem cell lines," in *Teratocarcinomas and embryonic stem cells: a practical approach*. Ch. 4: pp. 71-112 (1987).

Rolink et al., "Long-term in vivo reconstitution of T-cell development by Pax5-deficient B-cell progenitors," *Nature*. 401: 603-606 (1999).

Rosenblatt et al., "Satellite Cell Activity is Required for Hypertrophy of Overloaded Adult Rat Muscle," *Muscle & Nerve*. 17: 608-613 (1994).

Sabourin et al., "Reduced Differentiation Potential of Primary *MyoD-/-*Myogenic Cells Derived from Adult Skeletal Muscle," *The Journal of Cell Biology*. 144: 631-643 (1999).

Schultz et al., "Absence of exogenous satellite cell contribution to regeneration of frozen skeletal muscle," *Journal of Muscle Research and Cell Motility*. 7: 361-367 (1986).

Schultz et al.;, "Response of Satellite Cells to Focal Skeletal Muscle Injury," *Muscle & Nerve*. 8: 217-222 (1985).

Schultz and Jaryszak, "Effects of Skeletal Muscle Regeneration on the Proliferation Potential of Satellite Cells," *Mechanisms of Ageing and Development*. 30: 63-72 (1985).

Schwarz et al, "Conserved biological function between *Pax-2* and *Pax-5* in midbrain and cerebellum development: Evidence from targeted mutations," *Proceedings of the National Academy of Sciences*. 94: 14518-14523 (1997).

Sosa-Pineda et al., "The *Pax4* gene is essential for differentiation of insulin-producing β cells in the mammalian pancreas," *Nature*. 386: 399-409 (1997).

St-Onge et al., "*Pax6* is required for differentiation of glucagon-producing α-cells in mouse pancreas," *Nature*. 387: 406-409 (1997).

Tajbakhsh et al., "Differential activation of *Myf5* and *MyoD* by different Wnts in explants of mouse paraxial mesoderm and the later activation of myogenesis in the absence of *Myf5*,"*Development*. 125: 4155-4162 (1998).

Torban, "PAX2 Suppresses Apoptosis in Renal Collecting Duct Cells," *American Journal of Pathology*. 157: 833-842 (2000).

Torrente et al., "Intraarterial Injectin of Muscle-derived CD34+Sca-1+ Stem Cells Restores Dystrophin in *mdx* Mice," *The Journal of Cell Biology*. 152: 335-348 (2001).

Tremblay et al., "A Crucial Role for *Pax3* in the Development of the Hypaxial Musculature and the Long-Range Migration of Muscle Precursors," *Developmental Biology*. 203: 49-61 (1998).

Williams and Ordahl, "*Pax-3* expression in segmental mesoderm marks early stages in myogenic cell specification," *Development*. 120: 785-796 (1994).

Wilm et al., "Targeted disruption of *Pax1* defines its null phenotype and proves haploinsufficiency," *Proceedings of the National Academy of Sciences*. 95: 8692-8697 (1998).

Ziman et al., "Alternate *Pax7* Transcripts are Expressed Specifically in Skeletal Muscle, Brain and Other Organs of Adult Mice," *International Journal of Biochemical Cell Biology*. 28: 1029-1036 (1997).

* cited by examiner

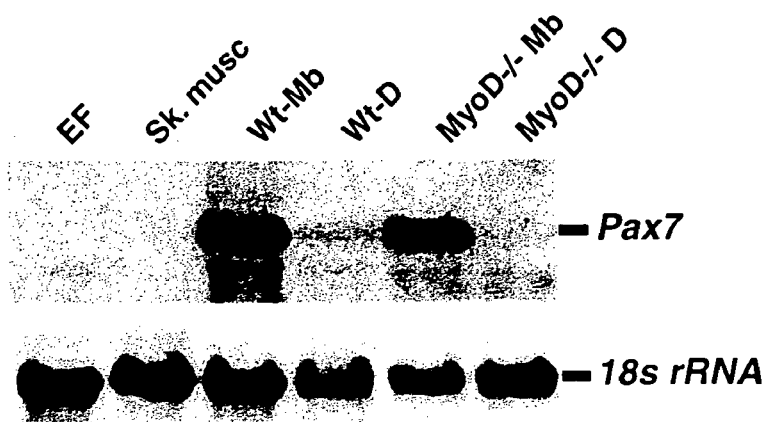
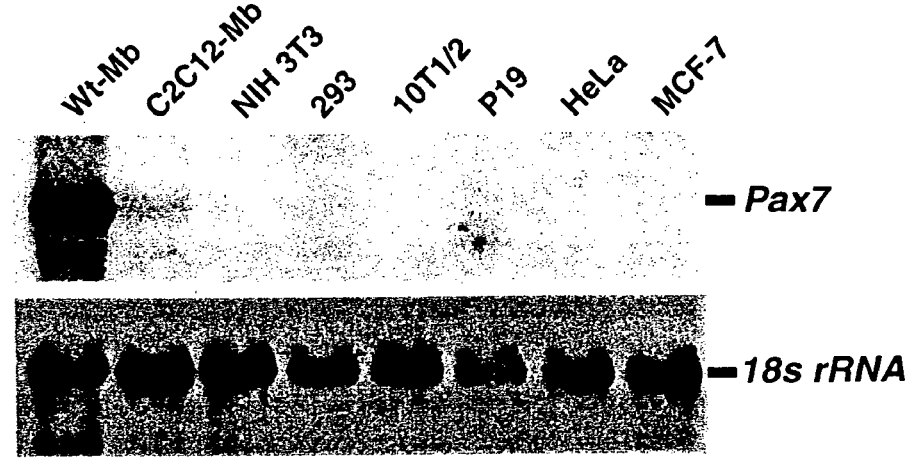
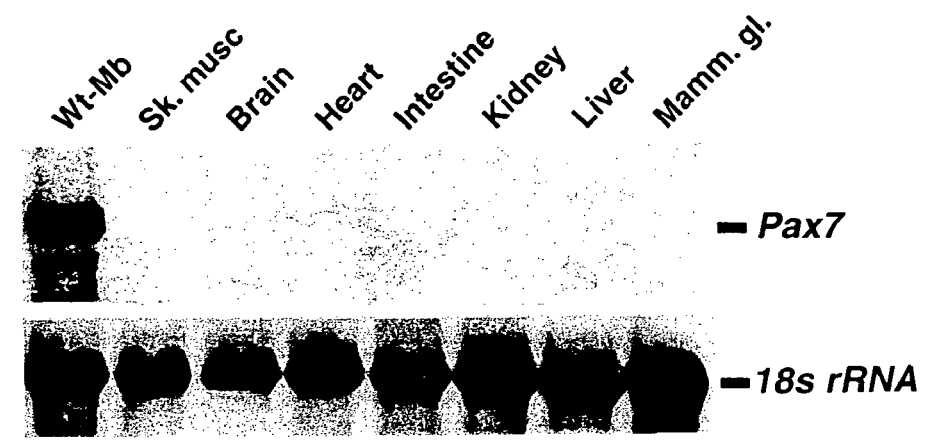
FIGURE 1

Ad-Pax7

```
  1 maalpgtvpr mmrpapgqny prtgfplevs tplgqgrvnq lggvfingrp lpnhirhkiv
 61 emahhgirpc visrqlrvsh gcvskilcry qetgsirpga iggskprqva tpdvekkiee
121 ykrenpgmfs weirdrllkd ghcdrstvps glvssisrvl rikfgkkeee deadkkeddg
181 ekkakhsidg ilgdkgnrld egsdvesepd lplkrkqrrs rttftaeqle elekaforth
241 ypdiytreel aqrtkltear vqvwfsnrra rwrkqaganq laafnhllpg gfpptgmptl
301 ppyqlpdsty pttisqdgg stvhrpqplp pstmhqggla aaaaadtss aygarhsfss
361 ysdsfmnpaa psnhmnpvsn glspqvmsil gnpsavppqp qadfsisplh ggldsatsis
421 ascsqradsi kpgdslptsq aycpptystt gysvdpvagy qygqygqsec lvpwaspvpi
481 psptprascl fmesykvvsg wgmsisqmek lkssqmeqft (SEQ ID NO:1)
```

```
  1 maalpgtvpr mmrpapgqny prtgfplevs tplgqgrvnq lggvfingrp lpnhirhkiv
 61 emahhgirpc visrqlrvsh gcvskilcry qetgsirpga iggskprqva tpdvekkiee
121 ykrenpgmfs weirdrllkd ghcdrstvps glvssisrvl rikfgkkeee deadkkeddg
181 ekkakhsidg ilgdkgnrld egsdvesepd lplkrkqrrs rttftaeqle elekaferth
241 ypdiytreel aqrtkltear vqvwfsnrra rwrkqaganq laafnhllpg gfpptgmptl
301 ppyqlpdsty ptttisqdgg stvhrpqplp pstmhqggla aaaaadtss aygarhsfss
361 ysdsfmnpaa psnhmnpvsn glspqvmsil gnpsavppqp qadfsisplh ggldsatsis
421 ascsqradsi kpgdslptsq aycpptystt gysvdpvagy qygqygqsec lvpwaspvpi
481 psptprascl fmesykvvsg wgmsisqmek lkssqmeqft (SEQ ID NO:2)
```

B

```
  1 maalpgtvpr mmrpapgqny prtgfplevs tplgqgrvnq lggvfingrp lpnhirhkiv
 61 emahhgirpc visrqlrvsh gcvskilcry qetgsirpga iggskprqva tpdvekkiee
121 ykrenpgmfs weirdrllkd ghcdrstvps vssisrvlri kfgkkeeede adkkeddgek
181 kakhsidgil gdkgnrldeg sdvesepdlp lkrkqrrsrt tftaeqlee ekaferthyp
241 diytreelaq rtkltearvq vwfsnrrarw rkqaganqia afnhllpggf pptgmptlpp
301 yqlpdstypt ttisqdggst vhrpqplpps tmhqgglaaa aaadtssay garhsfssys
361 dsfmnpaaps nhmnpvsngl spqvmsilgn psavppqpqa dfsisplhgg ldsatsisas
421 csqradsikp gdslptsqay cpptysttgy svdpvagyqy gqygqseclv pwaspvpips
481 ptprasclfm esykvvsgwg msisqmeklk ssqmeqft (SEQ ID NO:3)
```

Figure 14

```
  1 maalpgtvpr mmrpapggny prtgfplevs tplgqgrvnq lggvfingrp lpnhirhkiv
 61 emahhgirpc visrqlrvsh gcvskilcry qetgsirpga iggskprqva tpdvekkiee
121 ykrenpgmfs weirdrllkd ghcdrstvps glvssisrvl rikfgkkeee deadkkeddg
181 ekkakhsidg ilgdkgnrld egsdvesepd lplkrkqrrs rttftaeqle elekaferth
241 ypdiytreel aqrtkltear vqvwfsnrra rwrkqaganq laafnhllpg gfpptgmptl
301 ppyqlpdsty ptttisqdgg stvhrpqplp pstmhqggla aaaaaedtss aygarhsfss
361 ysdsfmnpaa psnhmnpvsn glspqvmsil gnpsavppqp qadfsisplh ggldsatsls
421 ascsqradsi kpgdslptsq aycpptystt gysvdpvagy qygqygqsec lvpwaspvpi
481 psptprascl fmesykvvsg wgmsisqmek lkssqmeqft (SEQ ID NO:4)
```

Figure 15

```
  1 maalpgtvpr mmrpapgqny prtgfplevs tplgqgrvnq lggvfingrp lpnhirhkiv
 61 emahhgirpc visrqlrvsh gcvskilcry qetgsirpga iggskprqva tpdvekkiee
121 ykrenpgmfs weirdrllkd ghcdrstvps glvssisrvl rikfgkkeee deadkkeddg
181 ekkakhsidg ilgdkgnrld egsdvesepd lplkrkqrrs rttftaeqle elekaferth
241 ypdiytreel aqrtkltear vqvwfsnrra rwrkqaganq laafnhllpg qfpptgmptl
301 ppyqlpdsty ptttisqdgg stvhrpqplp pstmhqggla aaaaaadtss aygarhsfss
361 ysdefmnpaa psnhmnpvsn glspqvmsil gnpsavppqp qadfsisplh ggldsatsis
421 ascsqradsi kpgdslptsq aycpptystt gysvdpvagy qygqygqsec lvpwaspvpi
481 psptprascl fmesykvvsg wgmsisqmek lkssqmeqft (SEQ ID NO:5)
```

Figure 16

```
  1 maalpgtvpr mmrpapgqny prtgfplevs tplgqgrvnq lggvfingrp lpnhirhkiv
 61 emahhgirpc visrqlrvsh gcvskilcry qetgsirpga iggskprqva tpdvekkiee
121 ykrenpgmfs weirdrllkd ghcdrstvps glvssisrvl rikfgkkeee deadkkeddg
181 ekkakhsidg ilgdkgnrld egsdvesepd lplkrkqrrs rttftaeqle elekaferth
241 ypdiytreel agrtkltear vqvwfsnrra rwrkqaganq laafnhllpg gfpptgmptl
301 ppyqlpdsty ptttisqdgg stvhrpqplp pstmhqggla aaaaaadtss aygarhsfss
361 ysdsfmnpaa psnhmnpvsn glspqvmsil gnpsavppqp qadfsisplh ggldsatsis
421 ascsqradsi kpgdslptsq aycpptystt gysvdpvagy qygqygq (SEQ ID NO:6)
```

Figure 17

```
  1 maalpgtvpr mmrpapgqny prtgfplevs tplgqgrvnq lggvfingrp lpnhirhkiv
 61 emahhgirpc visrqlrvsh gcvskilcry qetgsirpga iggskprqva tpdvekkiee
121 ykrenpgmfs weirdrllkd ghcdrstvps vssisrvlri kfgkkeeeed cdkkeedgek
181 kakhsidgil gdkgnrldeg sdvesepdlp lkrkqrrsrt tftaeqleel ekaferthyp
241 diytreelaq rtkltearvq vwfsnrrarw rkqaganqla afnhllpggf pptgmptlpp
301 yqlpdstypt ttisqdggst vhrpqplpps tmhqgglaaa aaadsssayg arhsfssysd
361 sfmnaaapan hmnpvsngls pqkqgaqnkm qcsrwnltia lnnqvmsils npsgvppqpq
421 adfsisplhg gldttnsisa scsqrsdsik svdslptsqs ycpptystts ysvdpvagyq
481 ygqygqtavd yltknvslst qrrmklgehs avlgllpvet gqay (SEQ ID NO:7)
```

Figure 18

```
  1 mttlagavpr mmrpgpgqny prsgfplevs tplgqgrvnq lggvfingrp lpnhirhkiv
 61 emahhgirpc visrqlrvsh gcvskilcry qetgsirpga iggskpkqvt tpdvekkiee
121 ykrenpgmfs weirdkllkd avcdrntvps vssisrilrs kfgkgeeeea dlerkeaees
181 ekkakhsidg ilserasapq sdegsdidse pdlplkrkqr rsrttftaeq leelerafer
241 thypdiytre elaqraklte arvqvwfsnr rarwrkqaga nqlmafnhli pggfpptamp
301 tlptyqlset syqptsipqa vsdpsstvhr pqplppstvh qstipsnpds ssayclpstr
361 hgfssytdsf vppsgpsnpm nptignglsp qvmglltnhg gvphqpqtdy aispltggle
421 ptttvsascs qrldhmksld slptsqsycp ptysttgysm dpvtgycygq ygqskpwtf
    (SEQ ID NO:8)
```

Figure 19

```
  1 mttlagavpr mmrpgpgqny prsgfplevs tplgqgrvnq lggvfingrp lpnhirhki
 61 emahhgirpc visrqlrvsh gcvskilcry qetgsirpga iggskpkqvt tpdvekkiee
121 ykrenpgmfs weirdkllkd avcdrntvps vssisrilrs kfqkgeeeea dlerkeaees
181 ekkakhsidg ilsergkrwr lgrrtcwvtw rasas(SEQ ID NO:9)
```

Figure 20

```
  1 mttlagavpr mmrpgpgqny prsgfplevs tplgggrvnq lggvfingrp lpnhirhkiv
 61 emahhgirpc visrqlrvsh gcvskilcry getgsirpga iggskpkqvt tpdvekkiee
121 ykrenpgmfs weirdkllkd avcdrntvps vssisrilrs kfgkgeeeea dlerkeaees
181 ekkakhsidg ilsergkalv sgvssh (SEQ ID NO:10)
```

Figure 21

```
  1 psvssisril rskfgkgeee eadlerkeae esekkakhsi dgilserasa pqsdegsdid
 61 sepdlplkrk qrrsrttfta eqleelehva ferthypdiy treelaqrak ltearvqvwf
121 snrrarwrkq aganqlmafn hlipggfppt amptlptyql sehsyqptsi pqavsdpsst
181 vhrpqplpps tvhqstipsn pdsssayclp strhgfssyt dsfvppsgps npmuptigng
241 lspqvmgllt nhggvphqpq tdyalspltg qleptttvsa scsqrldhmk sldslptsqs
301 ycpptysttg ysmdpvtgyq ygqygqskpw tf (SEQ ID NO:11)
```

Figure 22

```
  1 mttlagavpr mmrpgpgqny prsgfplevs tplgqgrvnq lggvfingrp lpnhirhkiv
 61 emahhgirpc visrqlrvsh gcvskilcry qetgsirpga iggskpkqvt tpdvekkiee
121 ykrenpgmfs weirdkllkd avcdrntvps vssisrilrs kfgkgeeeea dlerkeaees
181 ekkakhsidg ilserasapq sdegsdidse pdlplkrkqr rsrttftaeq leelerafer
241 thypdiytre elaqraklte arvqvwfsnr rarwrkqaga nqlmafnhli pggfpptamp
301 tlptyqlseh syqptsipqa vsdpsstvhr pqplppstvh qstipsnads ssayclpstr
361 hgfssytdsf vppsgpsnpm nptignglsp qvmglltnhg gvphqpqtdy alspltggle
421 ptttvsascs qrlehmknvd slptsqpycp ptystagysm dpvtgyqygq ygqskpwtf
      (SEQ ID NO:12)
```

Figure 23

```
  1 gggrvnqlgg vfingrplpn hirhkivqma hhgirpcvis rqlrvshgcv skilcryqet
 61 gsirpgaigg skpkqvttpd vekkieeykr enagmfswei rdrllkdgvc drntvpsvss
121 islilrskfq rrertrftae qleelerafe rthypdiytr eelaqraklt earvqvwfsn
181 rrarwrkqag(SEQ ID NO:13)
```

Figure 24

PAX-ENCODING VECTOR AND USE THEREOF

CROSS REFERENCE TO RELATED APPLICATIONS

This application is a Continuation-In-Part of U.S. application Ser. No. 10/245,171 filed Sep. 17, 2002 now abandoned, which claims benefit of U.S. Provisional application 60/322,923 filed Sep. 17, 2001, both of which are hereby incorporated by reference.

BACKGROUND OF THE INVENTION

The present invention relates to the field of Pax-encoding vectors and more particularly to vectors comprising sequences that encode Pax7, Pax3, and/or biologically active variants or fragments thereof, and their use to induce differentiation of adult stem cells to produce myoblasts. The present invention also relates to cells transformed with a nucleotide sequence encoding Pax proteins.

Myoblasts are precursor cells of the mesoderm that are destined for myogenesis. The determined myoblasts are capable of recognising and spontaneously fusing with other myoblasts leading to the production of a differentiated myotube. The multinucleated myotube no longer divides or synthesises DNA but produces muscle proteins in large quantities. These include constituents of the contractile apparatus and specialised cell-surface components essential to neuromuscular transmission.

Eventually, the differentiated muscle cell exhibits characteristic striations and rhythmic contractions. A further step in this pathway is maturation; the contractile apparatus and muscle at different stages of development contain distinct isoforms of muscle proteins such as myosin and actin, encoded by different members of multigene families.

Myoblasts have the potential for being used in a variety of ways. For example, the myoblasts may serve as vehicles for cell therapy, where one or more genes may be introduced into the myoblasts to provide a protein of interest. In order to find wide utility in therapeutic applications, however, it will be necessary to develop methods for the sustained production by myoblasts carrying the gene of interest.

Myoblasts are thought to be capable of repairing damaged or injured myofibers (Mauro, A., J. Biophys. Biochem. Cytol., 9: 493-495 (1961); Bischoff, R., in Mvology, Engel, A. G. and Franzini-Armstrong, C., Eds., New York: McGraw Hill, pp. 97-119, 1994; and Grounds, M., Adv. Exp. Med. Biol., 280: 101-104 (1990)). Because myoblasts are thought to be capable of repairing damaged or injured myofibers, the technique of myoblast transfer (myoblast transplantation) has been proposed as a potential therapy or cure for muscular diseases, including Duchenne muscular dystropy (DMD).

Myoblast transfer involves injecting myoblast cells into the muscle of a mammal, particularly a human patient, requiring treatment. Although developed muscle fibres are not regenerative, the myoblasts are capable of a limited amount of proliferation, thus increasing the number of muscle cells at the location of myoblast infusion. Myoblasts so transferred into mature muscle tissue will proliferate and differentiate into mature muscle fibres. This process involves the fusion of mononucleated myogenic cells (myoblasts) to form a multinucleated syncytium (myofiber or myotube). Thus, it has been proposed that muscle tissue which has been compromised either by disease or trauma may be supplemented by the transfer of myoblasts into the compromised tissue.

Moreover, cell cultures are widely used as in vitro models for studying the events involved during in vivo cellular or tissue development. For example, muscle developmental events can be reproduced during the myogenic differentiation of stem cell cultures. Accordingly, permanent mammalian cell cultures, especially human myogenic cell cultures, would be of considerable value for providing useful tools for dissecting the molecular and biochemical cellular events, for identifying and testing new drugs for muscular diseases, such as dystrophies, for the study of myogenesis, etc.

The "paired-box" family of transcription factors is intimately involved in the control of embryonic development. Different members of the Pax family of transcription factors appear to regulate the development and differentiation of diverse cell lineages during embryogenesis (see Table 1) (Mansouri et al., 1999; Mansouri et al., 1994; Noll, 1993; Strachan and Read, 1994). Pax7 and the closely related Pax3 gene belong to a paralogous subgroup of Pax genes based on similar protein structures and partially overlapping expression patterns during mouse embryogenesis (Goulding et al., 1991; Jostes et al., 1990). Interestingly, Pax3 gene plays an essential role in regulating the developmental program of MyoD-dependent migratory myoblasts during embryogenesis (Maroto et al., 1997; Tajbakhsh et al., 1997).

Pax7 and Pax3 proteins bind identical sequence-specific DNA elements suggesting that they regulate similar sets of target genes (Schafer et al., 1994). Furthermore, increased expression and gain-of-function mutations in both Pax3 and Pax7 are associated with the development of alveolar rhabdomyosarcomas indicating that both molecules regulate similar activities in myogenic cells (Bennicelli et al., 1999). However, Pax7 but not Pax3 is expressed in adult human primary myoblasts (Schafer et al., 1994). Interestingly, differential expression of alternatively spliced Pax7 transcripts correlates with muscle regenerative efficiency in different strains of mice (Kay et al., 1998; Kay et al., 1997; Kay et al., 1995; Kay and Ziman, 1999).

Skeletal muscle regeneration has long been considered to be mediated solely by monopotential skeletal muscle stem cells known as satellite cells (Bischoff, 1994; Charge and Rudnicki, 2004). However, recent studies have identified novel populations of adult stem cells in skeletal muscle. For example, "side-population" (SP) cells isolated from muscle tissue participate in the regeneration of skeletal muscle and give rise to satellite cells (Asakura et al., 2002; Gussoni et al., 1999). In vitro, muscle SP cells readily form hematopoietic colonies, but do not spontaneously differentiate into muscle cells unless cocultured with satellite cell derived myoblasts (Asakura et al., 2002).

Various cell surface markers have been employed to purify adult stem cell populations from skeletal muscle, including c-kit, Sca1, CD34, and CD45 (reviewed by Charge and Rudnicki, 2004). Almost all muscle-derived hematopoietic progenitor and blood reconstitution activity is derived from CD45+ cells (Asakura et al., 2002; McKinney-Freeman et al., 2002). Muscle-derived CD45+ cells purified from uninjured muscle are uniformly non-myogenic in vitro and do not form muscle in vivo (Asakura et al., 2002; McKinney-Freeman et al., 2002). However, coculture and in vivo injection experiments indicate that CD45+ SP as well as CD45– SP cells possess myogenic potential (Asakura et al., 2002; McKinney-Freeman et al., 2002).

There is a need in the art for novel cells that are capable of differentiating into muscle cells. Further, there is a need in the art for methods of promoting myogenic specification of stem cells. There is also a need in the art for novel uses and methods of treating a subject having a disease with stem cells that are capable of differentiating into muscle cells.

It is an object of the invention to overcome disadvantages of the prior art.

The above object is met by the combinations of features of the main claims. The sub-claims disclose further advantageous embodiments of the invention.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates to an object of the present invention is to provide Pax7-encoding vectors and use thereof. In accordance with an aspect of the present invention, there is provided a vector comprising an expression cassette comprising a sequence encoding a Pax protein, wherein the Pax protein is selected from the groups consisting of: Pax7; Pax3; an active variant of Pax 7; an active variant of Pax 3; an active fragment of Pax 7; and an active fragment of Pax 7, and wherein the Pax protein can induce myogenic differentiation of adult stem cells.

In accordance with another aspect of the invention, there is provided a method of differentiating adult stem cells to produce myoblasts comprising the step of transforming or infecting the stem cells with a vector comprising an expression cassette comprising a sequence encoding a Pax protein, wherein the Pax protein is selected from the groups consisting of: Pax7; Pax3; an active variant of Pax 7; an active variant of Pax 3; an active fragment of Pax 7; and an active fragment of Pax 7.

In accordance with another aspect of the invention, there is provided use of myoblasts produced according to the methods described herein for transplantation in a mammal in need of such therapy.

According to the present invention there is provided a stem cell transformed with a nucleotide sequence encoding Pax7, Pax3 or both. Preferably the stem cell is derived from muscle, more preferably skeletal muscle. The cell may be derived from a subject after birth, for example, but not limited to an adult. The cell is a mammalian cell, preferably selected from the group consisting of mice, cattle, sheep, goat, pig, dog, cat, rat, rabbit, primate, and human. However, other species are also contemplated. Preferably the stem cell is a CD45+:Sca1+ cell. However, in an alternate embodiment, the stem cell may be a CD45−:Sca1+ cell.

The present invention also provides a stem cell as defined above, wherein the nucleotide sequence additionally encodes one or more wild-type muscle proteins, one or more wild-type muscle variant proteins, or a combination thereof. The one or more wild-type muscle proteins or the one or more wild-type variant muscle proteins may comprise dystrophin, calpain-3, one or more sarcoglycan complex members, α-sarcoglycan, β-sarcoglycan, γ-sarcoglycan and δ-sarcoglycan, laminin, actin, myosin, calcineurin, NFATc1, NFATc2, NFATc3, utrophin or a combination thereof.

The present invention also provides a composition comprising one or more stem cells as defined above and an acceptable carrier, preferably a pharmaceutically acceptable carrier, wherein the one or more cells are defined as being selected from the group consisting of a) an adult stem cell;
b) a skeletal muscle stem cell;
c) a muscle satellite cell;
d) a side population cell;
e) a CD45+:Sca1+ cell;
f) a CD45−:Sca1+ cell, and;
g) a Sca1+ cell.

The acceptable carrier may be any carrier known in the art, for example, but not limited to a cell culture medium, a cell growth medium, a cell cryopreservation medium, an assay medium, an isolation medium, or a delivery or administration medium.

Also contemplated by the present invention is a method of treating a subject having a muscular degenerative disease comprising,
   administering a plurality of cells as defined above to the subject having said muscular degenerative disease.

Also provided is a method of treating a subject having a muscular degenerative disease comprising, administering the composition as defined above to the subject having the muscular degenerative disease.

In a preferred embodiment the cells comprise CD45+:Sca1+ cells.

The present invention also provides a method as defined above wherein the cells are transformed with a nucleotide sequence encoding one or more wild-type proteins, one or more wild-type variant proteins, or a combination thereof.

The muscular degenerative disease may be wholly or partially a result of one or more mutations, deletions, inversions, insertions or a combination thereof in one or more promoters, regulatory sequences or genes encoding one or more proteins in the subject, and;
   the one or more wild-type proteins may correspond to wild-type proteins of the one or more mutant proteins in the subject with the muscular degenerative disease.

The present invention also provides a method of treating a first subject having a muscular degenerative disease comprising,
a) isolating a plurality of muscle stem cells from a second subject lacking the muscular degenerative disease, the stem cells comprising CD45+:Sca1+ muscle stem cells;
b) transforming the cells with a nucleotide construct encoding Pax7, Pax3 or a combination thereof;
c) expressing the Pax7, Pax3 or combination thereof in the cells, and;
d) administering the cells to the first subject having the muscular degenerative disease.

Preferably, the first subject and the second subject are immunologically matched.

It is also contemplated that the stem cells may be subjected to one or more purification steps to preferentially enrich for CD45+:Sca1+ stem cells, for example, but not limited to after the step of isolating, transforming or both. In a specific embodiment of the present invention, the purification step may comprise flow cytometry. It is also contemplated that the cells may be subjected to one or more selection steps to select, enrich and/or identify cells transformed with a nucleotide sequence encoding Pax7, Pax3 or both The present invention also provides a method of treating a subject exhibiting a muscular degenerative disease caused by one or more genetic alterations in one or more genes of the subject comprising,
a) isolating a plurality of muscle stem cells from the subject, the stem cells comprising CD45+/Sca1+ muscle stem cells;

b) transforming the cells with one or more nucleotide sequences, the one or more nucleotide sequences encoding
   i) Pax7, Pax3 or a combination thereof, and;
   ii) one or more wild-type proteins of the one or more genes;
c) expressing the Pax7, Pax3 or combination thereof and the one or more wild-type proteins in the cells, and;
d) administering the cells to the subject exhibiting the muscular degenerative disease.

Also provided is a method of treating a subject exhibiting a muscular degenerative disease comprising, a) administering a composition comprising a vector, the vector comprising a nucleotide sequence encoding Pax7, Pax3 or a combination thereof to the subject, wherein the vector is capable of infecting one or more types of cells in the subject;

b) expressing the Pax7, Pax3, or combination thereof in the cells of the subject.

Also provided by the present invention is a method of treating skeletal muscle damage or deterioration in a subject comprising, administering stem cells or a composition comprising stem cells as defined above to a subject.

Preferably, the stem cells comprise CD45+:Sca1+ cells.

The skeletal muscle damage or deterioration may be disease related or non-disease related. In the case it is disease related, the skeletal muscle damage and/or deterioration may be associated with a disease such as, but not limited to aids or cancer.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows that Pax7 is expressed specifically in proliferating myoblasts. (A) Pax7 was expressed at high levels in proliferating wild-type myoblasts (Wt-Mb) and MyoD-deficient cells (MyoD−/−Mb) cells and down regulated in response to differentiation conditions (Wt-D and MyoD−/−D). (B) Expression of Pax7 was specific to myogenic cells with low levels detected in C2C 12 myoblasts. (C) Pax7 was not detected in RNA from a panel of tissues.

Stem cells (msc) within muscle represent the progenitors of sublaminar satellite cells that are specified following induction of Pax7. Satellite cells are subsequently activated in response to physiological stimuli to generate daughter myogenic precursor cells (mpc) prior to terminal differentiation into new or previously existing fibres.

Figure 8:
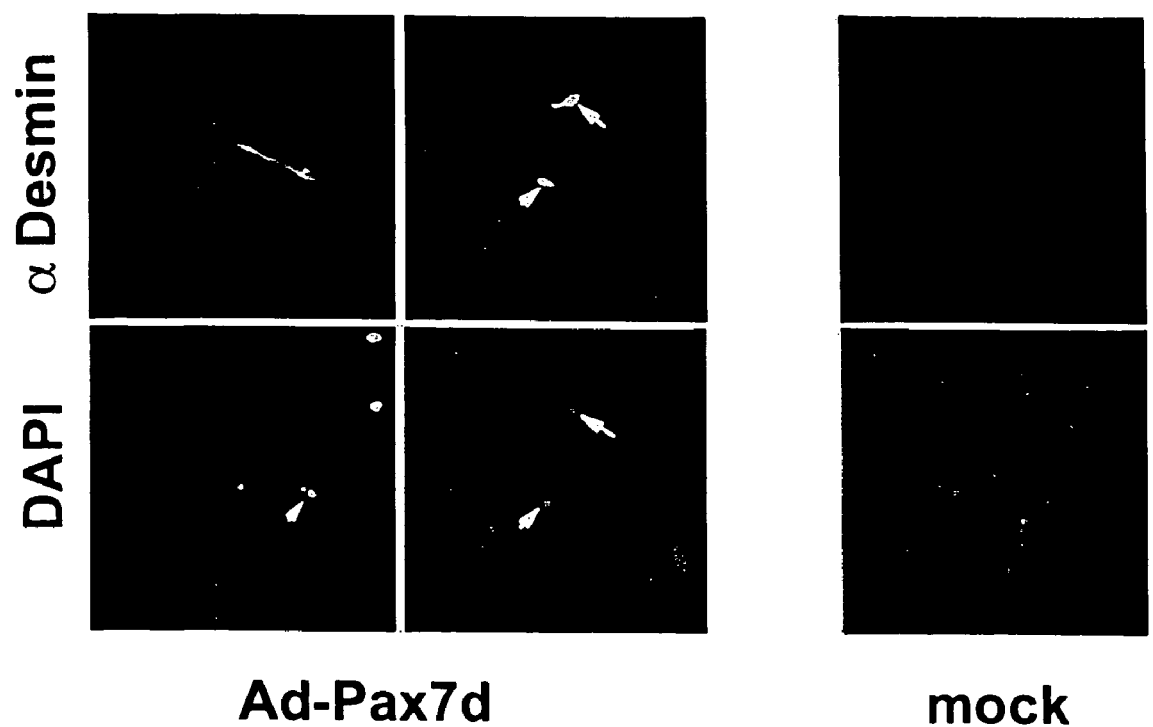

FIG. 8 shows a demonstration of myogenic specification of SP cells. Fractionated SP cells infected with Ad-empty control virus (mock) and Ad-Pax7 virus (Ad-Pax7d) were analysed for expression of desmin and counter-stained with DAPI to show all nuclei.

Figure 9:
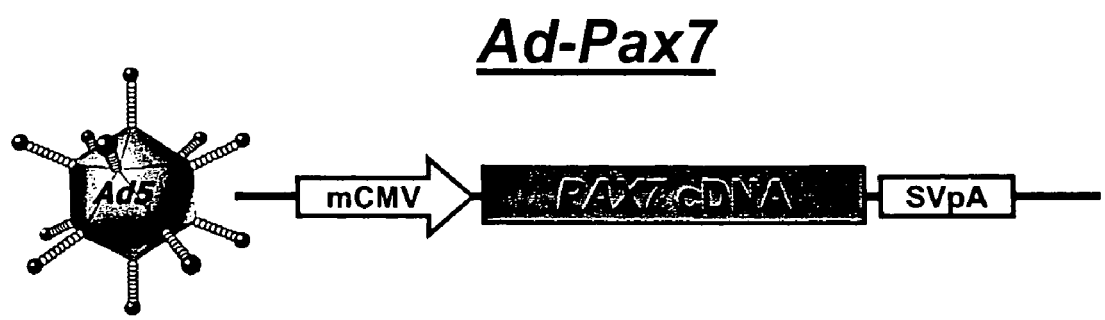

FIG. 9 shows the structure of an exemplary adenovirus-Pax7. Pax7 is expressed under the control of the murine CMV promoter (mCMV). The SV40 poly A (SVpA) sequence is downstream of the cDNA.

Figure 10:
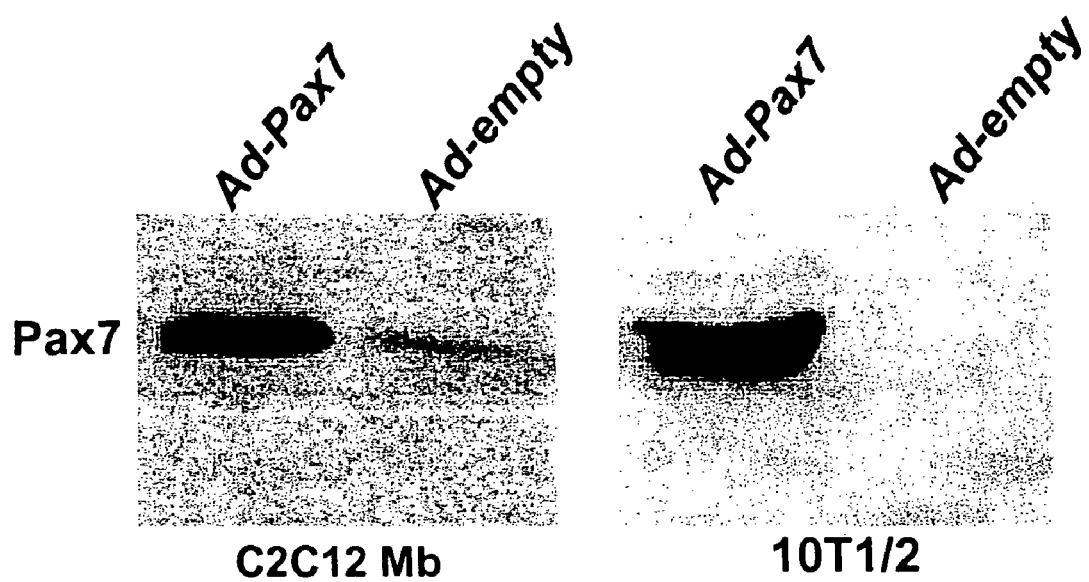

FIG. 10 shows western analysis of Ad-Pax7 infected Cells. C2C12 myoblasts or 10T1/2 fibroblasts were infected with either Ad-Pax7 or Ad-empty. Western analysis indicates that Pax7 protein is expressed at high levels from the recombinant Ad-Pax7 virus. C2C 12 myoblasts expressed low-levels of endogenous Pax7.

Figure 11:
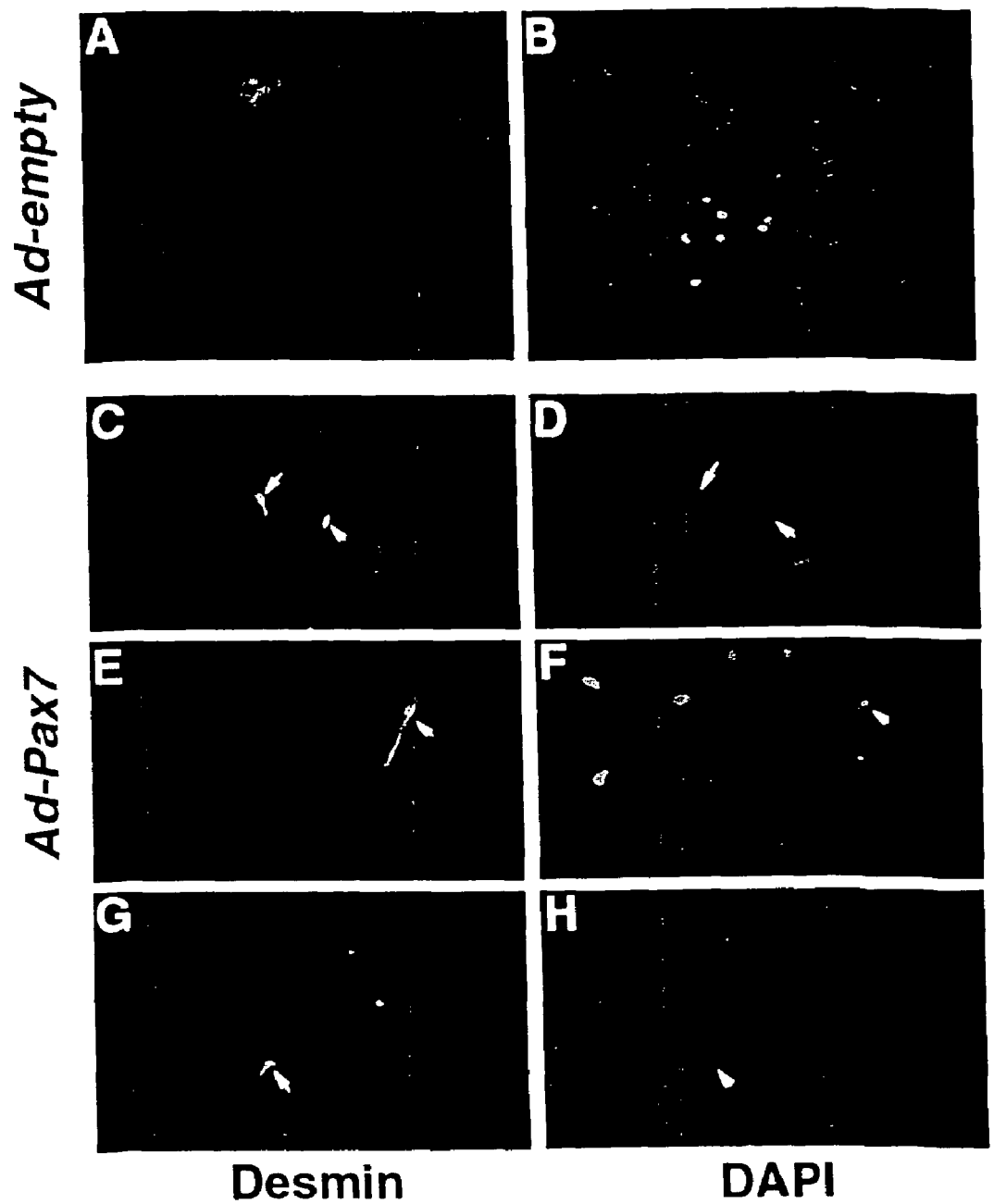

FIG. 11 shows a demonstration of myogenic specification of SP cells. Fractionated SP cells infected with Ad-empty control virus (A,B) and Ad-Pax7 virus (C-H) were analysed for expression of desmin (A,C,E,G) and counter-stained with DAPI to show all nuclei (B,D,F,H).

Figure 12:
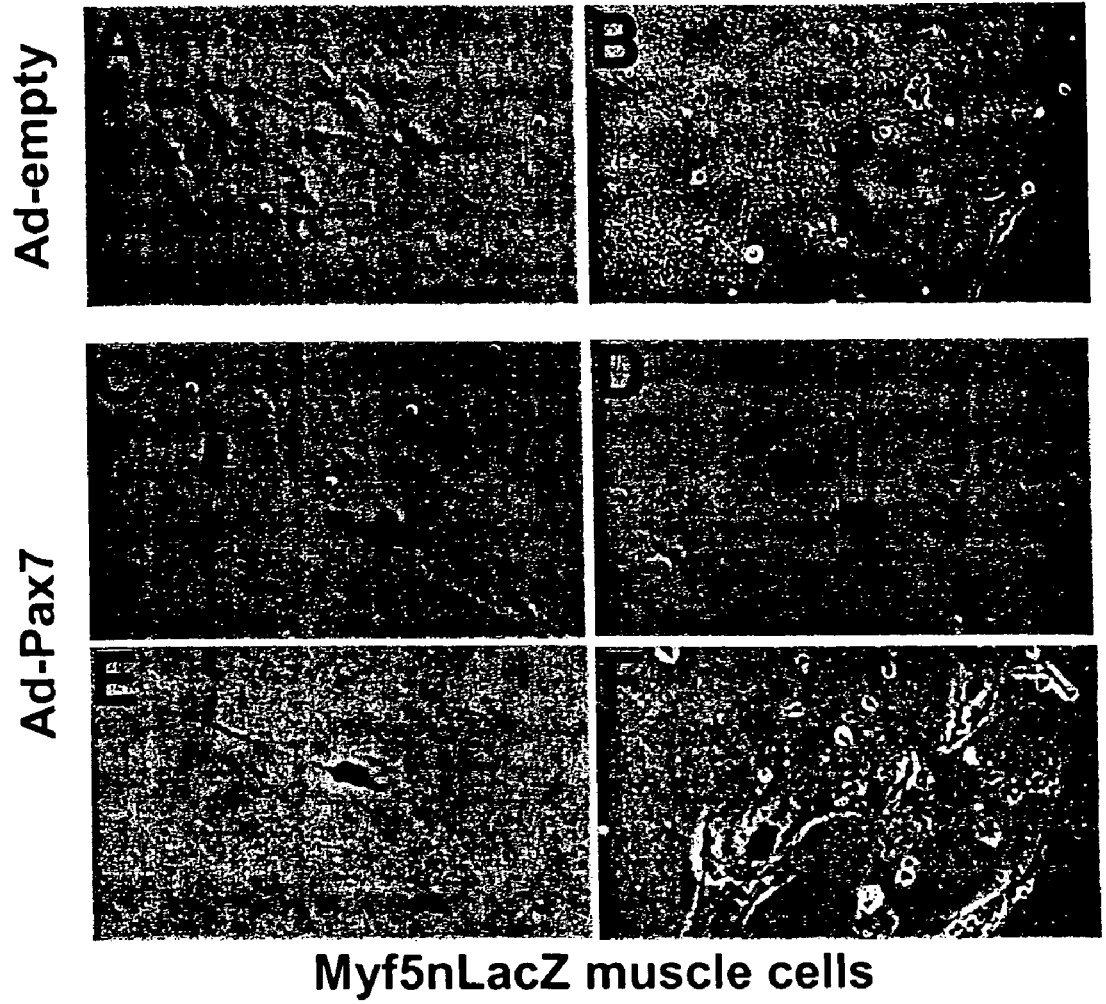

FIG. 12 shows induction of Myf5lacZ by Pax7. Muscle-derived cells from Myf5nlacZ transgenic mice were infected with Ad-empty (A,B) orAd-Pax7 (C-F). Expression of Pax7 resulted in up-regulation of Myf5nLacz indicating entry into the myogenic differentiation program.

FIG. 13 shows the amino acid sequence of a human Pax7 protein (NCBI Accession number NM_002584) (SEQ ID NO:1).

FIG. 14 shows the amino acid sequence of variants of the human Pax7 protein (A NCBI Accession number $NP_{13}$ 002575 (SEQ ID NO:2); B NCBI Accession number NM_013945) (SEQ ID NO:3).

FIG. 15 shows the amino acid sequence of a long splice form of human Pax7 protein (NCBI Accession number S78502) (SEQ ID NO:4).

FIG. 16 shows the amino acid sequence of a human Pax7 protein (NCBI Accession number CAA16432) (SEQ ID NO:5).

FIG. 17 shows the amino acid sequence of a fragment of a human Pax7 protein (NCBI Accession number S50 115) (SEQ ID NO:6).

FIG. 18 shows the amino acid sequence of a chicken Pax7 protein (NCBI Accession number BAA23005) (SEQ ID NQ:7).

FIG. 19 shows the amino acid sequence of a human Pax3 protein (NCBI Accession number P23760) (SEQ ID NO:8).

FIG. 20 shows the amino acid sequence of a human Pax3A protein (NCBI Accession number NP_000429) (SEQ ID NO:9).

FIG. 21 shows the amino acid sequence of a human Pax3B protein (NCBI Accession number NP_039230) (SEQ ID NO: 10).

FIG. 22 shows the amino acid sequence of a human Pax3 protein (NCBI Accession number AAA03628) (SEQ ID NO:11).

FIG. 23 shows the amino acid sequence of a mouse Pax3 protein (NCBI Accession number NP_032807) (SEQ ID NO:12).

FIG. 24 shows the amino acid sequence of a chicken Pax3 protein (NCBI Accession number AH004319) (SEQ ID NO:13).

Figure 25:
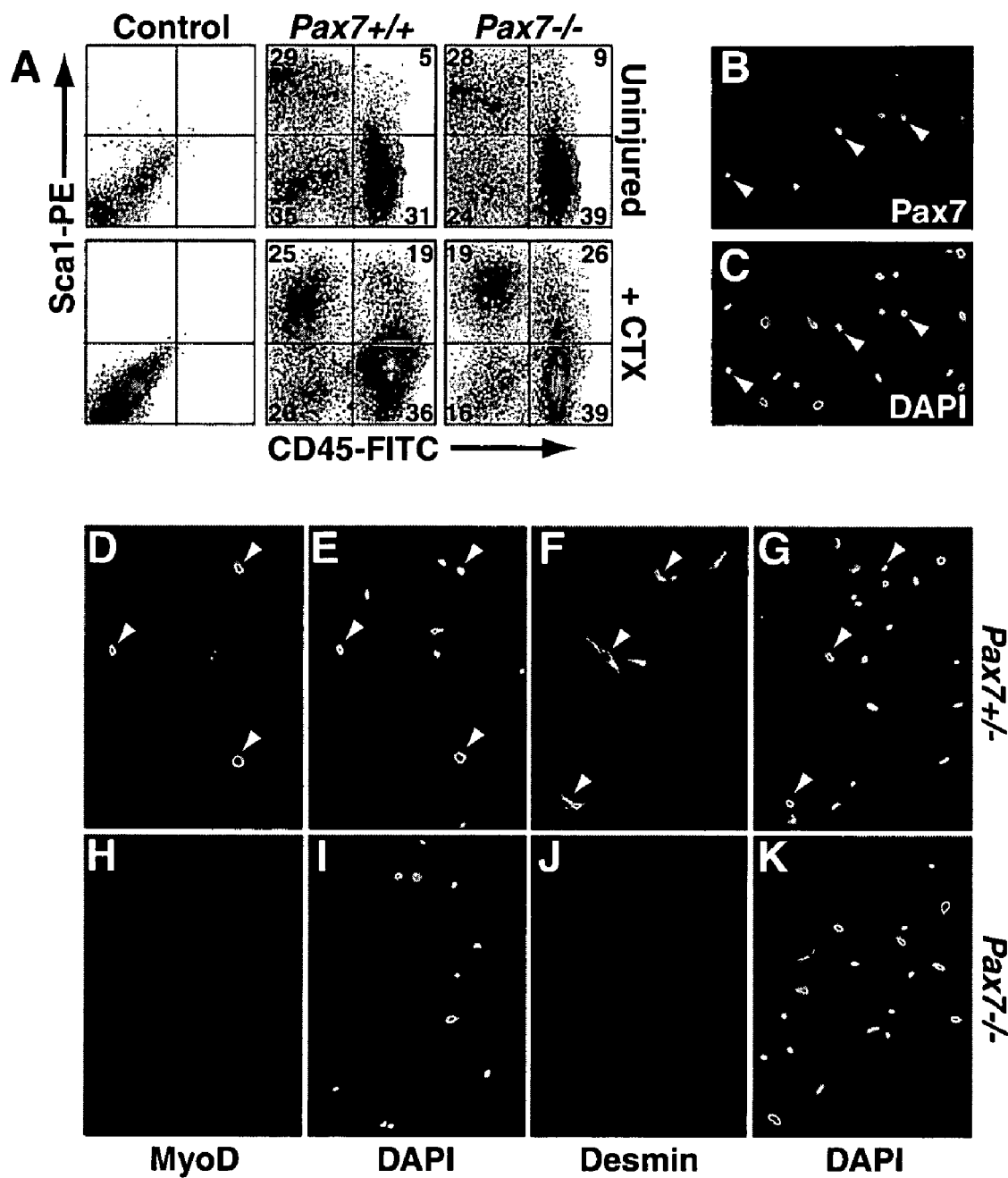

FIG. 25 shows results of the effect of Pax7 on the myogenic specification of CD45+:Sca1+ cells. FIG. 25A shows results obtained from flow cytometric analysis of cell suspensions derived from uninjured and regenerating wild-type and Pax7−/− muscle (4 days after cardiotoxin (ctx) injection) FIG. 25B,C show results that Pax7 protein was expressed in CD45+:Sca1+ cells purified from regenerating Pax 7± muscle. MyoD (FIG. 25D,E) and Desmin (FIG. 25F,G) were induced in CD45+:Sca1+ cells from regeneratingPax7± but were not expressed in CD45+:Sca1+ cells from regenerating Pax7−/− muscle (FIG. 25H,K).

Figure 26:
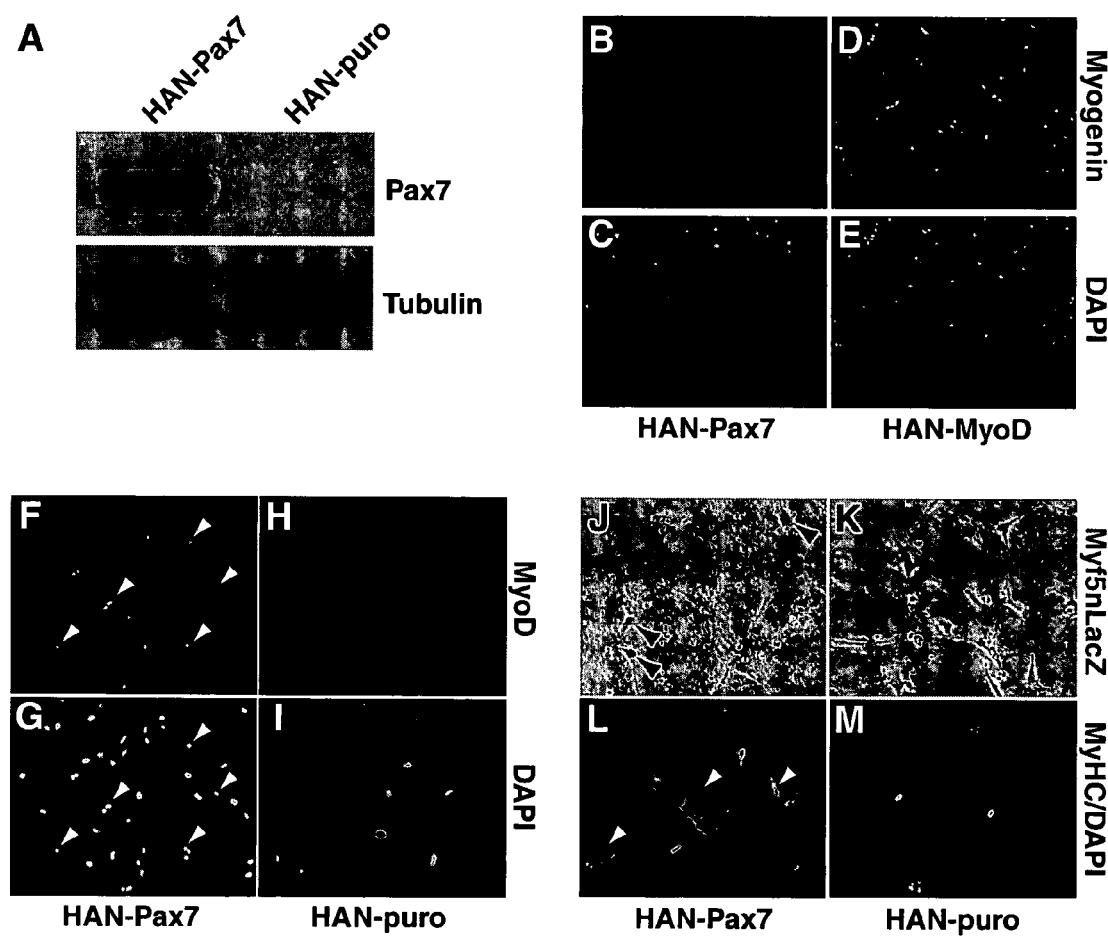

FIG. 26 shows results suggesting that Pax7 induces myogenic commitment in CD45+:Sca1+ cells. FIG. 26A shows results of Western blot analysis with anti-Pax7 antibody that confirmed high levels of ectopic Pax7 in C3H10T1/2 cells infected with retrovirus-Pax7 (HAN-Pax7) but not with control virus expressing a puromycin resistance marker (HAN-puro). HAN-Pax7 did not induce expression of myogenin in C3H10T1/2 cells (FIG. 26B,C). By contrast, MyoD virus (HANMyoD) efficiently converted C3H10T1/2 cells to myogenin expressing myocytes (green) (FIG. 26D,E). HAN-Pax7 (FIG. 26F,G) but not HAN-puro (FIG. 26H,I) activated expression of MyoD (red) in CD45+:Sca1+ cells from uninjured muscle. HAN-Pax7 (J) but not HAN-puro (K) also induced Myf5nLacZ expression in CD45+:Sca1+ cells.

Furthermore, HAN-Pax7 infected CD45+:Sca1+ cultures differentiated into Myosin Heavy Chain expressing myocytes (green) under differentiation conditions (L), whereas HAN-puro infected cells did not undergo myogenic differentiation (M). DAPI staining (blue) was used to visualize all nuclei.

Figure 27:
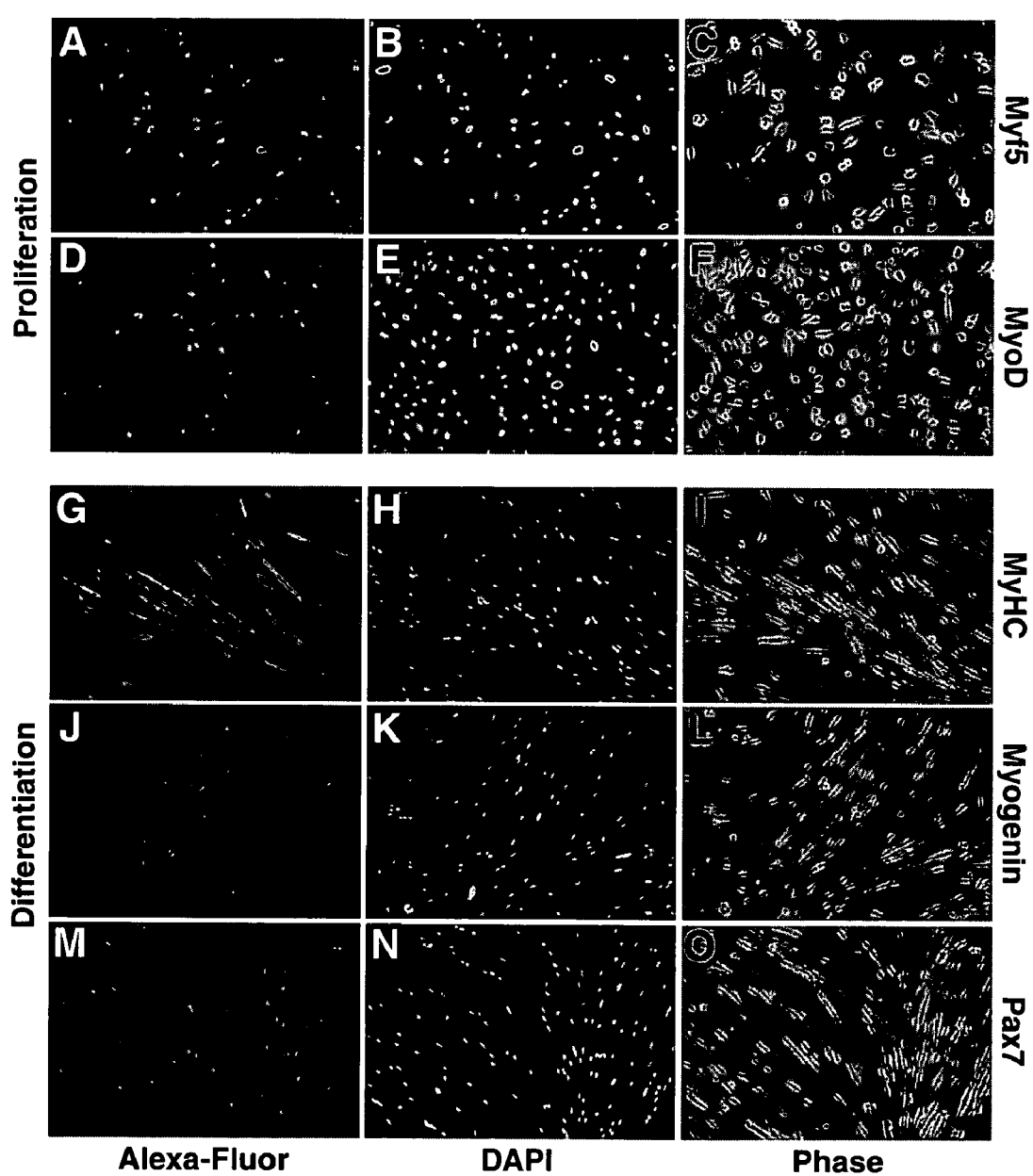

FIG. 27 shows results that CD45+:Sca1+ cells expressing Pax7 (CDSC-Pax7) become myogenic. Progenitors Myf5 (FIG. 27A-C) and MyoD (FIG. 27D-F) protein (green) are expressed in proliferating CDSC-Pax7 cells. Exposure of CDSC cultures to low mitogen medium induced the formation of multinucleated myotubes and expression of myogenic differentiation markers including MyHC (red) (FIG. 27G-I) and myogenin (red) (FIG. 27J-L). Sustained expression of Pax7 (red) (M-O) in differentiating cultures did not interfere with their differentiation. DAPI staining (blue) was used to visualize all nuclei.

Figure 28:
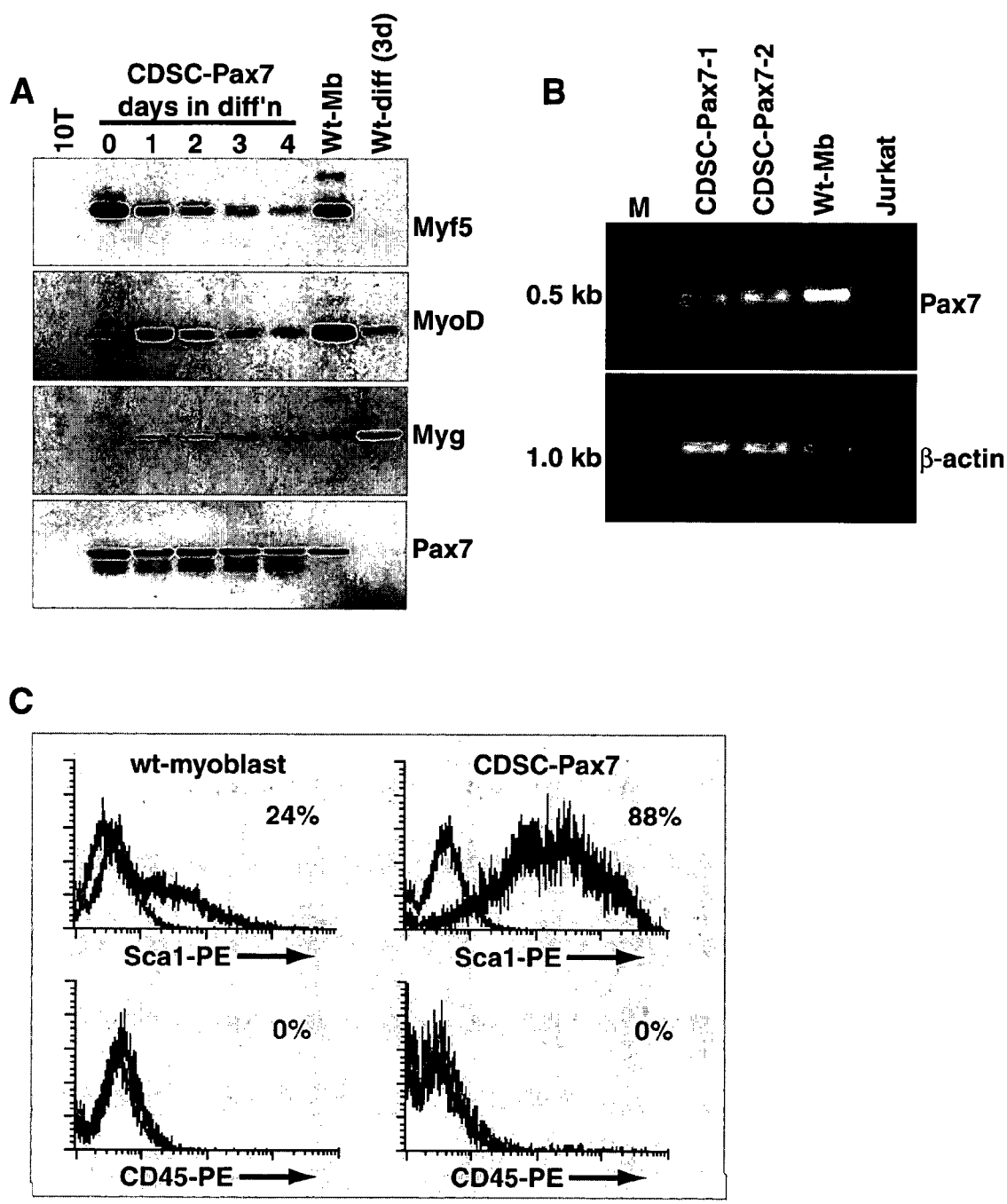

FIG. 28 shows results that CDSC-Pax7 cells express high levels of Myf5 and Sca1 (FIG. 28A) Western blot analysis of CDSC-Pax7 cells in proliferation conditions (day 0) and during differentiation (days 1-4) revealed high levels of Myf5 expression and low levels of MyoD expression. By contrast, satellite cell derived myoblasts (Wt-Mb) display the opposite profile of Myf5 and MyoD expression. Myogenin (Myg) was upregulated during the differentiation of CDSC-Pax7 and satellite cell-derived myoblasts (Wt-diff). Note the sustained expression of Pax7 during the differentiation of CDSC-Pax7 cells. C3H10T1/2 (10T) lysate was used as a negative control. (FIG. 28B) RT-PCR analysis indicated that CDSCPax7 cells (2 different lines) upregulated the endogenous Pax7 mRNA. Satellite cell derived myoblasts (Wt-Mb) and Jurkat cells were used as positive and negative controls respectively. (FIG. 28C) Flow cytometry indicated that CDSC-Pax7 cells lost expression of CD45 but retained high levels of Sca1. About 24% of satellite cell derived myoblasts (wt-myoblasts) expressed low levels of Sca1. (Black graph depicts staining with IgG-PE control antibody;

Red graph shows target staining using Sca1-PE or CD45-PE).

Figure 29:
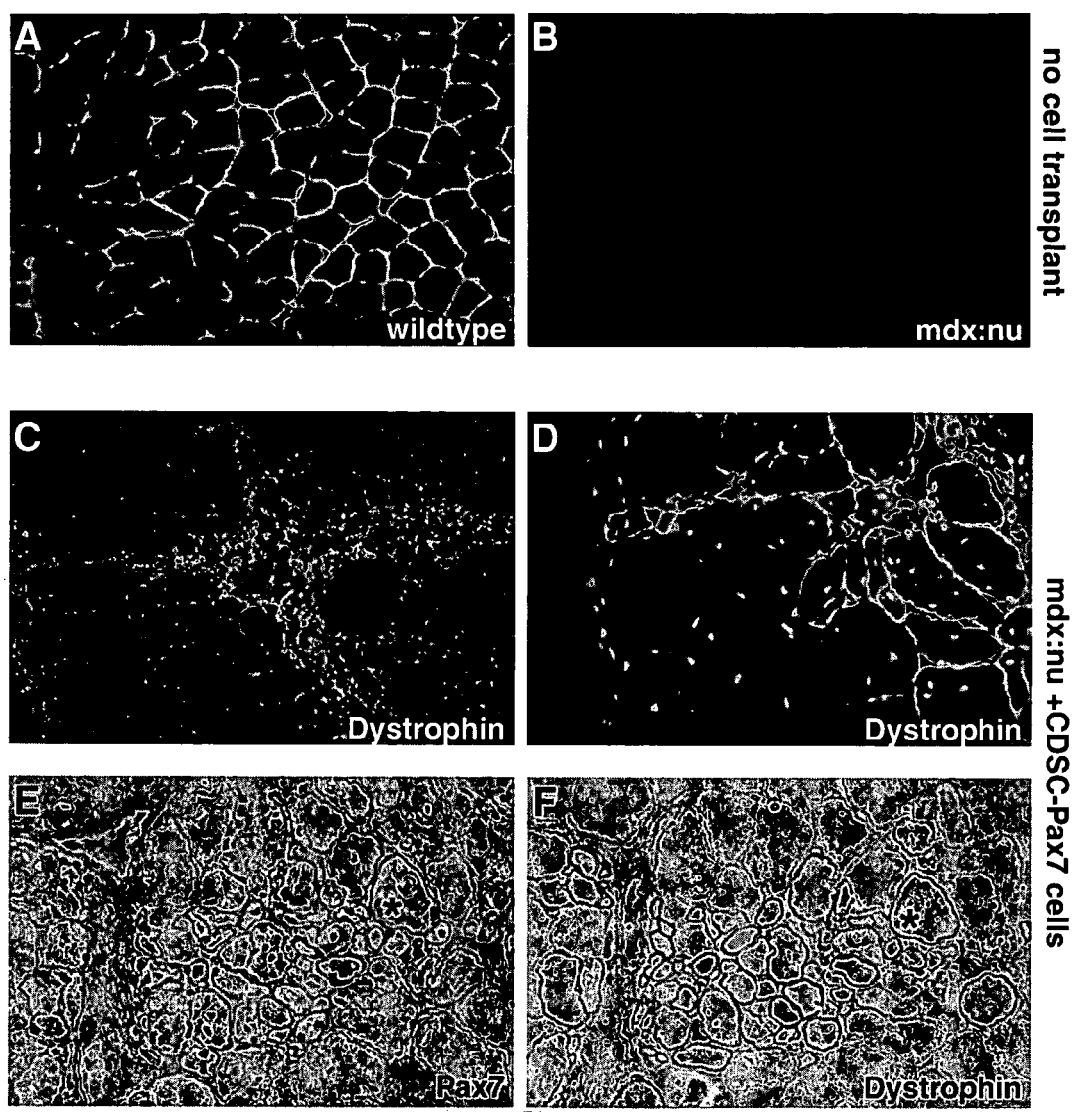

FIG. 29 shows results that CDSC-Pax7 cells efficiently contribute to the repair of dystrophic muscle. (FIG. 29A) Wild-type muscle expressed dystrophin at the plasmalemma of all myofibers. (FIG. 29B) Dystrophin protein was not detected in muscle sections from dystrophin-deficient mdx: nude mice (mdx:nu). (FIG. 29C-F) CDSC-Pax7 cells differentiated in vivo after transplantation, readily forming large numbers of dystrophin expressing myofibers (green) in mdx:nude muscle (FIG. 29C,D). Serial cross-sections showing the viral expression of Pax7 protein in central nuclei of regenerated fibers (FIG. 29E, red staining) confirmed the donor origin of dystrophin-positive myofibers (FIG. 29F, red staining).

Figure 30:
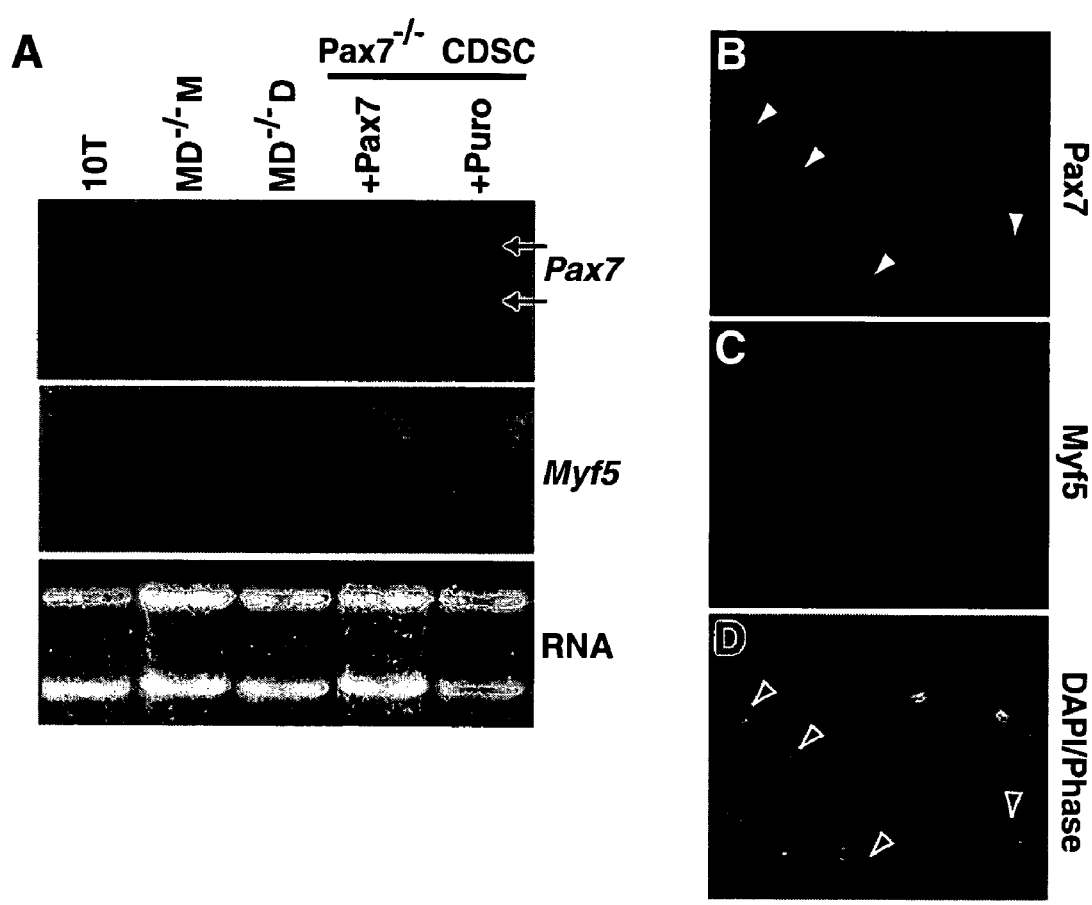

FIG. 30 shows results that Pax7 does not induce myogenesis in CD45+:Sca1+ cells from Pax7−/− muscle (FIG. 30A) Northern analysis shows that MyoD−/− satellite cell derived myoblasts (MD−/−M) and differentiating cells (MD−/−D) express endogenous Pax7 (upper arrow, Pax7 blot) and Myf5 transcripts. Pax7−/− CD45+:Sca1+ cells (CDSC) transduced with HAN-Pax7 (+Pax7) or HAN-puro (+puro) did not initiate expression of Myf5 mRNA. The retroviral transcript producing Pax7 (lower arrow) is smaller than the endogenous Pax7 mRNA (e.g. lower arrow). (FIG. 30B-D) Ectopic expression of Pax7 (red) (FIG. 30B) in Pax7−/− CDSC cells did not induce Myf5 protein expression (FIG. 30C). DAPI staining (blue) was used to visualize nuclei (D).

Figure 31:
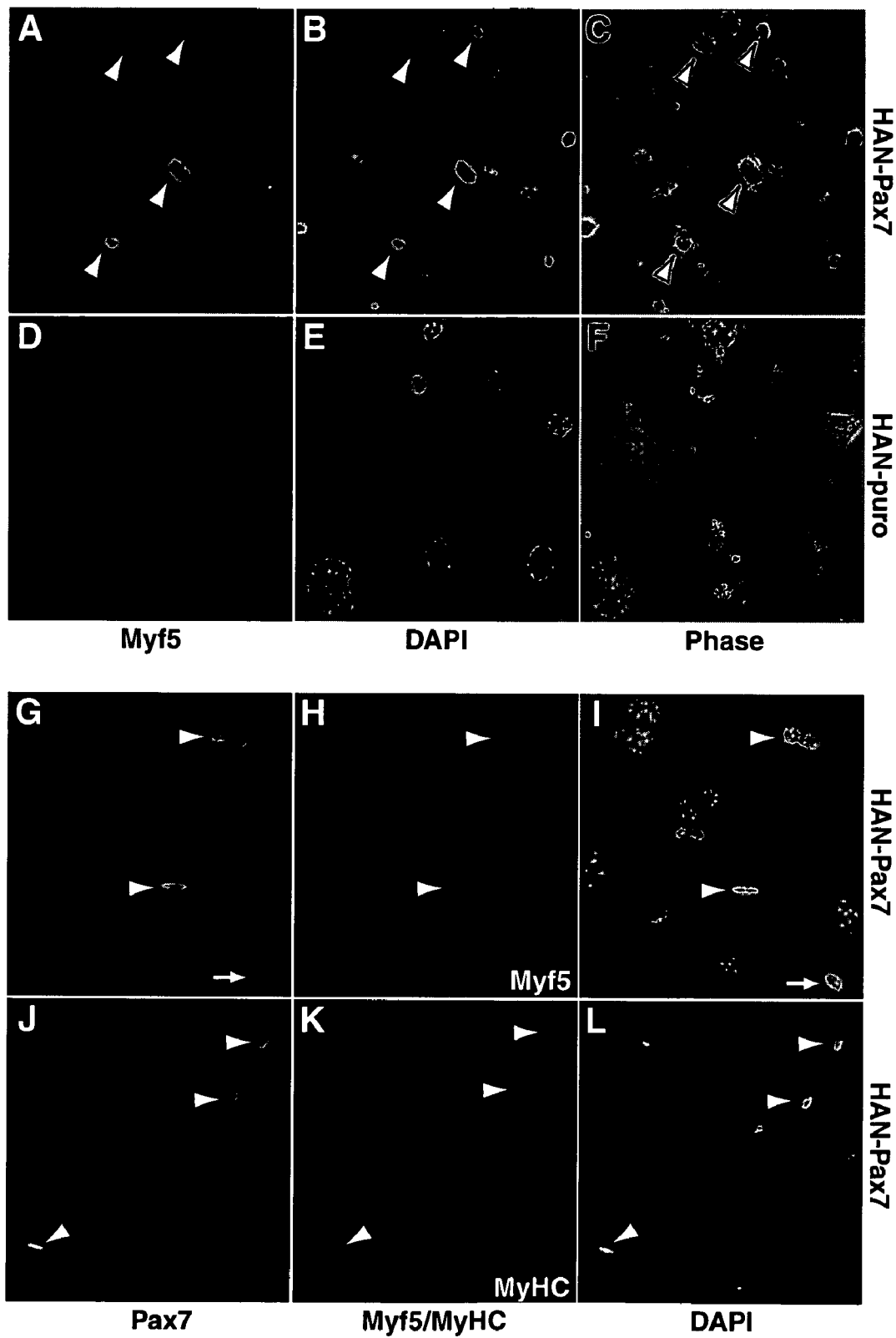

FIG. 31 shows results that Pax7 promotes myogenesis in CD45−:Sca1− cells from Pax7−/− muscle (FIG. 31A-C) Ectopic expression of Pax7 (HAN-Pax7) induced Myf5 expression (green) and myogenic commitment in CD45−: Sca1− cells from Pax7−/− muscle. (D-F) By contrast, Myf5 expressing cells were completely absent from HAN-puro infected cultures after selection. (FIG. 31 G-L) CD45−: Sca1− cells from Pax7−/− muscle expressed Myf5 (red) (FIG. 31 H) and MyHC (red) (FIG. 31K) only in cells that also coexpressed high levels of Pax7 protein (FIG. 31G,J).

Arrowheads indicate cells coexpressing Pax7 and Myf5/MyHC. Arrow in FIG. 31G,I depicts a Pax7+, Myf5− cell.

Figure 32:
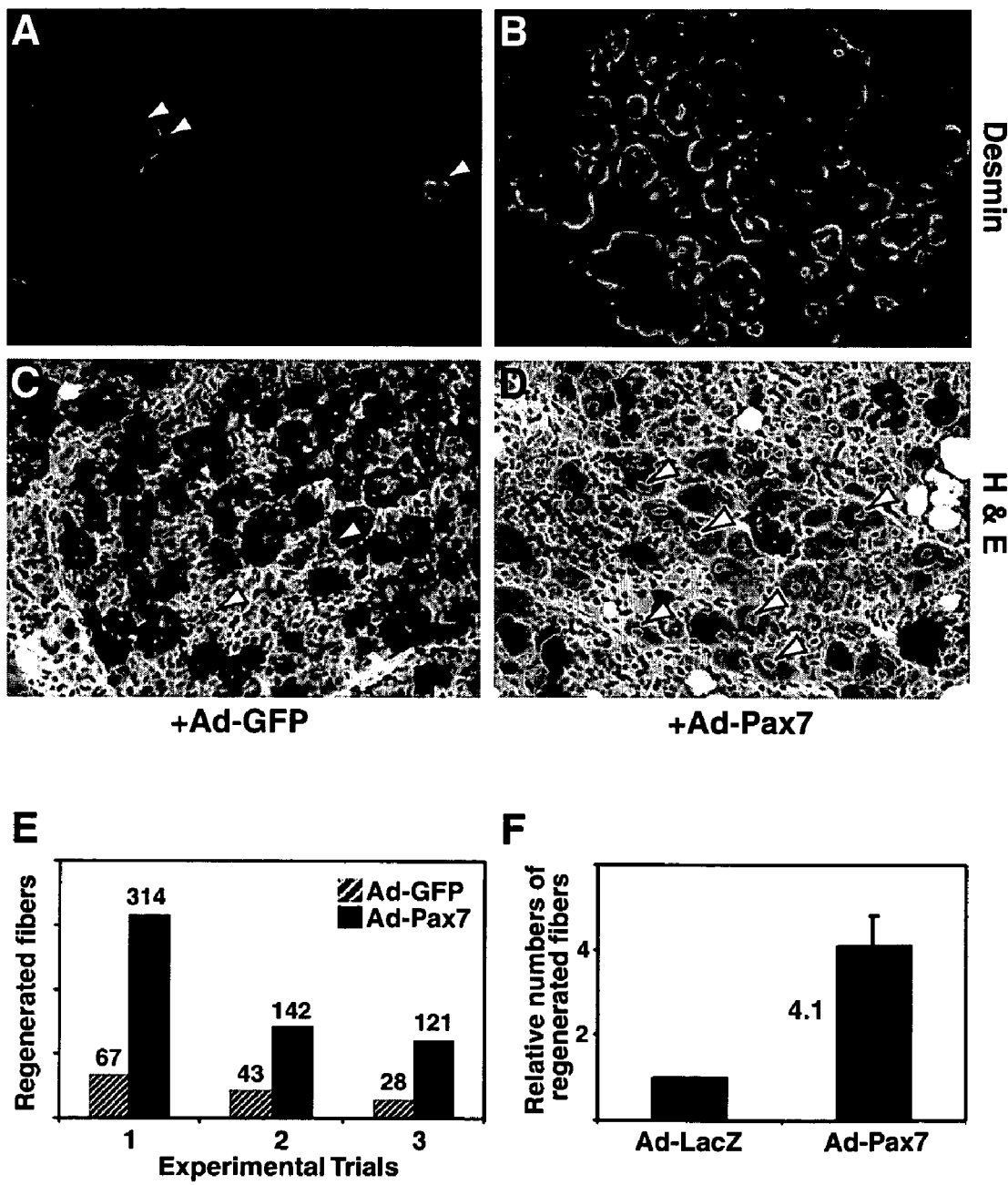

FIG. 32 shows results that Adenovirus-Pax7 significantly improves regeneration in vivo (FIG. 32A-B) Infection of cardiotoxin damaged Pax7−/− muscles with Ad-Pax7 resulted in markedly improved muscle integrity and a significantly increased number of Desmin immunoreactive (green) regenerated fibers (FIG. 32B) relative to muscles treated with Ad-LacZ. (FIG. 32C-D) Haematoxylin & Eosin staining similarly showed an increased number of centrally nucleated fibers in Ad-Pax7 treated Pax7−/− muscles. (FIG. 32E) In three separate experimental trials, the number of regenerated fibers was markedly increased in Ad-Pax7 treated muscles relative to Ad-puro, however the response was biologically variable between groups. On average, Ad-Pax7 infection resulted in a 4.1±0.72 fold increase in regenerated Pax 7−/− myofibers (FIG. 32F).

DESCRIPTION OF PREFERRED EMBODIMENT

The following description is of a preferred embodiment by way of example only and without limitation to the combination of features necessary for carrying the invention into effect.

The above description is not intended to limit the claimed invention in any manner. Furthermore, the discussed combination of features might not be absolutely necessary for the inventive solution.

Unless defined otherwise, all technical and scientific terms used herein have the same meaning as commonly understood by one of ordinary skill in the art to which this invention belongs.

Characterisation and Preparation of Pax-Encoding Vectors

One embodiment of the present invention provides a vector comprising an expressible sequence encoding Pax7, Pax3 or an active variant or fragment thereof.

Gene sequences encoding Pax7 and Pax3 are known and a worker skilled in the art would readily appreciate that these sequences can be obtained from publicly available databases, for example, GenBank. For example, NCBI Accession number AL021528 provides the sequence of a human Pax7 gene. Provided herein are non-limiting examples of amino acid sequences that can be expressed by the Pax-encoding vectors ofthe present invention (see FIGS. 13 through 24).

Nucleic acids comprising a sequence that encodes Pax7, Pax3, or an active variant or fragment thereof can be cloned into a vector using standard techniques that are well known to workers skilled in the art. The Pax-encoding vectors of the present invention facilitate the expression of Pax7, Pax3 or an active variant or fragment thereof such that the expressed protein can induce differentiation of adult stem cells. A variety of vectors suitable for use in the preparation of the Pax-encoding vectors of the present invention are known in the art. These vectors must be replicable and viable in the stem cells to be differentiated. The vector used in the preparation of the Pax-encoding vector of the present invention may be, for example, in the form of chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies.

Viral based systems provide the advantage of being able to introduce relatively high levels of a heterologous nucleic acid into a variety of cells. Additionally, such viruses can introduce heterologous DNA into nondividing cells. Suitable viral vectors for preparation of the Pax-encoding vector of the present invention for use in mammalian cells are well known in the art. These viral vectors include, for example, Herpes simplex virus vectors (U.S. Pat. No. 5,501,979), Vaccinia virus vectors (U.S. Pat. No.5,506,138), Cytomegalovirus vectors (U.S. Pat. No.5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like.

In one embodiment of the present invention, adenovirus-Pax7 vectors are employed to induce specification of stem cells in culture. Any of the Pax-encoding vectors described herein may be employed to induce specification or differentiation of adult stem cells.

As used herein, "retroviral vector" refers to the well known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a virion in an appropriate packaging cell line (see, for example, U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the MMTV vectors (U.S. Pat. No. 5,646,013), described supra, and the like.

In the preparation of the Pax-encoding vectors of the present invention the nucleic acid sequence encoding the Pax protein is placed under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the Pax proteins.

In accordance with one embodiment of the present invention the Pax-encoding vectors may contain additional sequences that encode heterologous biologically active proteins and/or polypeptides. For example, a Pax-encoding vector of the present invention may additionally express a therapeutic protein, such as a growth or trophic factor (e. g., GDNF, neurturin, BDNF, bFGF, NT-3, TGF-P), a transcription factor (e. g., Nurr-1), or an immunosuppressant operably linked to a suitable promoter. The expression of such a therapeutic protein may be beneficial in order to enhance the survival of cell transplants or increase the therapeutic potential of the cells following transplant. For example, the vectors can be introduced into stem cells that are capable of differentiating as muscle cells prior to transplantation into Duchenne patients.

Isolation and Culture of Stem Cells

Methods of cell isolation and culture are described in numerous publications known to the art, for example "Culture of Animal Cells: A Manual of Basic Technique", 4th Ed. (R. I. Freshney, 2000), and "Current Protocols in Cell Biology" (Wiley & Sons (eds), 2000).

Useful naive stem cells include adult stem cells, which may be isolated from bone marrow using conventional methodologies, (see, for example, Faradji et al., (1988) Vox Sang., 55 (3): 133-138 or Broxmeyer et al., (1989) PNAS 86:3828-3832), as well as naive stem cells obtained from blood.

Mesenchymal stem cells (MSCs) are the formative blast or embryonic-like cells found in bone marrow, blood, dermis, and periosteum that are capable of differentiating into specific types of mesenchymal or connective tissues including adipose, osseous, cartilaginous, elastic, muscular, and fibrous connective tissues (U.S. Pat. No. 5,736,396). The specific differentiation pathway which these cells enter depends upon various influences from mechanical influences and/or endogenous bioactive factors, such as growth factors, cytokines, and/or local microenvironmental conditions established by host tissues. Although these cells are normally present at very low frequencies in bone marrow, a process for isolating, purifying, and mitotically expanding the population of these cells in tissue culture is reported in Caplan et al. U.S. Pat. Nos. 5,197,985 and 5,226,914 and 5,736,396. Factors which have myogenic inductive activity on human MSCs are present in several classes of molecules, especially cytidine analogs, such as 5-azacytidine and 5-aza-2'-deoxycytidine. The effect of these modulating factors on human MSCs is disclosed in Caplan et al. U.S. Pat. No. 5,736,396.

Suitable solid tissue from which cells can be obtained includes any organ or tissue from adult mammalian tissue. Any mammalian tissue or organ can be used in this invention, including but not limited to those obtained from mice, cattle, sheep, goat, pigs, dogs, rats, rabbits, and primates (including human). Specific examples of suitable solid tissues include skeletal muscle, brain and central nervous system tissue from which neurons and other supporting cells are derived, skin derived from cultured keratinocytes, germ cells or embryonic stem cells or cells from other organs (liver, pancreas, spleen, kidney, thyroid, etc.). Stem cells and progenitor cells isolated from any other solid organ are also amenable candidates for culturing. Stem cells isolated from solid tissues (the exception to solid tissue is whole blood, including blood, plasma and bone marrow) which were previously unidentified in the literature are also within the scope of this invention.

In adult skeletal muscle, the progenitor cell is referred to as a satellite cell. Normally, satellite cells are dormant, but when muscle is traumatized, these cells divide and differentiate, to regenerate skeletal muscle. Methods of isolating, identifying, culturing and differentiating satellite cells are well known to those of skill in the art. For example, in U.S. Pat. No. 5,328,695, (1994) Lucas et al. describe a myogenic protein isolate from mammalian (chick) bone that stimulates lineage commitment and differentiation of skeletal muscle stem cells.

It is understood that the initial medium for isolating stem cells/progenitors, the medium for proliferation of these cells, and the medium for differentiation of these cells can be the same or different. The medium can be supplemented with a variety of growth factors, cytokines, serum, etc. As a general principle, when the goal of culturing is to keep cells dividing, serum is added to the medium in relatively large quantities (10-20% by volume). Specific purified growth factors or cocktails of multiple growth factors can also be added or sometimes used in lieu of serum. As a general principle, when the goal of culturing is to reinforce differentiation, serum with its mitogens is generally limited (about 1-2% by volume). Specific factors or hormones that promote differentiation and/or promote cell cycle arrest can also be used.

Examples of suitable growth factors are basic fibroblast growth factor (bFGF), vascular endothelial growth factor (VEGF), epidermal growth factor (EGF), transforming growth factors (TGF.alpha. and TGF.beta.), platelet derived growth factors (PDGF's), hepatocyte growth factor (HGF), insulin-like growth factor (IGF), insulin, erythropoietin (EPO), and colony stimulating factor (CSF). Examples of suitable hormone medium additives are estrogen, progesterone or glucocorticoids such as dexamethasone. Examples of cytokine medium additives are interferons, interleukins, or tumor necrosis factor-.alpha. (TNF-alpha).

Following differentiation, the specific differentiated cell types are identified by a variety of means including fluorescence activated cell sorting (FACS), protein-conjugated magnetic bead separation, morphologic criteria, specific gene expression patterns (using RT-PCR), or specific antibody staining. The gene products expressed between two or more given differentiated cell types will vary. For example, following differentiation of skeletal muscle satellite cells, the transcription factors Myf5, MyoD, Myogenin, and MRF4 are expressed. It is understood that developmental pathways often involve more than one step or stage for differentiation and any of these steps or stages may be affected by variations in culture conditions.

Use of the Pax-Encoding Vectors

One embodiment of the present invention provides a method of inducing myogenic differentiation of adult stem cells comprising the step of contacting the stem cells with the Pax-encoding vector under conditions that allow expression of the Pax protein, Pax7, Pax3 or an active variant or fragment thereof. This method optionally includes the step of first obtaining and culturing the stem cells from various sources as described herein.

In a related embodiment of the present invention the Pax-encoding vector is used in combination with one or more separate expression vectors that express a molecule that can, for example, aid in the induction of differentiation or improve the therapeutic potential of the myoblasts that are generated.

The differentiated cells that result from the method of the present invention have various uses, including but not limited to their use as a source material for transplantation in the treatment of muscle disease or disorder in animals, including humans. Additionally, the differentiated cells can be used as a research tool and as part of diagnostic assays.

The present invention further relates to a pharmaceutical composition comprising at least one myoblast prepared using the method of the present invention. According to one embodiment, said myoblast comprised in said pharmaceutical composition is encapsulated. Cell encapsulation methodology has been previously described which allows transplantation of encapsulated cells in treatment of Parkinson's disease (Tresco et al., 1992, ASAIO J. 38, 17-23) or Amyotrophic lateral sclerosis (Aebischer et al., 1996, Hum. Gene Ther. 7, 851-860). According to said specific embodiment, cells are encapsulated by compounds which form a microporous membrane, and said encapsulated cells can further be implanted in vivo. Capsules, for example approximately 1 cm in length containing the cells of interest may be prepared employing a hollow microporous membrane fabricated from poly-ether-sulfone (PES) (Akzo Nobel Faser AG, Wuppertal, Germany; D glon et al, 1996, Hum. Gene Ther. 7, 2135-2146). This membrane has a molecular weight cutoff greater than 1,000,000 Da, which permits free passage of proteins and nutrients between the capsule interior and exterior, while preventing the contact of transplanted cells with host cells. The entrapped cells may be implanted by intradermal, subdermal, intravenous, intramuscular, intranasal, intracerebral, intratracheal, intraarterial, intraperitoneal, intravesical, intrapleural, intracoronary or intratumoral routes.

In a further embodiment, the invention concerns the use of at least one myoblast cell generated, and eventually modified, as described above for the preparation of a composition for administration into a human tissue. In a preferred embodiment the prepared composition in accordance with the use claimed in the present invention is in a form for administration into a vertebrate tissue. These tissues include those of muscle, skin, nose, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc. The administration may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Moreover, myoblast cells are found to migrate from the original site of administration to other sites, particularly injured sites, e.g. degenerating foci. This migration phenomenom permits the treatment of injured sites by injecting myoblasts into the patient in need, particularly in tissue, usually muscle tissue, proximal to the injuries, although injection into the circulation or at a distal site may also be possible. By employing genetically engineered myoblasts one may provide for directed application of products of interest to the injured region. Usually, cell injection will be about $10^4$ to $10^7$ cells (modified or not) per $cm^3$ of muscle tissue (or higher if need be) to be treated. In this particular case, the composition according to the invention may also comprise a phrmaceutically acceptable injectable carrier. The carrier is preferably isotonic, hypotonic or weakly hypertonic and has a relatively low ionic strength, such as provided by a sucrose solution. It includes any relevant solvent, aqueous or partly aqueous liquid carrier comprising sterile, pyrogen-free water, dispersion media, coatings, and/or equivalents. The pH of the pharmaceutical preparation is suitably adjusted and buffered.

In a further aspect, the invention relates to a diagnostic kit comprising at least one myoblast cell generated according to the invention useful for in vitro assessment of muscular cellular toxicity or damages of candidate or commercially available pharmaceutical molecules (pre-clinical assays) or for in vitro screening of new drugs. In course of said applications, cell lines generated from Duchenne Muscular Dystrophy patient would be preferred. The cultured myoblasts may also serve as a tool to analyse physiopathology of muscular diseases.

Myoblasts prepared using the methods of the present invention can be used for delivery of a muscle protein to the circulation of a mammal. A muscle protein, as used herein, refers to a protein which, when defective or absent in a mammal, is responsible for a particular muscle disease or disorder. Muscle proteins include dystrophin, calpain-3, sarcoglycan complex members (e. g., α-sarcoglycan, P-sarcoglycan, γ-sarcoglycan and 5-sarcoglycan) and laminin alpha 2-chain. The term circulation is meant to refer to blood circulation. The term blood refers to the "circulating tissue" of the body, the fluid and its suspended formed elements that are circulated through the heart, arteries, capillaries and veins.

In the method for delivery of a muscle protein to the circulation of a mammal, an effective amount of purified donor myoblasts is transplanted into a mammal in need of such treatment (also referred to as a recipient or a recipient mammal). As used herein, "donor" refers to a mammal that is the natural source of the stem cells that are transformed using the viral vectors of the present invention into myoblasts. Preferably, the donor is a healthy mammal (e. g., a mammal that is not suffering from a muscle disease or disorder). In a particular embodiment, the donor and recipient are matched for immunocompatibility.

Preferably, the donor and the recipient are matched for their compatibility for the major histocompatibility complex (MHC) (human leukocyte antigen (HLA))-class I (e. g., loci A, B, C) and-class II (e. g., loci DR, DQ, DRW) antigens.

Immunocompatibility between donor and recipient are determined according to methods generally known in the art (see, e. g., Charron, D. J., Curr. Opin. Hematol., 3: 416-422 (1996); Goldman, J., Curr. Opin. Hematol., 5: 417-418 (1998); and Boisjoly, H. M. et al., Opthalmology, 93: 1290-1297 (1986)). In an embodiment of particular interest, the recipient is a human patient.

As used herein, muscle diseases and disorders include, but are not limited to, recessive or inherited myopathies, such as, but not limited to, muscular dystrophies.

Muscular dystrophies are genetic diseases characterized by progressive weakness and degeneration of the skeletal or voluntary muscles which control movement. The muscles of the heart and some other involuntary muscles are also affected in some forms of muscular dystrophy. The histologic picture shows variation in fiber size, muscle cell necrosis and regeneration, and often proliferation of connective and adipose tissue. Muscular dystrophies are described in the art and include Duchenne muscular dystrophy (DMD), Becker muscular dystrophy (BMD), myotonic dystrophy (also known as Steinert's disease), limb-girdle muscular dystrophies, facioscapulohumeral muscular dystrophy (FSH), congenital muscular dystrophies, oculopharyngeal muscular dystrophy (OPMD), distal muscular dystrophies and Emery-Dreifuss muscular dystrophy. See, e. g., Hoffman et al., N. Engl. J. Med., 318.1363-1368 (1988); Bonnemann, C. G. et al., Curr. Opin. Ped., 8: 569-582 (1996); Worton, R., Science, 270: 755-756 (1995); Funakoshi, M. et al., Neuromuscul. Disord., 9 (2): 108-114 (1999); Lim, L. E. and Campbell, K. P., Cure. Opin. Neurol., 11 (5): 443-452 (1998); Voit, T., Brain Dev., 20 (2): 65-74 (1998); Brown, R. H., Annu. Rev. Med., 48: 457-466 (1997); Fisher, J. and Upadhyaya, M., Neuromuscul. Disord., 7 (1): 55-62 (1997).

Two major types of muscular dystrophy, DMD and BMD, are allelic, lethal degenerative muscle diseases. DMD results from mutations in the dystrophin gene on the X-chromosome (Hoffman et al., N. Engl. J. Med., 318.1363-1368 (1988)), which usually result in the absence of dystrophin, a cytoskeletal protein in skeletal and cardiac muscle. BMD is the result of mutations in the same gene (Hoffman et al., N. Engl. J. Med., 318: 1363-1368 (1988)), but dystrophin is usually expressed in muscle but at a reduced level and/or as a shorter, internally deleted form, resulting in a milder phenotype.

Thus, the present invention also provides a method of treating a muscle disease or disorder in a mammal in need thereof comprising administering an effective amount of myoblasts to the mammal. In a particular embodiment, the invention relates to a method of treating a muscular dystrophy in a mammal in need thereof comprising administering an effective amount of myoblasts to the mammal. In another embodiment, the invention relates to a method of treating DMD in a mammal in need thereof comprising administering an effective amount of myoblasts to the mammal. In a third embodiment, the invention relates to a method of treating BMD in a mammal in need thereof comprising administering an effective amount of myoblasts to the mammal. In the latter two embodiments, a proportion of the administered myoblasts can fuse with DMD or BMD host muscle fibres, contributing dystrophin-competent myonuclei to the host fibres (mosaic fibres). The expression of normal dystrophin genes in such fibres can generate sufficient dystrophin in some segments to confer a normal phenotype to these muscle fibre segments.

The invention also relates to a method of treating a limb-girdle muscular dystrophy in a mammal in need thereof comprising administering an effective amount of myoblasts to the mammal.

Myoblasts prepared in accordance with the methods of the present invention can also be used in gene therapy, a utility enhanced by the ability of the myoblasts to proliferate and fuse. Myoblasts can be genetically altered by one of several means known in the art to comprise functional genes which may be defective or lacking in a mammal requiring such therapy. The recombinant myoblasts can then be transferred to a mammal, wherein they will multiply and fuse and, additionally, express recombinant genes. Using this technique, a missing or defective gene in a mammal's muscular system can be supplemented or replaced by infusion of genetically altered myoblasts. Gene therapy using myoblasts can also be applied in providing essential gene products through secretion from muscle tissue to the bloodstream (circulation), because myoblasts are capable of contributing progeny comprising recombinant genes to multiple, multinucleated myofibres during the course of normal muscular development.

According to an embodiment of the present invention, there is provided a stem cell transformed with a nucleotide sequence encoding Pax7, Pax3 or both. Preferably, the stem cell is a muscle-derived stem cell, more preferably a skeletal muscle stem cell. The stem cell may be derived from a subject at any time during development, for example, but not to be limiting, from neonate to adult or any time in between. In an embodiment, which is not meant to be limiting in any manner, the stem cell may be derived from a subject immediately after birth, or at about 1 day, 2 days, 5 days, 1 week, 5 weeks, 10 weeks, 25 weeks, 1 year, 2 years, 5 years, 10 years, 20 years, 40 years, 50 years, 60 years, 90 years, or any time therein between. Preferably the subject is living. However, it may be possible to obtain stem cells from subjects that are recently deceased.

In an alternate embodiment, which is not meant to be limiting in any manner, the stem cell may be an embryonic stem cell and thus may be defined specifically as such. Alternatively the stem cell is derived from a subject after birth, for example, but not limited to an adult stem cell. The stem cell preferably comprises CD45+ and Sca1+ cell surface proteins.

The stem cell may be derived from any appropriate subject, for example a mammalian subject, such as, but not limited to mice, cattle, sheep, goat, pigs, dogs, rats, rabbits, and primates (including humans). In an embodiment of the present invention, which is not meant to be limiting in any manner, the cell is a human cell.

The stem cells as defined above may exhibit one or more characteristics, or lack thereof, for example cell surface proteins or markers. In an embodiment of the present invention the cells exhibit CD45 and Sca1 ($CD45^+$:$Sca1^+$) cell surface markers. In an alternate embodiment, the cells are $CD45^-$:$Sca1^+$. Compositions comprising cells that exhibit both sets of markers as well as other markers and cell surface proteins are also contemplated.

The stem cell as defined above comprises a nucleotide sequence encoding Pax7, Pax3 or both. In an embodiment, the cell comprises a nucleotide sequence encoding Pax7. In an alternate embodiment, the nucleotide sequence encodes Pax3. In still an alternate embodiment, the stem cell comprises a nucleotide sequence encoding both Pax7 and Pax3.

As will be evident to a person of skill in the art, the nucleotide sequence may also comprise one or more regulatory sequences, for example promoters, terminators and the like. By the terms "regulatory sequence", "regulatory region", "regulatory element" it is meant a portion of nucleic acid typically, but not always, upstream of the protein coding region of a gene, which may be comprised of either DNA or RNA, or both DNA and RNA. When a regulatory region is active, and in operative association with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to a stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory sequence" "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within a subject as well.

The stem cell transformed with a nucleotide sequence encoding Pax7, Pax3 or both also may be transformed with a nucleotide sequence encoding one or more wild-type proteins, for example, but not limited to wild-type muscle proteins. By the term "wild-type protein" it is meant a protein that is normally found in nature, usually, but not always associated with a large percentage of subjects in a population. The wild-type protein typically is not defective in function in the subject and/or does not promote, cause or is associated with disease, for example a muscular degenerative disease in the subject. Preferably, the one or more wild-type proteins are wild-type proteins from the same species as the subject having the muscular degenerative disease.

In a further embodiment, the stem cell may be transformed with a nucleotide sequence encoding one or more wild-type variant proteins. The wild-type variant protein may differ in its amino acid sequence from that of the wild-type protein as usually found in nature, or in the population provided that the wild-type variant protein functions about normally in the subject and/or the protein does not promote, cause or is associated with a disease in the subject. Without wishing to be limiting in any manner, genetic polymorphisms giving rise to proteins that do not exhibit substantially altered function are meant to be encompassed in the stem cells and methods of the present invention as defined herein. Further, it is also contemplated that the wild-type variant protein may comprise a wild-type protein from a organism that is different from that of the subject, provided that the protein is capable of functioning normally in the subject and/or the protein does not promote, cause or is associated with a disease.

Representative examples of wild-type muscle proteins include, but are not limited to wild-type dystrophin, actin, myosin, calpain-3, sarcoglycan complex members (e.g., α-sarcoglycan, β-sarcoglycan, γ-sarcoglycan and 5-sarcoglycan), laminin, calcineurin, NFATc1, NFATc2, NFATc3, LGMD2H (TRIM32) and utrophin.

As provided above, the nucleotide sequence encoding Pax7, Pax3, or both may also encode the nucleotide sequence for the one or more wild-type proteins, one or more wild-type variant proteins, or a combination thereof. Alternatively, the nucleotide sequence encoding one or more wild-type proteins, one or more wild-type variant proteins, or combination thereof may be provided on a separate nucleotide sequence from that encoding Pax7, Pax3, or both. For example, but not to be limiting in any manner, a suitable stem cell may be transformed with a first nucleotide sequence encoding Pax7, Pax3, or both, and also transformed with a second nucleotide sequence encoding a suitable wild-type protein, for example, but not limited to, a suitable wild-type muscle protein. Also, it is contemplated that the cell may be transformed with a first nucleotide sequence encoding Pax7 and a second nucleotide sequence encoding Pax3. It is also contemplated that all nucleotide sequences may be cotransformed.

The nucleotide sequence or sequences encoding Pax7, Pax3, one or more wild-type proteins, one or more wild-type variant proteins are preferably integrated into the genome of the cell. However, the nucleotide sequence or sequences may remain extrachromosomal provided they are capable of being maintained by the cell.

The present invention further contemplates a composition comprising a stem cell as defined above and a pharmaceutically acceptable carrier. Preferably the stem cell is defined by one or more characteristics selected from the group consisting of:

a) adult stem cell;
b) skeletal muscles stem cells;
c) muscle satellite cell;
d) a side population cell;
e) $CD45^+:Sca1^+$ cell;
f) $CD45^-:Sca1^+$ cell, and;
g) Sca1+ cell.

The composition may comprise a plurality of cells including, but not limited to stem cells as defined above. Further, several different types of stem cells may be provided in the composition. For example, but not to be considered limiting in any manner, the composition may comprise $CD45^{+:Sca}1^+$ cells and $CD45^-:Sca1^+$ cells.

Any acceptable carrier may be employed in the compositions of the present invention. For example, but not to be considered limiting in any manner, the carrier may comprise growth medium, culture medium, storage medium, for example, but not limited to cryopreservation medium, pharmaceutically acceptable carriers or diluents or any combination thereof. Media may comprise a variety of components, for example, but not limited to serum, vitamins, sugars, salts and the like. The media may also comprise antioxidants, antibiotics, glycerol, DMSO, or other components as would be known to a person of skill in the art. Preferably, the acceptable carrier is about isotonic for stem cells, as would be known by a person of skill in the art.

The present invention also contemplates a kit comprising one or more stem cells as defined above. The kit may further comprise one or more acceptable carriers, devices for isolating stem cells from a subject, devices for delivering stem cells to a subject in need thereof, instructions for isolating, delivering, or modifying the cells or any combination thereof.

In an embodiment of the invention, which is not meant to be considered limiting in any manner, there is provided a method of treating skeletal muscle damage or deterioration in a subject comprising, administering stem cells or a composition comprising stem cells as defined previously to a subject. In a preferred embodiment, the stem cells comprise CD45$^+$:Sca1$^+$.

The skeletal muscle damage may be disease related or non-disease related. For example, but not wishing to be limiting in any manner, the stem cells may be employed to treat muscle wasting due to inactivity, for example, but not limited to after surgery or the like. Further, the stem cells may be employed for subjects that show muscle wasting and/or deterioration due to a disease, for example, but not limited to aids, cancer, or the like.

The present invention also contemplates methods and uses of stem cells as defined herein to increase a) the number of muscle cells in one or more muscles in a subject, b) the muscle mass of one or more muscles in a subject c) the strength of one or more muscles in a subject. In a preferred embodiment, the subject is a human. However, it is also contemplated that the stem cells may be employed to increase muscle mass in other subjects.

In an alternate embodiment of the present invention, which is not meant to be limiting in any manner, there is provided a method of treating a subject having a muscular degenerative disease comprising, administering stem cells, or a composition comprising stem cells as defined above to the subject having the muscular degenerative disease. In a preferred embodiment, the stem cells comprise CD45$^+$:Sca1$^+$ cells.

It is also contemplated that the one or more stem cells also may be transformed with a nucleotide construct producing one or more wild-type proteins, for example, but not limited to one or more wild-type muscle proteins. In this regard, the muscular degenerative disease may exist in the subject wholly or partially as a result of one or more genetic defects in the DNA of the subject, for example, but not limited to one or more mutations, deletions, inversions, insertions or a combination thereof in one or more promoters, regulatory sequences, genes encoding one or more protein products, or any combination thereof. In this manner, the stem cell may be capable of complementing the endogenous cells of the subject by providing one or more wild-type proteins that may be absent, under-produced, downregulated or mutated in the diseased subject.

In an embodiment of the present invention, there is provided a method of treating a first subject having a muscular degenerative disease comprising, a) isolating a plurality of muscle stem cells from a second subject lacking the muscular degenerative disease, the stem cells comprising CD45$^+$:Sca1$^+$ muscle stem cells;

b) transforming said cells with a nucleotide construct encoding Pax7, Pax3 or a combination thereof;

c) expressing Pax7, Pax3 or a combination thereof in the cells, and;

d) administering the cells to the first subject having the muscular degenerative disease.

In the embodiment wherein stem cells are isolated from a second subject lacking the muscular degenerative disease and administered to the first subject having the muscular degenerative disease, preferably the stem cells from the second subject are immunologically matched to the cells of the first subject. However, it is possible that the cells may be partially matched or unmatched. In such an embodiment, it may be preferable to administer a pharmaceutical agent that suppresses the immune system, for example, but not limited to cyclosporin or the like to prevent rejection of cells that are administered.

The method of the present invention may also comprise one or more purification steps to enrich for stem cells with one or more characteristics, for example, but not limited to, exhibiting one or more cell surface proteins. In an embodiment, the method may comprise one or more purification steps to enrich for CD45+:Sca1+ cells. The one or more purification steps may be performed after the step of isolating, transforming or both, or at any other time as required by a person of skill in the art. The one or more purification steps may comprise any purification step known in the art. In a preferred embodiment, the one or more purification steps comprises cell sorting by flow cytometry. Methods of sorting cells by flow cytometry are known in the art and may easily be practiced by a person of skill in the art.

The method of the present invention may also comprise a selection step to select for cells comprising Pax7, Pax3 or both, for example, after said cells are transformed. Any selecting step known in the art may be employed to select for cells transformed with Pax7, Pax3, or both Pax7, and Pax3, for example, but not limited to antibiotic resistance, etc. Similarly, the method of the present invention may comprise one or more selection steps after a stem cell is transformed with one more nucleotide sequences encoding one or more wild-type proteins.

The present invention also contemplates a method of treating a subject exhibiting a muscular degenerative disease caused by one or more genetic alterations in one or more genes of the subject comprising, a) isolating a plurality of muscle stem cells from said subject, the stem cells comprising CD45+:Sca1+ muscle stem cells;

b) transforming the cells with one or more nucleotide sequences, the one or more nucleotide sequences encoding
i) Pax7, Pax3 or a combination thereof, and;
ii) one or more wild-type proteins of said one or more genes;

c) expressing the Pax7, Pax3 or combination thereof and the one or more wild-type proteins in the cells, and;

d) administering the cells to the subject exhibiting the muscular degenerative disease.

The step of isolating may be performed as described herein or according to any appropriate method as known in the art.

In the step of administering the cells, the step may comprise administering between about $1\times10^3$ to about $1\times10^9$ cells, or an amount in between, for example, but not limited to about $1\times10^4$ cells, about $1\times10^5$ cells, about $1\times10^6$ cells, about $1\times10^7$ cells or about $1\times10^8$ cells. Further, the cells may be administered by injection directly into the bloodstream or they may be injected intramuscularly, subcutaneously, or intraperitonally. Preferably, the cells are injected in close proximity to the site where cells are needed by the subject. It is also contemplated that the cells may be injected in a single dose or in multiple doses over any suitable time period.

In an embodiment of the present invention it is also contemplated that one or more agents or stimuli may be provided to promote an increase in endogenous expression of Pax7, Pax3 or both in cells of a subject, preferably stem cells, more preferably CD45+:Sca1+ stem cells. The agent may comprise any component or combination of components that for example, promote wnt signalling or that upregulates endogenous Pax 7 expression. The agents may be delivered to cells of a subject in vitro or in vivo, for example in a suitable delivery vehicle.

The present invention also contemplates administering Pax7 protein, Pax3 protein, or both to a subject to promote myogenic specification of stem cells that are endogenous to the subject. The Pax protein(s) may be administered by any route known in the art. Preferably, the Pax protein (s) are injected in close proximity to muscle, preferably one or more skeletal muscles. However, it is also possible that the Pax proteins may be injected into the general circulation. In such embodiments, it is preferable that the Pax protein(s) are formulated into a suitable dosage form. Any suitable dosage form as known to a person of skill in the art may be employed. Thus, the present invention also contemplates compositions comprising Pax7 protein, Pax3 protein, or both and a suitable dosage form. The suitable dosage form may comprise one or more pharmaceutically acceptable carriers or excipients, for example, but not limited to, emulsions, surfactants, binding agents, hydrophilic phases, hydrophobic phases and the like.

Also provided by the present invention is a method of treating a subject exhibiting a muscular degenerative disease comprising, a) administering a composition comprising a vector, the vector comprising a nucleotide sequence encoding Pax7, Pax3 or a combination thereof to the subject, wherein said vector is capable of infecting one or more types of cells in said subject;

b) expressing the Pax7, Pax3, or combination thereof in said cells of said subject.

In an embodiment, which is not meant to be limiting in any manner, the vector is a viral vector, for example, a retroviral vector or an adenoviral vector. It is also contemplated that the viral vector may be an attenuated viral vector. Attenuated viral vectors and methods of attenuating viral vectors are known in the art, and any such method or vector may be employed herein, provided that the vector is capable of infecting at least one cell within the subject. Preferably the viral vector is non-pathogenic.

It is also contemplated that the vector may comprise a nucleotide sequence encoding one or more wild-type muscle proteins, wild-type variant muscle proteins, or a combination thereof. Also, the method may employ a single vector comprising one or more sequences or multiple vectors may be employed. Preferably, a single vector is employed.

The following passages provide results associated with tests of specific embodiments as described in the Examples. The results are not meant to limit the subject matter in any manner.

Pax7 is Required for Myogenic Commitment of CD45$^+$: Sca1$^+$ Cells

A unique subset of muscle stem cells comprising CD45$^+$: Sca1$^+$ cell surface proteins was isolated from wild-type, Pax7−/− and Pax7± subjects. The myogenic differentiation capacity of CD45$^+$:Sca1$^+$ cells from Pax7−/− muscle undergoing cardiotoxin-induced regeneration was examined. Flow cytometry analysis revealed a higher average proportion of CD45-expressing cells in Pax7$^{-/-}$ muscle relative to wild-type (FIG. 25A). Specifically, in muscle suspensions from Pax7$^{-/-}$ and wild-type littermates, 39±4% versus 31±9% of cells were CD45$^+$:Sca1$^-$ and 9±2% versus 5±2% of cells were CD45$^+$:Sca1$^+$ respectively (n 6). Four days following cardiotoxin injury, a significantly higher proportion of CD45+:Sca1+ cells (26±3% compared to 19±4% for Pax7−/− and wild-type respectively, p<0.05) and a reduced proportion of CD45−:Sca1+ cells were observed in Pax7−/− muscle (19±4% compared to 25±6% for Pax7−/− and wild-type respectively, p=0.07) (n=3) (FIG. 25A). By immunohistochemical analysis, Pax7 protein was upregulated in CD45+:Sca1+ cells from wild-type muscle 4 days after cardiotoxin injury (FIG. 25B,C). Endogenous Pax7 expression was not detected in CD45+:Sca1+ cells purified from uninjured muscles (Polesskaya et al., 2003). Furthermore, MyoD- (FIG. 25D,E) and Desmin-immunoreactive cells (FIG. 25F,G) were readily detected in cultured (18 hours in growth medium) CD45+:Sca1+ cells purified from regenerating Pax7± muscle (4 days post-ctx). Taken together, these results support a central role for Pax7 in the myogenic specification of CD45+:Sca1+ cells in response to acute muscle damage.

Pax7 is Sufficient to Induce Myogenesis in CD45+:Sca1+ cells

Adenoviral and retroviral expression systems were developed to ectopically introduce the Pax7 gene into putative adult stem cell populations. Pax7 was efficiently expressed from retrovirus (HAN-Pax7) in C3H10T1/2 fibroblasts and other cell cultures (FIG. 26A). Stable expression of Pax7 did not induce MyoD (not shown), Myf5 (not shown) or Myogenin protein expression (FIG. 26B,C) in C3H10T1/2 cells. MyoD, as expected, readily converted C3H10T1/2 cells into skeletal myocytes (FIG. 26D,E). These results suggest that Pax7 is not sufficient to induce myogenic determination in an established multipotent mesenchymal cell.

To determine whether Pax7 expression was sufficient to activate myogenesis in adult CD45+ progenitors, cells were fractionated from uninjured muscle and infected with Pax7-expressing retrovirus. CD45+:Sca1+ cells expressed Myf5 (not shown) and MyoD (FIG. 26F-I) protein only after infection with Pax7 (HAN-Pax7), and not with puromycin-alone control virus (HAN-puro), indicating that these cells undergo myogenesis in response to Pax7. Infection of CD45+:Sca1+ cells from Myf5nLacZ reporter mice with HAN-Pax7 retrovirus specifically induced Myf5nLacZ expression and myogenesis in infected cells (FIG. 26J). The Myf5nLacZ allele faithfully recapitulates the expression pattern of the endogenous Myf5 gene and is rapidly induced following myogenic commitment (Tajbakhsh et al., 1996; Tajbakhsh et al., 1997). Importantly, infection of CD45+: Sca1+ cells with control retrovirus expressing only a puromycin resistance gene (HAN-puro) did not activate Myf5nLacZ expression (FIG. 26K). Similar activation of Myf5nLacZ was observed in muscle side population (muSP) cells infected with Adenovirus-Pax7 but not Adenovirus-GFP (data not shown). Moreover, exposure of these cultures to differentiation conditions caused Pax7-expressing cells to differentiate into myotubes expressing Myosin Heavy Chain (MyHC) (FIG. 26L,M). Ectopic expression of Pax7 in CD45−:Sca1+ or CD45+:Sca1− cells did not result in the generation of myogenic cells. Taken together, these results demonstrate that Pax7 induces the myogenic program selectively in CD45+:Sca1+ adult stem cells from skeletal muscle.

Expression of Pax7 Converted CD45+:Sca1+ Cells into Myogenic Progenitors

CD45+:Sca1+ cells expressing retroviral Pax7 were stably selected using puromycin, hereafter called CDSC-Pax7 cells (n=4 independent isolates analyzed). CDSC-Pax7 cells displayed a stellate, fibroblastic morphology that was distinct from the round, refractile appearance of primary satellite cell-derived myoblasts. Proliferating CDSC-Pax7 cells expressed the myogenic determination bHLH factors, Myf5 (FIG. 27 A-C), and MyoD (FIG. 27D-F). CDSC-Pax7 cells cycled approximately 3 times faster than satellite cell derived myoblasts isolated simultaneously (not shown) and maintained their myogenic identity as primary cultures in excess of 3 months. CDSC-Pax7 cultures also differentiated efficiently into multinucleated myotubes expressing the terminal differentiation markers MyHC (FIG. 27G-I) and myogenin (FIG. 27J-L). These results demonstrate that the constitutive expression of Pax7 (FIG. 27M-O), which is normally downregulated during differentiation (Seale et al., 2000), did not interfere with cell-cycle arrest and normal myotube formation. By contrast, overexpression of Pax7 in C2C12 myoblasts prevented their differentiation into MyHC positive myocytes (data not shown). These experiments demonstrate that myoblasts derived from Pax7-induced CD45+:Sca1+ stem cells are amenable to in vivo and ex vivo expansion and subsequent terminal muscle differentiation. Thus, the present invention also contemplates a method of differentiating a stem cell into a multinucleated myotube comprising the step of transforming a stem cell with a nucleotide construct encoding Pax7, Pax3, or both and expressing the Pax protein in the cell.

CDSC-Pax7 Cells Express High Levels of Myf5 and Sca1

The expression pattern of myogenic factors in proliferating and differentiating CDSC-Pax7 cell lines was analyzed by Western blot (n=2). These experiments indicated that Myf5 was expressed at high levels in proliferating CDSC-Pax7 cells (FIG. 28A-day 0). Moreover, CDSC-Pax7 cells continued to express Myf5 protein during their differentiation. CDSC-Pax7 cells also expressed MyoD but at low levels relative to primary myoblasts. MyoD was transiently upregulated in CDSC-Pax7 cells as they entered their differentiation program (FIG. 28A-day 1, 2). The primary MRF expression profile in CDSC-Pax7 cells contrasted with the pattern observed in satellite cell-derived primary myoblasts (FIG. 28A-Wt-Mb). Primary myoblasts expressed higher levels of MyoD, lower levels of Myf5 and downregulated Myf5 immediately upon differentiation (Wt-diff). Myogenin (Myg) was upregulated during the differentiation of CDSC-Pax7 cells, albeit at lower levels compared with differentiating satellite cell-derived myoblasts (Wt-diff). CDSC-Pax7 cells also expressed endogenous Pax7 mRNA, suggesting that autoregulatory mechanisms may control Pax7 gene expression (FIG. 28B). Taken together, these analyses demonstrate that CDSC-Pax7 cells and primary satellite cell-derived myoblasts express different levels of MyoD and Myf5 but are similar in their ability to undergo terminal differentiation.

CDSC-Pax7 cells were originally derived from cells expressing cell surface CD45 and Sca1 proteins. Flow cytometry was employed to determine whether expression of these markers was maintained in vitro. This analysis demonstrated that CDSC-Pax7 cells continued to express high levels of Sca1 (about 90% of cells showed intense staining) but CD45 expression was extinguished (FIG. 28C). About 24% of primary satellite cell derived myoblasts displayed low levels of Sca1 staining. Sca1 levels were not increased in satellite cell-derived myoblasts overexpressing Pax7, suggesting that CDSC-Pax7 cells did not arise from a small number of committed myoblasts fractionated with CD45+:Sca1+ cells (not shown). Therefore, the present invention also contemplates stem cells transformed with a nucleotide sequence encoding Pax7, Pax3 or both that are further characterized as being CD45−:Sca1+.

CDSC-Pax7 Cells Differentiate In Vivo

To establish whether CDSC-Pax7 cells were capable of integrating and differentiating as myofibers in vivo, intramuscular transplantation studies were performed in dystrophic (dystrophin-deficient) muscle. Specifically, about $1 \times 10^5$ CDSC-Pax7 cells were injected into the tibialis anterior muscle (TA) of 4-6 week old mdx:nude mice. Mdx mice carry a point mutation in the dystophin gene and are a mouse model of Duchenne muscular dystrophy (Blaveri et al., 1999; Bulfield et al., 1984; Sicinski et al., 1989). As expected, dystrophin was localized at the myofiber sarcolemma in wild-type muscle (FIG. 29A) and was absent in mdx:nude skeletal muscle (FIG. 29B). Two months after transplantation, TA muscles were processed for immunohistochemical detection of dystrophin, and Pax7. These experiments revealed that CDSC-Pax7 cells differentiated in vivo, readily forming dystrophin-expressing myofibers in the dystrophin-deficient recipient muscle (FIG. 27C,D). Endogenous Pax7 protein expression was not observed in central nuclei within differentiated wild-type myofibers (data not shown). Therefore, the expression of Pax7 protein (from retrovirus or any other suitable source) in central nuclei within dystrophin+ fibers established a contribution of CDSC-Pax7 donor cells to recipient muscles (FIG. 25E,F). These results thus document the capacity for CDSC-Pax7 cells to differentiate in vivo and contribute to the repair of dystrophic muscle.

Pax7 Does Not Induce Myogenesis in CD45+:Sca1+ Cells from Pax7−/− Muscle

The myogenic differentiation of wild-type CD45+:Sca1+ muscle cells suggested that ectopic Pax7 would induce myogenesis in this cell population from Pax7−/− muscle. Infection of Pax7−/− CD45+:Sca1+ cells with Pax7 retrovirus resulted in high levels of retroviral Pax7 transcript but no expression of Myf5 mRNA by Northern blot hybridization (FIG. 30A) or RT-PCR (data not shown). The absence of Myf5 (FIG. 30B-D) or MyoD (not shown) expression by immunochemical staining of Pax7-transduced cells ruled out the possibility that a minor subpopulation of CD45+:Sca1+ cells underwent myogenesis. These experiments demonstrate that Pax7−/− CD45+:Sca1+ cells do not enter the myogenic lineage in response to Pax7, suggesting that intrinsic differences exist between wild-type and Pax7-deficient populations of CD45+:Sca1+ cells.

Pax7 Promotes Myogenic Commitment in Pax7-deficient CD45−:Sca1− Cells

In cell suspensions from uninjured muscle, satellite cells and their daughter myogenic precursors are uniformly CD45− and Sca1−. In Pax7−/− mice, the extremely rare myogenic cells in muscle tissue do not express CD45 or Sca1, and do not survive or expand in a variety of culture conditions. Ectopic expression of Pax7 in CD45−:Sca1− cells isolated from Pax7−/− muscle resulted in the expression of Myf5 protein in greater than about 50% of infected cells (n=3) (FIG. 31A-C). Analysis of HAN-puromycin infected control cultures did not reveal any myogenic cells (FIG. 31D-F). All Myf5-expressing myoblasts (FIG. 31G-I) and MyHC-expressing differentiated myotubes (FIG. 31J-L) in Pax7 infected CD45−:Sca1− cultures expressed viral-Pax7.

Adenoviral Expression of Pax7 Enhances Regeneration in Pax7-deficient Muscle

To investigate whether Pax7 was sufficient to stimulate myogenesis in vivo, adenovirus was used to ectopically express Pax7 in damaged Pax7−/− muscle. $1 \times 10^8$ adenoviral particles expressing either Pax7 (Ad-Pax7) or the bacterial β-galactosidase gene (LacZ) (Ad-LacZ) were injected directly into injured TA muscles of 4-6 week old Pax 7−/− animals 2 days after administration of ctx (n=3). Immunohistochemisty for Pax7 in adenovirus infected muscles demonstrated widespread Pax7 expression primarily in mononuclear cells within the damaged tissue (data not shown). To assess the effect of Pax7 expression in damaged tissue, TA muscles were analyzed and scored for regeneration 12 days after infection by enumerating the number of regenerated fibers with centrally located nuclei. The newly regenerated status of centrally nucleated fibers was confirmed by Desmin and embryonic MyHC immunoreactivity. Ad-Pax7 induced a markedly enhanced regenerative response relative to Ad-LacZ in Pax7−/− muscle as evidenced by the increased number of Desmin+ (FIG. 32A,B) and centrally nucleated fibers (FIG. 32C,D). Wild-type TA muscles typically contained in excess of 700 regenerated fibers 14 days after injury (not shown). In three independent experiments, cardiotoxin-damaged TA muscle from Pax7−/− mice typically contained an average of 46 surviving or regenerated fibers following regeneration (FIG. 32E). By contrast, infection of regenerating Pax7−/− TA with Ad-Pax7 resulted in the generation of an average of 192 myofibers (FIG. 32E). Therefore, Pax7 infected tissue contained about a 4.1±0.72 fold increase in the number of regenerated fibers (FIG. 32F). Together, these results demonstrate the ability of virally-transduced Pax7 to direct the de novo generation of myogenic progenitors capable of forming new myofibers and participating in regenerative myogenesis.

Without wishing to be bound by theory or limiting in any manner, the data contained herein suggests that stem cells may participate in regenerative myogenesis by forming myogenic progenitors following Pax7 induction in response to Wnt-signaling. The data additionally suggests that Pax7 may be a transcriptional target of the β-Catenin complex in Wnt-stimulated adult stem cells.

Again, without wishing to be bound by theory or limiting in nay manner, the dominant expression of Myf5 in Pax7 infected CD45+:Sca1+ cells (CDSCPax7) (FIG. 28A) suggests a paradigm wherein Pax7 preferentially activates Myf5 compared to MyoD. Interestingly, Pax3 has been implicated in myogenesis specifically upstream of MyoD (Tajbakhsh et al., 1997). Taken together, these observations suggest that Pax3 and Pax7 specify distinct myogenic lineages through the preferential activation of MyoD and Myf5 respectively.

Several experimental observations have noted a role for Myf5 in promoting myoblast proliferation. For example homozygous Myf5nLacZ, (e.g. Myf5-deficient) embryos display significantly reduced numbers of LacZ-expressing myogenic progenitors (Tajbakhsh et al., 1996). In avian embryos, Myf5 is preferentially expressed in proliferating myoblasts, whereas MyoD appears to be upregulated in differentiating cells (Delfini et al., 2000). Furthermore, Myf5−/− satellite cell-derived myoblasts display a profound proliferation deficit (Montarras et al., 2000). The increased growth rate of CDSC-Pax7 cells is similar to MyoD−/− myoblasts that also express elevated levels of Myf5 (Sabourin et al., 1999). Without wishing to be bound by theory or limiting in any manner, these observations suggest the possibility that Pax7 activates expression of Myf5 to promote adult myoblast expansion whereas Pax3 preferentially induces MyoD and differentiation.

Without wishing to be bound by theory, or limiting in any manner, the results as provided herein suggest that CD45+: Sca1+ cells give rise to satellite cells by a Pax7-dependent mechanism, possibly in response to Wnt signals.

The present invention also contemplates variations in the nucleotide sequence encoding Pax7, Pax3, or both and the corresponding protein sequences that do not substantially affect the activity of the protein(s). These variants of Pax also may be employed in the cells and methods as described herein.

The present invention will be further illustrated in the following examples. However it is to be understood that these examples are for illustrative purposes only, and should not be used to limit the scope of the present invention in any manner.

EXAMPLES

Molecular Cloning of Pax7 and Expression Analysis

RDA was performed as described by Hubank and Schatz, 1994. Satellite cell derived myoblast cDNA was subtracted twice against mouse embryonic fibroblast (MEF) cDNA (1:100; 1:400) and once against skeletal muscle cDNA (1:400) to generate the final difference products. The full-length mouse cDNA for Pax7 was isolated by screening an adult mouse skeletal muscle library (Clontech) using the RDA clone as a probe (Maniatis et al., 1982).

Total RNA was extracted as previously described (Chomczynski and Sacchi, 1987). Northern Analysis of 20 µg of total RNA from tissue or cell cultures was performed as per Maniatis et al., 1982. In situ hybridisation for Pax7 mRNA was performed as described elsewhere (Braissant and Wahli, 1998). Sections were counter-stained with 100 µg/mL Propidium Iodide (Sigma) in PBS for 10 minutes at room temperature. Three different Pax7 sequences from the full-length cDNA were used as cRNA probes: Pax7-Sal1: nts 150-1600; dp3-7 nts 4200-4700; Pax7-Cla1: nts 515-1500.

Myoblast and Stem Cell Culture

Primary muscle cultures were isolated as per Sabourin et al., 1999. Primary MEFs were isolated from 13.5-day-old Balb/c mouse embryos (Robertson, 1987). Single muscle fibers were isolated from hind limb skeletal muscles as described previously (Cornelison and Wold, 1997). Individual fibers were cultured in methocult GF M3434 containing 15% FBS,1% BSA, 10-4M 2-Mercaptoethanol, 10 µg/mL pancreatic insulin, 200 µg/mL Transferrin, 50 ng/mL SCF, 10 ng/mL IL-3, 10 ng/mL IL-6 and 3 units/mL EPO (Stem Cell Technologies) for 48 hr-10 days.

For hematopoietic colony forming assays, cell suspensions were derived from skeletal muscle by digestion with 0.4% collagenase Type A (Roche)/DMEM for 1.5 hr at 37° C., filtered (74 µm Costar Netwell) and resuspended at 100 cells/µl in 10% horse serum/DMEM. 10,000 cells were cultured in 3 mL of methocult (Stem Cell Technologies) for 14 days.

Fluorescence Activated Cell Sorting (FACS)

Hoechst staining and FACS analysis was essentially performed as described previously (Goodell et al., 1996). FACS was performed on a Becton-Dickinson FacStar flow cytometer equipped with dual lasers. Hoechst dye was excited at 350 nm and its fluorescence was measured at two wavelengths using a 424BP44 filter (Blue emission) and a 650LP filter (Red emission). A 640 DMSP mirror was used to separate wavelengths.

Immunocytochemistry and Electron Microscopy

Primary cell cultures or colonies picked from methocult medium were fixed and stained as described elsewhere (Sabourin et al., 1999) using anti-c-Met SP260 (Santa Cruz); anti-desmin DE-U-10 (DAKO), anti-mouse Ly-6G (clone RB6-8C5) (Pharmingen); anti-mouse Integrin$_{aM}$ (M1/70) (Pharmingen) and MF20 mAb (anti-Myosin Heavy Chain).

Gastrocnemius muscle was prepared for transmission electron microscopy by overnight fixation at 4° C. in 2% gluteraldehyde/0.1 M Cacodylate (pH 7.4) and processed using standard procedures as described elsewhere (Kablar, 1995). Randomly chosen fields were viewed with a Jeol 1200EX Biosystem TEM. Diaphragm and tibialis anterior muscles were prepared for HE staining as described elsewhere (Bancroft and Stevens, 1990).

Example I

Identification of Genes Expressed in Satellite Cell Derived Myoblasts

Muscle satellite cells represent a distinct lineage of myogenic progenitors responsible for the postnatal growth, repair and maintenance of skeletal muscle (reviewed by Seale and Rudnicki, 2000). At birth, satellite cells account for about 30% of sublaminar muscle nuclei in mice followed by a decrease to less than 5% in a 2 month old adult (Bischoff, 1994). This decline in satellite cell nuclei reflects the fusion of satellite cells during the postnatal growth of skeletal muscle (Gibson and Schultz, 1983). Satellite cells were originally defined on the basis of their unique position in mature skeletal muscle and are closely juxtaposed to the surface of myofibers such that the basal lamina surrounding the satellite cell and its associated myofiber is continuous (Bischoff, 1994).

In mice over 2 months of age, satellite cells in resting skeletal muscle are mitotically quiescent and are activated in response to diverse stimuli including stretching, exercise, injury, and electrical stimulation (Appell et al., 1988; Rosenblatt et al., 1994; Schultz et al., 1985; reviewed by Bischoff, 1994). The descendents of activated satellite cells, called myogenic precursor cells (mpc), undergo multiple rounds of cell division prior to fusion with new or existing myofibers. The total number of quiescent satellite cells in adult muscle remains constant over repeated cycles of degeneration and regeneration, suggesting that the steady state satellite cell population is maintained by self-renewal (Gibson and Schultz, 1983; Schultz and Jaryszak, 1985; Morlet et al., 1989). Therefore, satellite cells have been suggested to form a population of monopotential stem cells that are distinct from their daughter myogenic precursor cells as defined by biological and biochemical criteria (Bischoff, 1994; Grounds and Yablonka-Reuveni, 1993).

Satellite cells clearly represent the progenitors of the myogenic cells that give rise to the majority of the nuclei within adult skeletal muscle. However recent studies have identified a population of stem cells, also called sidepopulation (SP) cells in adult skeletal muscle. Muscle-derived SP cells are readily isolated by fluorescence activated cell sorting (FACS) on the basis of Hoechst dye exclusion (Gussoni et al., 1999; Jackson et al., 1999). Purified SP cells derived from muscle exhibit the capacity to differentiate into all major blood lineages following tail vein injection into lethally irradiated mice (Jackson et al., 1999). Of particular significance is the observation that transplanted SP cells isolated from bone marrow or muscle actively participate in myogenic regeneration. However only muscle-derived SP cells appear to give rise to myogenic satellite cells (Gussoni et al., 1999). In addition, SP cells convert to desmin-expressing myoblasts following exposure to appropriate cell culture conditions (Gussoni et al., 1999). However, whether SP cells are equivalent to satellite cells, are progenitors for satellite cells or alternatively represent an entirely independent cell population has remained unclear.

The gene expression profile of quiescent satellite cells and their activated progeny is largely unknown. Quiescent satellite cells express the c-met receptor (receptor for HGF) and M-cadherin protein (Cornelison and Wold, 1997; Irintchev et al., 1994). Activated satellite cells up regulate MyoD or Myf5 prior to entering S-phase (Cornelison and Wold, 1997). Proliferating myogenic precursor cells, the daughter cells of satellite cells, express desmin, Myf5, MyoD and other myoblast specific markers (Cornelison and Wold, 1997; George-Weinstein et al., 1993). Nevertheless, the paucity of cell-lineage specific markers has been a significant impediment to understanding the relationship between satellite cells and their progeny.

Based on our poor understanding of molecular events responsible for satellite cell development and activation, a PCR based subtractive hybridisation approach (Hubank and Schatz, 1994) was used to identify tissue-specific genes expressed in the satellite cell myogenic lineage. Results from this analysis identified several myoblast-specific genes potentially involved in satellite cell function. Pax7 was selected for further analysis based on the established role of the closely related Pax3 protein in regulating the developmental program of embryonic myoblasts (Tajbakhsh et al., 1997; Maroto et al., 1997).

To gain insight into the developmental program responsible for the differentiation and activation of skeletal muscle satellite cells, representational difference analysis of cDNAs (RDA) (Hubank and Schatz, 1994) was employed to identify genes expressed specifically in satellite cell derived myoblasts. This analysis resulted in the identification of 17 distinct products corresponding to 12 known and 5 potentially novel genes by searching GenBank (NCBI) using the FASTA program (unpublished). RDA clone dp3-7 encoded a fragment from within the Pax7 mRNA. Pax7 is a member of the paired-box family of transcription factors that play important regulatory roles in the development of diverse cell lineages (Mansouri, 1999). Therefore, a full-length 4.3-kb Pax7 cDNA was isolated from an adult mouse skeletal muscle cDNA library (Clontech) to facilitate further analyses (NCBI Accession Number: AF254422).

Example II

Pax7 is Specifically Expressed in Proliferating Myoblasts

Detailed expression analysis of the distribution of Pax7 MRNA was conducted by Northern analysis (FIG. 1). These analyses demonstrated that Pax7 was expressed exclusively in proliferating primary myoblasts, with comparable levels of expression in both wild-type and MyoD-/-cultures (FIG. 1A). However, Pax7 mRNA was down regulated following myogenic differentiation (FIG. 1A). Furthermore, Pax7 was not expressed at detectable levels in a variety of non-muscle cell lines (FIG. 1B). Rather, Pax7 was strictly expressed in myogenic cells including low levels in proliferating C2C12 mouse myoblasts, which are a continuous cell line originally derived from satellite cells (FIG. 1B). In addition, Pax7 mRNA was not detectable in 20 μg of total RNA from several adult mouse tissue samples (FIG. 1C). Analysis of polyA+ RNA from select mouse tissues revealed expression of Pax7 at low levels only in adult skeletal muscle (not shown). Therefore, in adult mice Pax7 expression appears specific to the satellite cell myogenic lineage.

Example III

Pax7 is Expressed in Satellite Cells

Figure 2:
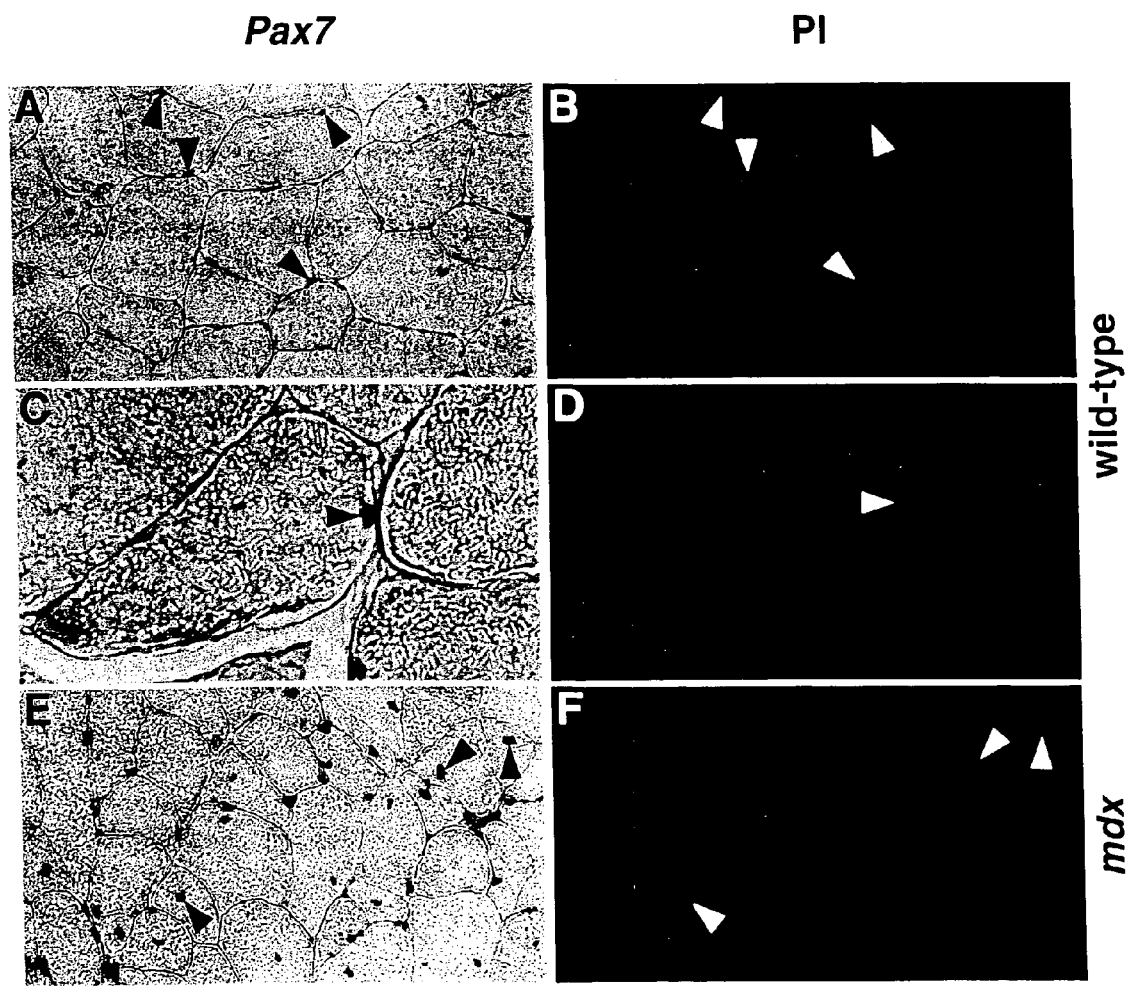
FIG. 2 shows the expression of Pax7 in muscle satellite cells. (A) In situ hybridisation revealed that Pax7 mRNA was expressed at a frequency and location consistent with specific expression in satellite cells and myogenic precursor cells. (B) Pax7 expression was associated with PI positive nuclei (40× magnification). (C,D) High magnification (200×) of a Pax7 expressing cell in wild-type muscle was characteristic of a satellite cell residing beneath the basal lamina. (E,F) Increased numbers of cells expressed Pax7 in regenerating mdx muscle (40×). Black and white arrowheads indicate cells stained positive for Pax7 mRNA, and PI positive nuclei respectively. (PI: propidium iodide).

To localise Pax7 mRNA in skeletal muscle, in situ hybridisation was performed on fresh frozen sections of tibialis anterior and gastrocnemius muscles from wild-type (Balb/c), MyoD−/−, mdx and compound mutant mdxMyoD−/−animals. Interestingly, Pax7 mRNA was associated with a subset of nuclei in discrete peripheral locations within undamaged wild-type (wt) (FIG. 2A,C) and MyoD−/− (not shown) skeletal muscle. Propidium-lodide (PI) staining was used to identify all nuclei within skeletal muscle thereby allowing for the enumeration of Pax7 positive cells (FIG. 2B,D,F). The in situ hybridization was repeated on muscle sections from three independent mice using three separate sequences as anti-sense cRNA probes to verify the expression patterns described. Approximately 5% of muscle nuclei (including satellite cell nuclei and myonuclei) were associated with Pax7 expression in adult wild-type muscle. By contrast, the number of Pax7 positive cells increased to 22% in MyoD−/− muscle. The increased expression of Pax7 in MyoD−/−muscle strongly supports the notion that Pax7 is expressed in satellite cells as previous work has revealed that MyoD-deficient muscle contains increased numbers of satellite cells (Megeney et al., 1996). At high magnification (200×), Pax7 appeared to be expressed in cells residing beneath the basal lamina of wild-type muscle fibers in positions characteristic for quiescent satellite cells (FIG. 2C).

To determine whether Pax7 was up regulated in regenerating skeletal muscle, 3-week-old mdx and compound mutant mdxMyoD−/− skeletal muscle was analyzed by in situ hybridization. Due to lack of dystrophin protein, mdx muscle undergoes repeated cycles of muscle degeneration and regeneration (Sicinski et al., 1989). As predicted, based on high levels of expression in cultured satellite cell derived myoblasts, Pax7 was widely expressed in regenerating areas of mdx and mdxMyoD−/− skeletal muscle (FIG. 2E). Centrally located nuclei within muscle fibers of mdx (FIG. 2E), MyoD−/− (not shown) and mdxMyoD−/− (not shown) muscle were also associated with Pax7 expression, suggesting that recently activated and fusing myogenic precursors express Pax7. Lastly, a similar distribution of immunoreactive nuclei was observed in muscle sections stained with anti-Pax7 antibody (Developmental Studies Hybridoma Bank). Taken together, the expression analysis supports the notion that Pax7 is expressed within the satellite cell lineage. Therefore, these results raise the hypothesis that Pax7 is required for the ontogeny or function of muscle satellite cells.

Example IV

Skeletal Muscle Deficiency in Pax7 Mutant Animals

Figure 3:
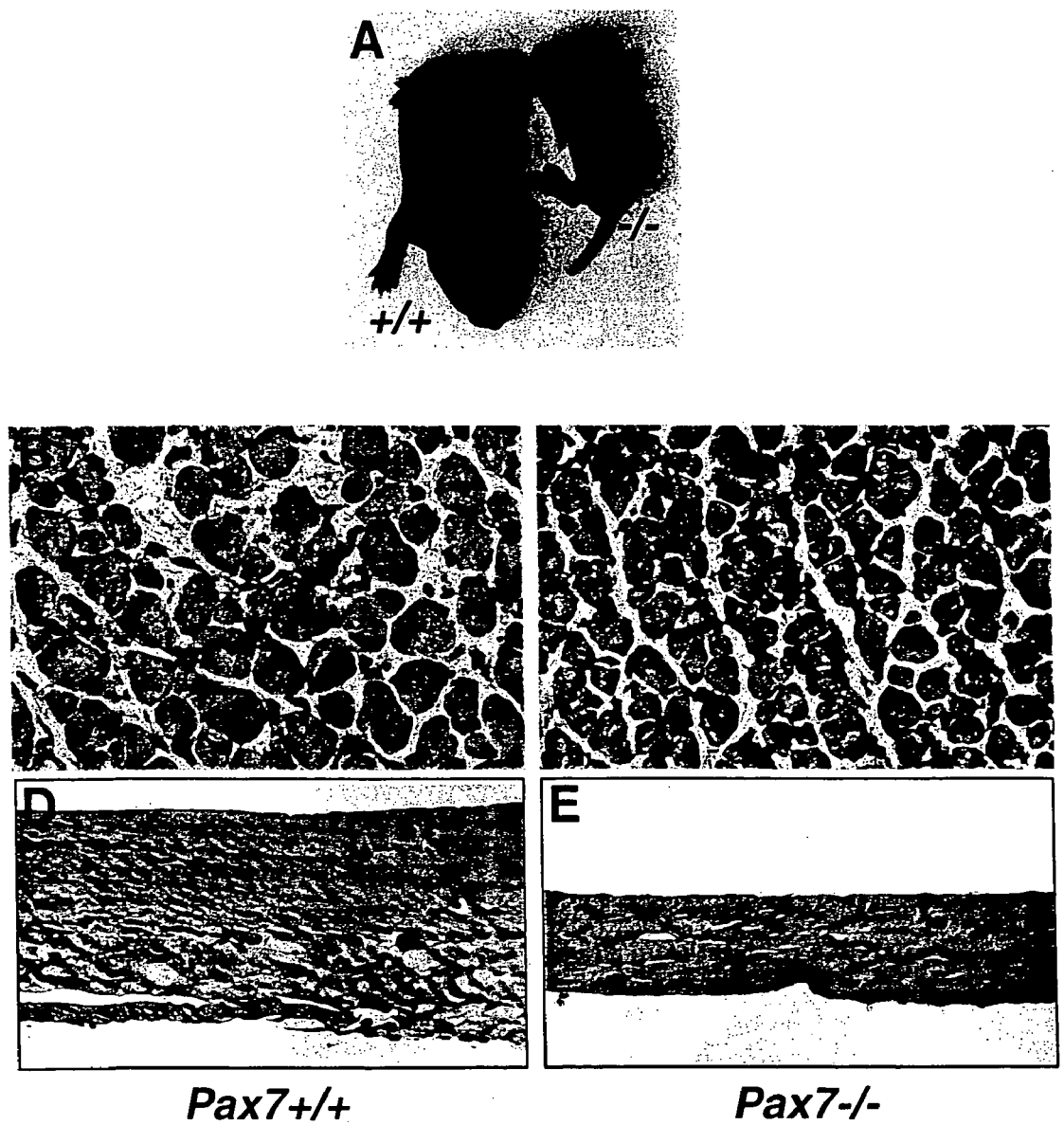
FIG. 3 shows that Pax7−/− mice exhibit skeletal muscle deficiencies. (A) Seven-day-old Pax7 mutant animals were approximately one-half the weight of wild-type animals and had splayed hind limbs and an abnormal gait. (B,C) Hematoxylin-Eosin (HE) stained tibialis anterior muscle sections (40×) revealed a normal histological appearance of (C) Pax7 mutant muscle but fibre diameter was reduced 1.5 fold as compared to (B) wild-type muscle. (D,E) The diaphragm of (E) mutant animals shown here in cross-section was significantly thinner than in (D) wild-type animals (40×).
Figure 4:
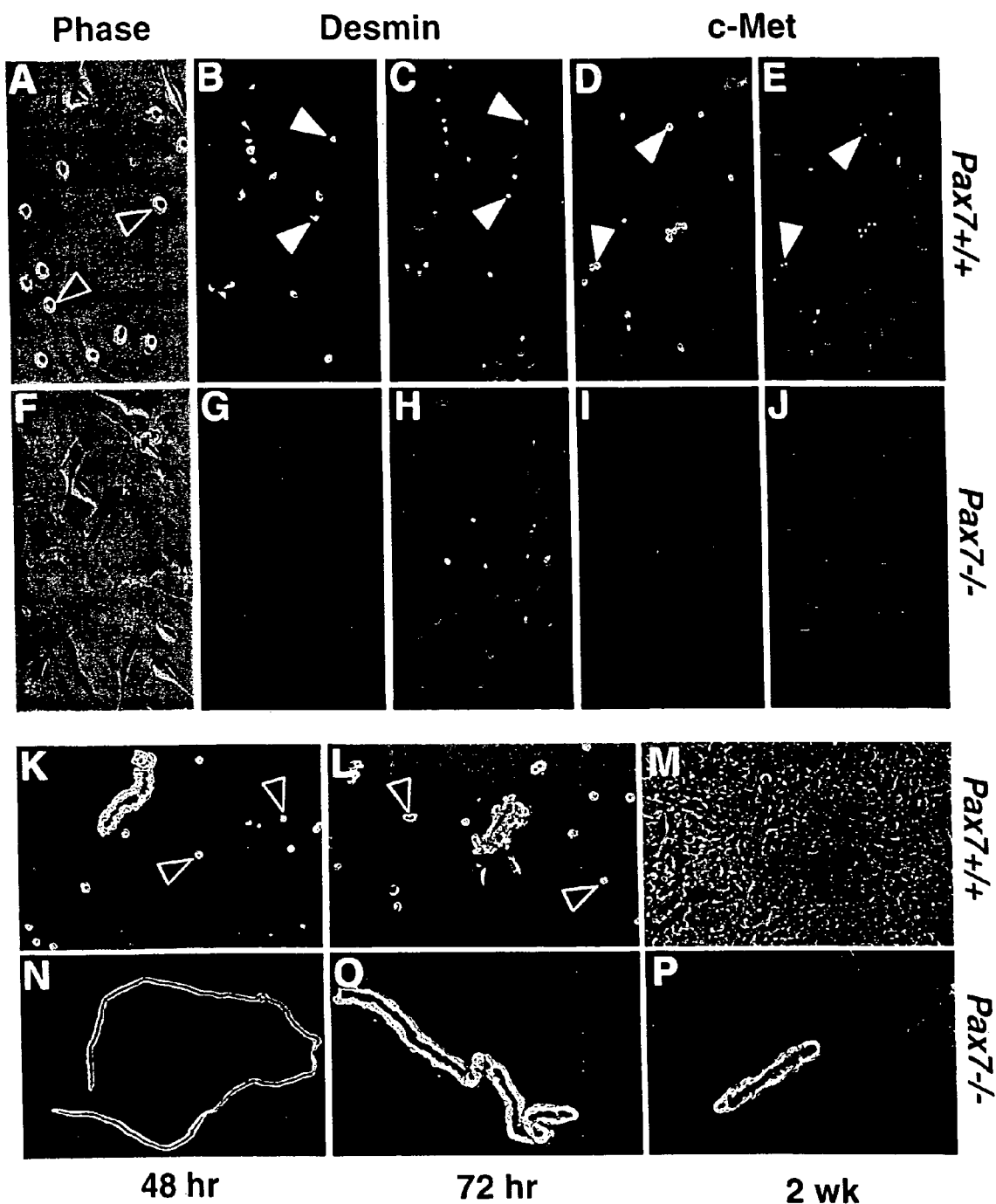
FIG. 4 shows the absence of myoblasts in cultures derived from Pax7−/− muscle. (A-J) Primary cell cultures were analysed by (A,F) phase microscopy; and
immunocytochemistry with (B,G) anti-desmin and (D,I) anti-c-Met antibodies. (C,E,H,J) Cells stained with antibodies were counter-stained with Hoechst 33342 to show all nuclei. Black arrowheads depict satellite cell derived myoblasts in (A). White arrowheads indicate immunoreactive cells and corresponding nuclei in (B-E).
Figure 5:
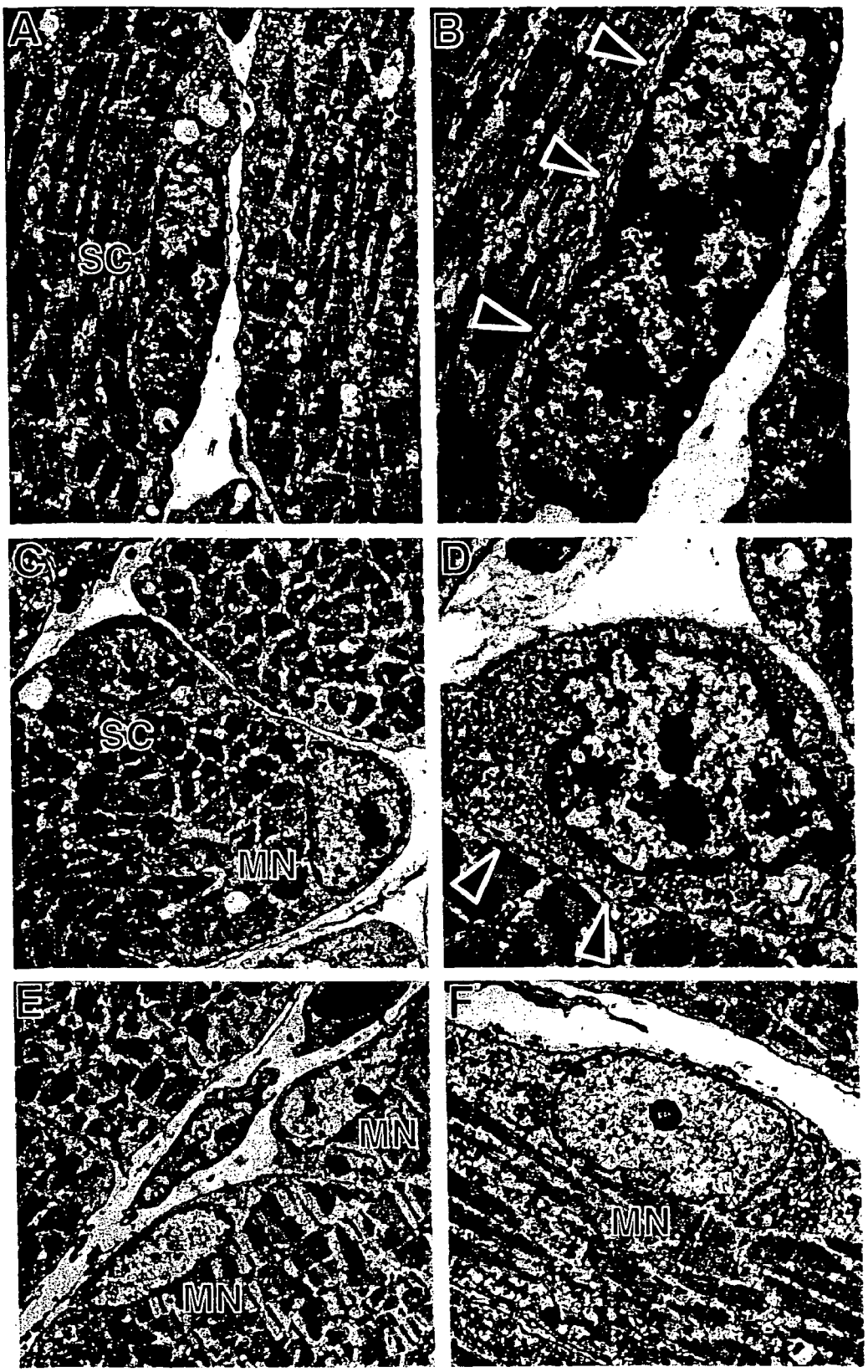
FIG. 5 shows the complete ablation of satellite cells in Pax7−/− muscle. (A-D) Transmission electron micrographs of 7-10 day old Pax7+/+ and (E,F) Pax7−/− muscle. (A,C) Satellite cells (SC) are readily identified in Pax7+/+ muscle (7500×). (B,D) High magnification of satellite cells clearly revealed the plasma membrane (black arrowheads) separating the satellite cell from its adjacent myofiber, the continuous basal lamina surrounding the satellite cell and myofiber and the heterochromatic appearance of the nucleus (20 000×). (E,F) Myonuclei (fiber nuclei) (MN) but not satellite cells were present in Pax7 mutant muscles. Other ultrastructural differences were not detected.

To evaluate possible roles for Pax7 in the formation or function of satellite cells, we examined skeletal muscle from mice carrying a targeted null mutation in Pax7 (Mansouri et al., 1996). Mice deficient for Pax7 express muscle-specific markers including MyoD and Myf5 in a normal spatial and temporal pattern within the developing myotome (Mansouri et al., 1996). However, Pax7−/− mice were significantly smaller than their wild-type and heterozygous counterparts (FIG. 3A). The body weight of Pax7−/− mice at 7 days of age was 50% reduced in comparison to wild-type littermates (N=20). This weight differential increased with age such that at two weeks of age, mutant animals were about 33% the weight of wild-type littermates. As previously reported, Pax7 mutant animals failed to thrive and usually died within two weeks after birth (Mansouri et al., 1996). In addition, we observed that mutant mice exhibited muscle weakness characterized by an abnormal gait and splayed hind limbs (not shown). Light microscopic analysis of hematoxylin-eosin (HE) stained lower hind limb skeletal muscle (below the knee) of one-week-old wild-type (FIG. 3B) and Pax7−/− (FIG. 3C) animals revealed a 1.5-fold reduced diameter of Pax7 mutant fibres (N=100 fibres). However, the overall organisation of muscle fibres was not affected. Moreover, the diaphragm from 7-day-old Pax 7−/− mice (FIG. 3E) was notably thinner than that from their wild-type littermates (FIG. 3D). Therefore, the markedly decreased muscle mass and reduced fibre calibre of Pax7 mutant muscle suggested that the postnatal growth phase of skeletal muscle normally mediated by satellite cells was deficient in the absence of Pax7.

Example V

Absence of Satellite Cell Derived Myoblasts from Pax7−/− Muscle

To gain insight into satellite cell function in Pax7 mutant mice, primary cells were cultured directly from the muscle of 7-10 day old wild-type mice and Pax7−/− littermates in five independent experiments. After two days in culture, many bursts of satellite cell derived myoblasts were readily identified in wild-type primary cultures based on morphological criteria (FIG. 4A) and immunocytochemistry using both anti-desmin and anti-c-Met antibodies that mark satellite cell derived myoblasts (FIG. 4B-E). Strikingly, no myoblasts were identified in mutant cultures, which instead were uniformly composed of fibroblasts and adipocytes as identified by morphological, and immunochemical criteria (FIG. 4F-J).

To further investigate whether myogenic cells were present in postnatal Pax7 mutant muscle, individual muscle fibres from 7-10 day old wild-type mice and Pax7−/− littermates were isolated in five independent experiments and cultured in methylcellulose stem-cell medium. Methylcellulose stem-cell medium readily promotes the activation, migration and proliferation of satellite cells associated with muscle fibres (Atsushi Asakura and Michael A. Rudnicki, unpublished observation). After 48 and 72 hours in culture, satellite cells associated with wild-type fibres generated distinct bursts of desmin-expressing myogenic cells. By contrast, Pax7 mutant muscle fibres did not give rise to any mononuclear cells. Following two weeks in culture, large colonies of fully contractile myosin heavy chain (MHC) expressing myotubes were present in cultures of wild-type but not Pax7−/− fibres (not shown). Therefore, these results suggest that satellite cells do not exist, or alternatively fail to proliferate in the absence of Pax7.

Example VI

Complete Ablation of Satellite Cells in Pax7−/− Muscle

To determine whether or not satellite cells were present in mutant animals, transmission electron microscopy (TEM) was used to analyse skeletal muscle from wild-type and Pax7−/− mice. Biopsies from gastrocnemius muscle of three 7-10 day old wild-type mice and mutant littermates were analysed by TEM. For each sample, 100 peripheral sublaminar nuclei were analyzed and identified as either satellite cell or myofiber nuclei. Criteria for the identification of satellite cells consisted of: a plasma membrane separating the satellite cell from its adjacent muscle fibre, an overlying basal lamina continuous with the satellite cell and associated fibre, and the characteristic heterochromatic appearance of the nucleus (reviewed in Bischoff, 1994).

Satellite cells were readily identified in wild-type muscle and comprised 25% of peripheral sublaminar nuclei (N=300) (FIG. 5A-D). By contrast, satellite cells could not be identified in over 300 sublaminar nuclei examined from mutant muscles (FIG. 5E,F). Furthermore, satellite cells were not found in muscle from E18 embryos (18 days post-coitum) (not shown). Therefore, in the absence of Pax7, complete ablation of muscle satellite cells was observed. The failure of muscle satellite cells to form in Pax7−/− muscle thus unequivocally establishes an essential role for Pax7 in the ontogeny of the satellite cell lineage.

Example VII

Muscle-Derived SP Cells are Present in Pax7 Mutant Muscle

To investigate the relationship between satellite cells and muscle-derived stem cells, fluorescence activated cell sorting (FACS) analysis of cells isolated from wild-type and Pax7−/− muscle was performed. Recent work has identified a population of stem cells (also called side-population (SP) cells) in skeletal muscle as defined by Hoechst 33342 dye exclusion (Gussoni et al., 1999; Jackson et al., 1999). Cell suspensions isolated directly from one-week-old skeletal muscle were stained with Hoechst dye in the presence or absence of verapamil. The SP cell population is sensitive to verapamil, which is thought to prevent dye efflux through the inhibition of mdr (multi-drug resistant)-like proteins (Goodell et al., 1996; Goodell et al., 1997). Based on results from three independent trials with six 7-10 day old Pax7−/− and wild-type animals, the proportion of muscle SP cells was unaffected by the absence of Pax7 (FIG. 6A-D). The relative proportion of SP cells in wild-type (1.8%) (FIG. 6A) versus Pax7 mutant muscle (1.5%) (FIG. 6C) did not differ significantly. Taken together, these data indicate that muscle satellite cells are either a population distinct from muscle SP cells, or alternatively represent only a small subpopulation of muscle SP cells.

Example VIII

Figure 6:
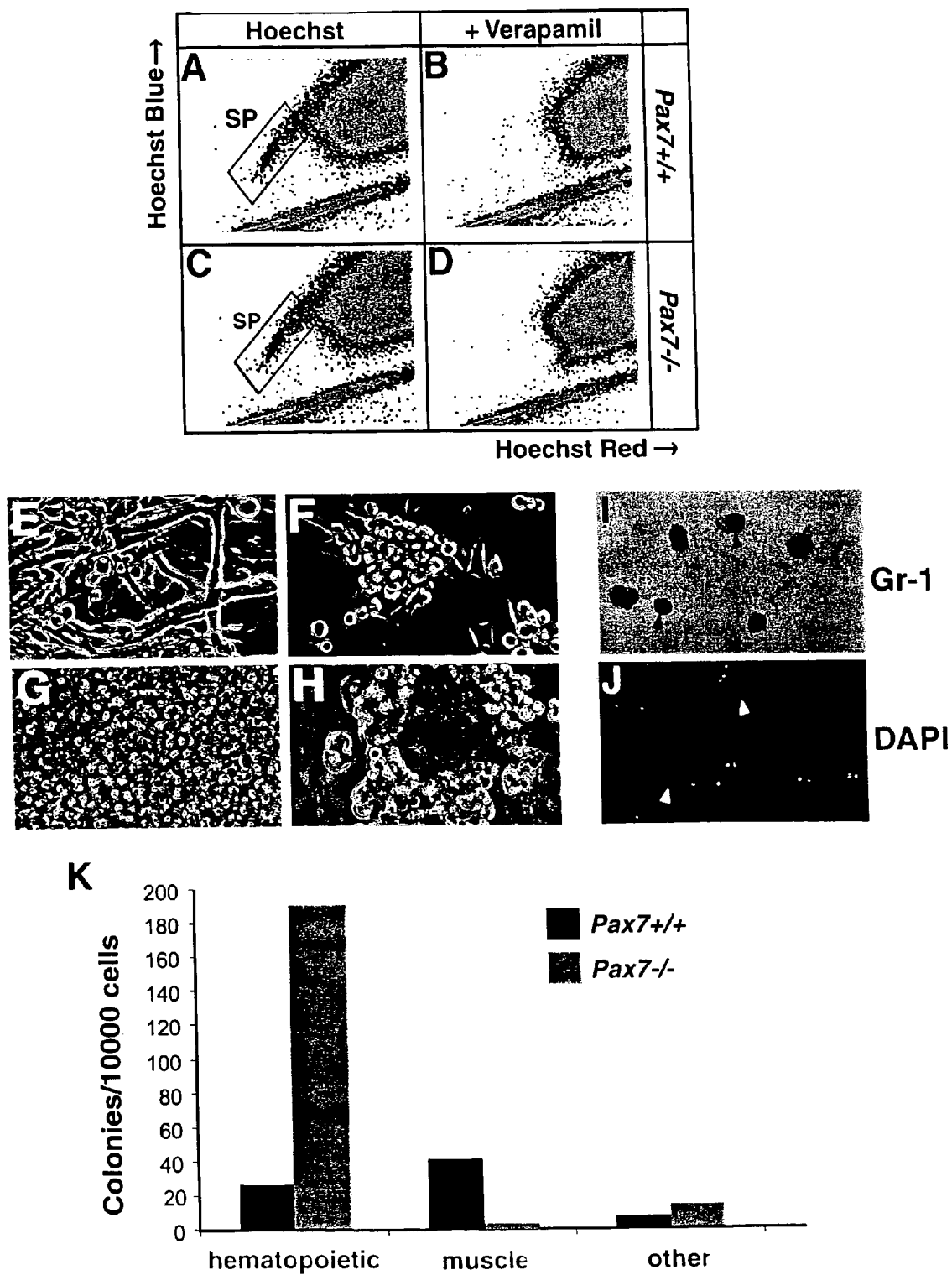
FIG. 6 shows the enhanced hematopoietic potential of Pax7−/− muscle-derived stem cells. (A-D) FACS analysis of Hoechst stained muscle-derived cells demonstrated approximately equal numbers of verapamil sensitive side-population (SP) cells in both (A,B) Pax7+/+ and (C,D) Pax7−/− muscles. (E) Myosin heavy chain positive muscle colonies predominate in stem cell medium/methylcellulose cultures of Pax7+/+ muscle cells. (F) Pax7−/− muscle cells have increased hematopoietic potential and generate granulocyte and monocyte colonies verified by (G,H) Ly-6G immunoreactivity. (I) Colony forming assay of muscle cells cultured in stem cell medium/methylcellulose over a period of two weeks demonstrated almost a 10-fold increased hematopoietic potential of Pax7 mutant stem cells. Other cells represent both fibroblasts and adipocytes.

Stem Cells Derived From Pax7−/− Exhibit Markedly Increased Hematopoietic Potential To characterise the differentiation potential of Pax7 deficient stem cells, dissociated muscle cells from 7-10 day old Pax7−/− and wild-type animals were assayed for colony formation in methylcellulose stem cell medium, which allows the growth of muscle as well as hematopoietic colonies (Atsushi Asakura and Michael A. Rudnicki, unpublished). Seven independent experiments were analysed in which 10,000 cells from both wild-type and Pax7−/− muscle were cultured. Hematopoietic colonies included granulocytic and monocytic cells and were present in both wild-type and mutant cultures based on immunoreactivity with Ly-6G (FIG. 6G,H) and Integrin$_{aM}$ chain (not shown). Ly-6G is a cell surface antigen, which is expressed exclusively in granulocyte and monocyte lineages (Fleming et al., 1993). Integrin$_{aM}$ chain, also known as MAC-1 is expressed in granulocytes, macrophages and Natural Killer Cells (Leenen et al., 1994). Wild-type cultures were predominantly composed of contractile muscle colonies reactive with antibody to Myosin Heavy Chain (FIG. 6E). By contrast, Pax7−/− cultures exhibited a markedly increased potential for hematopoietic differentiation (FIG. 6F) and generated about 10 times the number of hematopoietic colonies as compared to wild-type cultures (FIG. 6I). To rule out the possibility that the presence of differentiating muscle cells was inhibiting hematopoietic differentiation in wild-type cultures, mixed cultures of Pax7−/− and wild-type cells were analysed (not shown). Results from these experiments showed that hematopoietic colony formation was not adversely affected by differentiating myocytes.

Figure 7:
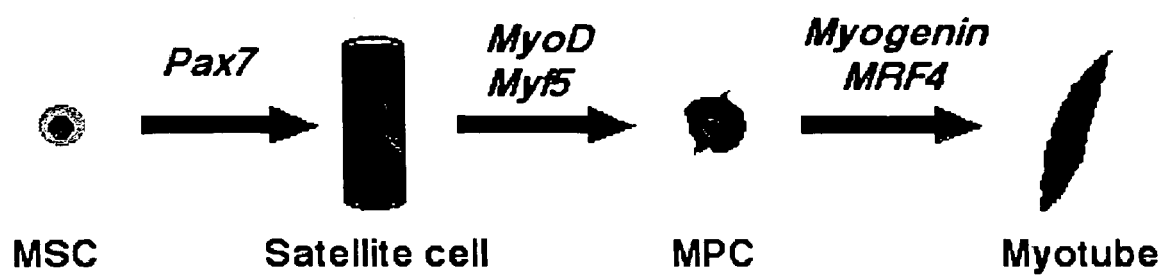
FIG. 7 shows a schematic representation of the role of Pax7 in the specification of satellite cells. Muscle-derived stem cells primarily give rise to myoblasts when cultured in stem cell medium. By contrast, Pax7−/− muscle stem cells exhibit almost a 10-fold increase in propensity towards hematopoietic differentiation and are incapable of forming adult myoblasts. These data therefore implicate Pax7 in regulating the specification of adult muscle satellite cells by restricting the fate of stem cells. Taken together, these experiments suggest the following hypothesis.

The colony forming assays summarised in FIG. 6I depict the average number of hematopoietic, skeletal myocyte and other (e.g. fibroblast, adipocyte) colonies from 7 independent isolations performed in triplicate. Therefore, stem cells isolated from muscle lacking Pax7 exhibited a strongly increased propensity towards hematopoietic differentiation and were incapable of forming adult myoblasts. Importantly, highly purified SP cells from wild-type muscle convert to myoblasts under the appropriate culture conditions (Gussoni et al., 1999). Taken together, these results suggest the hypothesis that induction of Pax7 in muscle-derived stem cells directs the specification of satellite cells through restriction of developmental potential (FIG. 7).

Example IX

Generation of Recombinant Adenovirus-Pax7

In order to demonstrate the ability of Pax7 to induce myogenic specification of muscle-derived stem cells, exogenous Pax7 was expressed in fractionated SP cells and muscle-derived cells using recombinant Adenovirus vectors. Adenovirus was selected as the vector for gene delivery in this application due to its transient high level expression in replicating cells (i.e. does not integrate into host cell genome), its ability to infect a wide range of cell types including quiescent cells and its potential to be grown to high titres, required for in vivo applications. For these experiments, the full-length coding sequence for Pax7 was cloned downstream of the murine CMV promoter in the adenoviral shuttle vector, pDC516 (Microbix) using EcoR1 and Sal1 restriction sites (FIG. 9). Recombinant, replication-defective adenovirus type 5 (E1 deficient) was generated by co-transfection of pDC516-Pax7 and the plasmid containing the adenoviral genome, PBHG□E1 into permissive 293 cells (Ng et al., 1999). Recombinant Ad-Pax7 viral plaques were picked and expanded by serial passages in 293 cells, which permits the growth and reproduction of virus. The structure of recombinant Ad-Pax7 virus was verified by restriction digest analysis. To confirm that Pax7 protein was appropriately expressed from the adenovirus, Ad-Pax7 and Ad-empty (i.e. no transgene) were used to infect C2C 12 myoblasts as well as 10T1/2 fibroblasts. Adherent cells were infected with crude viral preparations for 1 hour at room temperature. Expression of Pax7 in infected cells was assessed 1-day post infection by western blot analysis of cell lysates using an antibody reactive to Pax7 (Developmental Studies Hybridoma Bank) (FIG. 10). The results of western analysis indicate that Pax7 is expressed at relatively high levels in infected cells. High-titre viral stocks (~$10^{12}$ pfu/ml) were subsequently prepared and purified using cesium chloride gradients and dialysis against tissue-culture grade PBS.

Example X

Isolation and Infection of SP cells

Fluorescence activated cell sorting (FACS) was used to isolate SP cells from skeletal muscle of 2 month old wild-type mice. Hind limb muscles were dissected from bones and connective tissues and subsequently digested with 3% collagenase B (Roche)/2.4 U/ml dispase II (Roche) to disperse mononuclear cells. Cells were separated from undigested tissue, fibers and debris by filtration through 74 μm nytex filters (Costar). Suspensions were spun down and resuspended in muscle stem cell medium (Ham's F-10 nutrient mixture (Life Technologies); 20% FCS; 5% chicken embryo extract (Life Technologies)) and plated on plastic 10 cm tissue-culture dishes overnight (10-14 hours). The following day, adherent cells were collected by trypsinization and combined with suspension cells (i.e. non-adherent), spun-down and suspended in 2% FCS/DMEM at a concentration of $2\times10^6$ cells/ml. Hoechst 33342 staining was carried out as previously described (Goodell et al., 1996). Specifically, Hoechst 33342 (Sigma) was added to cell suspensions to a final concentration of 5 μg/ml with or without the addition of 50 μM verapamil (Sigma) and incubated for 90 min. at 37° C. Following Hoechst staining, cells were spun and suspended at 2 million cells/ml in Hank's balanced salt solution (Life Technologies) supplemented with 2% FCS and 2 μg/ml Propidium Iodide (Sigma). FACS analysis was subsequently carried out on a Becton-Dickinson FACStar-Plus equipped with dual lasers. The SP fraction was visualised as a well-defined, distinct cell population, which stains weakly with Hoechst dye (in far red>670 nm and blue 450 nm) due to the active efflux of dye by multi-drug resistance (mdr)-type proteins on the surface of SP cells. In order to confirm the presence of the SP and establish appropriate sorting gates, verapamil was used to inhibit mdr-protein activity, resulting in loss of SP cells (i.e. cells from the SP fraction shifted into the main population (MP)). $1\times10^4$ purified SP cells were sorted from a starting population of approximately $5\times10^6$ muscle-derived cells. Purified SP cells were spun down at 1000 rpm and resuspended in 50 μl of PBS, divided into 2 tubes (5000 cells/tube) for immediate infection with 2.5×105 viral particles (multiplicity of infection=50) of Ad-Pax7 or Ad-empty (no transgene). SP cells were maintained in suspension at 37° C./5%$CO_2$ during 1 hour infection. After infection, 1 ml of myoblast growth medium consisting of Ham's F-10 Nutrient mixture (Life Technologies) supplemented with 20% FCS and 2.5 ng/ml bFGF (R&D systems) was added to cultures. Infected SP cells were plated in wells of 12 well dishes previously coated with 0.1% rat-tail collagen (Roche) and thereafter maintained in myoblast growth medium for 7 additional days with medium exchanged every two days.

To assess the myogenic conversion of SP cells, immunohistochemistry with antibody reactive to the muscle specific intermediate filament protein, desmin was performed. Importantly the SP fraction of cells from muscle does not contain satellite cells or desmin positive myoblasts (A. Asakura, unpublished data). For staining, infected SP cultures were fixed with 4% paraformaldehyde and permeabilised with 0.3% Triton-X100. Anti-desmin antibody (Clone D33; Dako) was used at a dilution of 1/200 and detected using fluorescein conjugated anti-mouse IgG (Chemicon). Significantly, desmin expression was observed in cell cultures infected with Ad-Pax7 (FIG. 11). By contrast, no desmin reactive cells were observed in cells of cultures infected with Ad-empty. These results indicate that some proportion of muscle-derived SP cells have the capacity to undergo myogenic conversion following exposure to exogenous Pax7.

Example XI

Isolation and Infection of Myf5nlacZ Muscle Cells

Mononuclear cells were obtained from the hind limb skeletal muscle of 2 month old Myf5nlacz mice as described above. The LacZ gene is expressed under the control of the Myf5 locus in these mice. Expression of Myf5nlacZ is observed in cells, which are committed to the muscle lineage thus providing a useful lineage marker for myogenic cells (Tajbakhsh et al., 1996). Myf5nlacZ is not expressed in muscle-derived SP cells (A. Asakura, unpublished data) however satellite cells and myogenic precursor cells in adult muscle express this transgene (Tajbakhsh et al., 1996). Following isolation, Myf5nlacZ muscle derived cells were suspended in muscle stem cell medium composed of Ham's F-10 nutrient mixture (Life Technologies) supplemented with 20% FCS; 5% chicken embryo extract (Life Technologies); antibiotics and fungizone and plated onto plastic tissue culture dishes. The muscle cultures were grown for 5 days under these conditions with the medium exchanged after 1 and 3 days. These culture conditions have been used previously to grow muscle cells with bone-marrow repopulating activity (Jackson et al., 1999). Furthermore, satellite cells and myoblasts do not adhere to plastic and fail to thrive under these conditions (unpublished observations). These muscle-derived cell cultures were subsequently infected with Ad-Pax7 and Ad-empty at a multiplicity of infection of 50. Specifically, $1\times10^5$ cells were infected with $5\times10^6$ viral particles of eitherAd-Pax7 or Ad-empty. Adherent cells on 60 mm tissue culture plates were infected with 1 mL of PBS/virus for 1 hour at 37° C./5% $CO_2$. Following infection, 5 mL of myoblast growth medium was added to cultures. Cultures were maintained in myoblast growth medium for an additional 7 days. To assess expression of MyfnlacZ in Ad-Pax7 and Ad-empty infected cultures, cells were fixed with 4% paraformaldehyde for X-Gal staining as described previously (Asakura et al., 1995). Interestingly, a large number of cells infected with Ad-Pax7 up regulated expression of Myf5nlacZ (FIG. 12). By contrast, MyfnlacZ expressing cells were rarely observed in Ad-empty infected cultures likely a result of contaminating myoblasts. These results suggest that Pax7 expression is sufficient to induce a subset of competent stem cells to enter into the myogenic differentiation program.

Example XII

The Role of PAX7 in the Myogenic Specification of Adult Stem Cells

Mice

Mice carrying a targeted null mutation in Pax7 (hereafter referred to as Pax7−/−) were generously provided by Drs. Ahmed Mansouri and Peter Gruss (Mansouri et al., 1996) and outbred into the SV129 background to increase survival. Myf5nLacZ mice were provided by Dr. S. Tajbakhsh (Tajbakhsh et al., 1996). Mdx mice were obtained from Jackson Labs. Mdx:nu mice were provided by Dr. T. A. Partridge (see Blaveri et al., 1999).

Cell Sorting

Mononuclear cells were recovered from uninjured hindlimb muscles or from cardiotoxin (ctx) damaged TA muscles of Pax7+/+, Pax7± and Pax7−/− mice as described previously (Megeney et al., 1996). Cells were washed twice with ice-cold DMEM supplemented with 5% FBS, passed through 30 μm filters (Miltenyi Biotec) and suspended at a concentration of 2-3×10⁶ cells/ml. Staining was performed for 30 min on ice using the antibodies: CD45-APC (30-F11), CD45.2-FITC (104), Sca1-PE or FITC, (D7) all from BD Pharmingen and CD45-TC (30-F11) from Caltag. Primary antibodies were diluted in cell suspensions at 1:200. After two washes with cold PBS supplemented with 2% FBS, cells were separated on a MoFlo cytometer (DakoCytomation). Sort gates were strictly defined based on isotype control stained cells and single antibody staining. Dead cells and debris were excluded by gating on forward and side scatter profiles. Sorting was performed using single cell mode to achieve the highest possible purity. The purity of sorted populations was routinely >98%.

Retroviral and Adenoviral Gene Expression

Retrovirus was produced according to the 3-plasmid HIT system with plasmids pHIT60, pHIT456, and pHAN-puro as described elsewhere (Soneoka et al., 1995). pHIT60 encodes the MLV retroviral gag-pol, pHIT456 expresses an amphotrophic envelope protein and pHAN-puro is an expression vector with a hybrid CMV-5' LTR promoter driving production of the retroviral transcript. Pax7 or MyoD is translated from this full transcript, whereas the puromycin resistance marker is expressed following retroviral integration from a shorter transcript produced by the SV40 early promoter located 3' to the multiple cloning site. Transient cotransfection of all three plasmids into 293FT cells (Invitrogen) by the calcium phosphate method (Graham and van der Eb, 1973) routinely produced viral titres between 106 and 107 cfu per ml. pHAN-puro was used to produce puromycin-resistant virus for controls.

Purified CD45+:Sca1+ (CDSC) or CD45−:Sca1− cells were spun down, counted, and 20-50, 000 cells were then cultured overnight on collagen coated 4 well chamber slides in HAM's F 10 medium (Invitrogen) supplemented with 20% FBS, antibiotics and 10 ng/ml Stem Cell Factor (R&D systems). The following day, cells were incubated for 6 hr with retrovirus at a 1:1 ratio (complete medium: retrovirus supernatant) with 8 μg/ml polybrene (hexadimethrine bromide; Sigma). After infection, cells were rinsed twice with PBS and all cells were replated in myoblast growth medium. After 48 hours, infected pools were selected in 1 μg/ml puromycin (Sigma) to establish stable CDSCPax7 lines. C3H10T1/2 cells were incubated overnight with MyoD, Pax7 or puro virus and 8 μg/ml polybrene. Adenovirus (type V) was prepared using the Ad-Max adenovirus creation kit (Microbix Biosystems). Adenovirus was purified in CsCl gradients by centrifugation, dialyzed against sterile PBS and frozen down in 15% glycerol at −80° C. Titres of purified adenovirus were determined by plaque assays on 293 cells and were always above 1010 pfu/ml.

Western Blot Analyses

Cell cultures were lysed in RIPA extraction buffer (50mM Tris-HCl pH 7.4, 1% Nonidet P-40, 0.5% NaDeoxycholate, 0.1% Sodium-dodecyl-sulphate, 5 mM EDTA, 150 mM NaCl, 50 mM NaF) supplemented with protease inhibitors (Complete, Roche). The extracts were normalized for protein content using Bio-Rad dye. 40 μg of lysate was separated by sodium dodecyl sulfate-polyacrylamide gel electrophoresis (SDS-PAGE), and transferred to PVDF filters (Immobilonp, Millipore). Filters were probed with antibodies to Pax7 (Developmental Studies Hybridoma Bank [DSHB]); Myf5, 1: 1000 (C-20, Santa-Cruz Biotechnology), MyoD, 1:1000 (C-20, Santa-Cruz Biotechnology), myogenin (F5D, DSHB), and α-tubulin, 1:2000 (T 9026, Sigma). Secondary detection was performed with horseradish peroxidase-conjugated antibodies (BioRad). Protein expression was visualized using the ECL Plus kit (Amersham).

Cardiotoxin-Induced Regeneration and In Vivo Adenovirus Infections

Four to six week old Pax7−/− and wild-type littermates were anesthetized with Halothane gas. 25 μl of 10 μM cardiotoxin (ctx) (Latoxan, France) was injected into the midbelly of the TA muscle, using a 29_G insulin syringe. Mice were sacrificed at 4 days or two weeks after ctx injection. For adenovirus infections, 25 μl of sterile PBS containing 108 particles of purified adenovius-Pax7 or -LacZ was injected 2 days after ctx injection into damaged TA muscles with a 29_G insulin syringe.

Cell Transplantation

Primary CDSC-Pax7 cells cultured in myoblast conditions were trypsinized, washed twice with PBS and suspended at 5×105 cells/25 μl in sterile PBS for cell transplantation. Cells were injected directly into the TA midbelly of 4-6 week old mdx:nude mice. Mice were sacrificed 2 months after cell injections to analyze the myogenic contribution of transplanted cells.

Cell Cultures

Primary satellite cell-derived myoblasts were established from purified CD45-:Sca1− fractions of hindlimb muscle of 4-6 week old Pax7+/+ or Pax7± mice. Myoblasts and CDSC-Pax7 cells were maintained in HAM's F-10 medium (Invitrogen) supplemented with 20% FBS, and 2.5 ng/ml bFGF (Invitrogen) on collagen coated dishes. CDSC-Pax7 cells and primary satellite cell derived myoblasts were differentiated for 1-3 days in DMEM supplemented with 5% Horse-serum. C3H10T1/2 and HEK 293 cells were obtained from the ATCC and maintained in DMEM supplemented with 10% FBS.

Histology and Immunocytochemistry

For analysis of regeneration and enumeration of regenerated myofibers, TA muscles were isolated, embedded in OCT (Tissue-Tek)/20% sucrose and immediately frozen in liquid nitrogen. 10 μm cryosections (cross-sections) from the TA midbelly at the site of ctx injection were stained with Hematoxylin and Eosin (H&E). Central myonuclei in regenerating muscles were counted on at least 2 independent cross-sections of the entire TA muscle per mouse analyzed. Fibers were further identified by immunostaining with antibodies specific to: Desmin, 1:200 (D33, DAKO), dystrophin, 1:500 (Sigma), Pax7 (DSHB) or embryonic fast MyHC (F1.652, Developmental Studies Hybridoma Bank (DSHB), University of Iowa, USA) followed by secondary detection with anti-mouse FITC conjugated antibody, 1:200 (Chemicon). Sections were analyzed on a Zeiss Axioplan 2 microscope.

Cultured cells were fixed with 4% paraformaldehyde, non-specific antigens were blocked in 5% horse serum/PBS and cells were reacted with primary antibodies as follows: Desmin, 1:200 (DAKO); MyoD, 1:200 (5.8A, BD Pharmingen); all MyHC (MF-20, DSHB); Myf5, 1:1000 (C-20, Santa-Cruz Biotechnology); Pax7 (DSHB) and myogenin (F5D, DSHB). Secondary detection was performed using fluorescein- or rhodamine-conjugated antibodies, 1:200 (Chemicon). Myf5nLacZ expression was detected by X-Gal reaction as described previously (Polesskaya et al., 2003).

RT-PCR and Northern analysis

Total RNA was extracted using RNAeasy kits (Qiagen), according to manufacturer's instructions. RT-PCR analysis for endogenous Pax7 mRNA was performed using the GeneAmp PCR Core kit (Perkin-Elmer). RT-PCR using 1 µg of total RNA was conducted as per manufacturer's instructions with the following modifications. cDNA synthesis was extended for 1 hour at 42° C., and 5 µl of the first-strand RT product was used for PCR amplification. PCR conditions for endogenous Pax7 were 94° C.-5 mm; 35 cycles of(94° C.-45 sec; 56° C.-45 sec; 720C-45 sec); 72'C-7min. The PCR primers span intron 8 of the Pax7 gene (Pax7-exon8-fwd 5' gct acc agt aca gcc agt atg 3' (SEQ ID NO: 14) and Pax7-exon9-rev 5' gtc act aag cat ggg tag atg 3') (SEQ ID NO: 15) and amplify sequence in the 3'-UTR of the gene that is not contained in the viral Pax7 expression cassette. RT-PCR products were analyzed by electrophoresis through a TAE-ethidium-agarose gel.

Northern blot studies were performed according to standard techniques using random-primed 32P-dCTP radiolabelled cDNA fragments as probes (Redi-prime, Amersham) (Maniatis et al., 1982). 15 µg of total RNA from various cell cultures was electrophoresed in denaturing-Formaldehyde gels and transferred to Hybond-N filters (Amersham Bioscience).

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Allen, R. E., Sheehan, S. M., Taylor, R. G., Kendall, T. L., and Rice, G. M. (1995). Hepatocyte growth factor activates quiescent skeletal muscle satellite cells in vitro. J Cell Physiol 165, 307-12.

Appell, H. J., Forsberg, S., and Hollmann, W. (1988). Satellite cell activation in human skeletal muscle after training: evidence for muscle fiber neoformation. Int J Sports Med 9, 297-9.

Asakura, A., Lyons, G. E., and Tapscott, S. J. (1995). The regulation of MyoD gene expression: conserved elements mediate expression in embryonic axial muscle. Dev Biol 171, 386-98.

Asakura, A., Seale, P., Girgis-Gabardo, A., Rudnicki, M. A. (2002). Myogenic specification of side population cells in skeletal muscle. J Cell Biol 159, 123-134.

Bancroft, J. D., and Stevens, A. (1990). Theory and practice of histological techniques, 3rd-Edition (Edinburgh; New York: Churchill Livingstone).

Bendall, A. J., Ding, J., Hu, G., Shen, M. M., Abate-Shen, C. (1999). Msx1 antagonizes the myogenic activity of Pax3 in migrating limb muscle precursors. Development 126, 4965-4976.

Bennicelli, J. L., Advani, S., Schafer, B. W., and Barr, F. G. (1999). PAX3 and PAX7 exhibit conserved cis-acting transcription repression domains and utilize a common gain of function mechanism in alveolar rhabdomyosarcoma. Oncogene 18, 4348-56.

Bischoff, R. (1994). The satellite cell and muscle regeneration. In Myogenesis, A. G. Engel and C. Franszini-Armstrong, eds. (New York: McGraw-Hill), pp. 97-118.

Blaveri, K., Heslop, L., Yu, D. S., Rosenblatt, J. D., Gross, J. G., et al. (1999). Patterns of repair of dystrophic mouse muscle: studies on isolated fibers. Dev Dyn 216, 244-256.

Borycki, A. G., and Emerson, C. P. (1997). Muscle determination: another key player in myogenesis? Curr Biol 7, R620-3.

Borycki, A. G., Li, J., Jin, F., Emerson, C. P., Epstein, J. A. (1999). Pax3 functions in cell survival and in pax7 regulation. Development 126, 1665-1674.

Braissant, O., and Wahli, W. (1998). Differential expression of peroxisome proliferator-activated receptor- alpha, -beta, and -gamma during rat embryonic development. Endocrinology 139, 2748-54.

Burt et al., 2004 J. Exper.Med., 199, 895-904.

Bulfield, G., Siller, W. G., Wight, P. A., Moore, K. J. (1984). X chromosome-linked muscular dystrophy (mdx) in the mouse. Proc Natl Acad Sci USA 81, 1189-1192.

Cao, B., Zheng, B., Jankowski, R. J., Kimura, S., Ikezawa, M., et al. (2003). Muscle stem cells differentiate into haematopoietic lineages but retain myogenic potential. Nat Cell Biol.

Charge, S. B. P., Rudnicki, M. A. (2004). Cellular and molecular regulation of muscle regeneration. Physiol Rev 84, 209-238.

Chomczynski, P., and Sacchi, N. (1987). Single-step method of RNA isolation by acid guanidinium thiocyanate-phenol-chloroform extraction. Anal Biochem 162, 156-9.

Conway, S. J., Henderson, D. J., Kirby, M. L., Anderson, R. H., and Copp, A. J. (1997). Development of a lethal congenital heart defect in the splotch (Pax3) mutant mouse. Cardiovasc Res 36, 163-73.

Cornelison, D. D., and Wold, B. J. (1997). Single-cell analysis of regulatory gene expression in quiescent and activated mouse skeletal muscle satellite cells. Dev Biol 191, 270-83.

Cossu, G., Kelly, R., Tajbakhsh, S., Di Donna, S., Vivarelli, E., et al. (1996). Activation of different myogenic pathways: myf-5 is induced by the neural tube and MyoD by the dorsal ectoderm in mouse paraxial mesoderm. Development 122, 429-437.

Cunningham, B. A., Hemperly, J. J., Murray, B. A., Prediger, E. A., Brackenbury, R., and Edelman, G. M. (1987). Neural cell adhesion molecule: structure, immunoglobulin-like domains, cell surface modulation, and alternative RNA splicing. Science 236, 799-806.

Dahl, E., Koseki, H., and Balling, R. (1997). Pax genes and organogenesis. Bioessays 19, 755-65.

Daston, G., Lamar, E., Olivier, M., and Goulding, M. (1996). Pax-3 is necessary for migration but not differentiation of limb muscle precursors in the mouse. Development 122, 1017-27.

De Angelis, L., Berghella, L., Coletta, M., Lattanzi, L., Zanchi, M., Cusella-De Angelis, M. G., Ponzetto, C., and Cossu, G. (1999). Skeletal myogenic progenitors originating from embryonic dorsal aorta coexpress endothelial and myogenic markers and contribute to postnatal muscle growth and regeneration [see comments]. J Cell Biol 147, 869-78.

Delfini, M., Hirsinger, E., Pourquie, O., Duprez, D. (2000). Delta 1-activated notch inhibits muscle differentiation without affecting Myf5 and Pax3 expression in chick limb myogenesis. Development 127, 5213-5224.

Epstein, J. A., Lam, P., Jepeal, L., Maas, R. L., and Shapiro, D. N. (1995). Pax3 inhibits myogenic differentiation of cultured myoblast cells. J Biol Chem 270, 11719-22.

Epstein, J. A., Shapiro, D. N., Cheng, J., Lam, P. Y., and Maas, R. L. (1996). Pax3 modulates expression of the c-Met receptor during limb muscle development. Proc Natl Acad Sci USA 93, 4213-8.

Fleming, T. J., Fleming, M. L., and Malek, T. R. (1993). Selective expression of Ly-6G on myeloid lineage cells in mouse bone marrow. RB6-8C5 mAb to granulocyte-differentiation antigen (Gr-1) detects members of the Ly-6 family. J Immunol 151,2399-408.

George-Weinstein, M., Foster, R. F., Gerhart, J. V., and Kaufman, S. J. (1993). In vitro and in vivo expression of alpha 7 integrin and desmin define the primary and secondary myogenic lineages. Dev Biol 156, 209-29.

Gibson, M. C., and Schultz, E. (1983). Age-related differences in absolute numbers of skeletal muscle satellite cells. Muscle Nerve 6, 574-80.

Goodell, M. A., Brose, K., Paradis, G., Conner, A. S., and Mulligan, R. C. (1996). Isolation and functional properties of murine hematopoietic stem cells that are replicating in vivo. J Exp Med 183, 1797-806.

Goodell, M. A., Rosenzweig, M., Kim, H., Marks, D. F., DeMaria, M., Paradis, G., Grupp, S. A., Sieff, C. A., Mulligan, R. C., and Johnson, R. P. (1997). Dye efflux studies suggest that hematopoietic stem cells expressing low or undetectable levels of CD34 antigen exist in multiple species. Nat Med 3, 1337-45.

Goulding, M. D., Chalepakis, G., Deutsch, U., Erselius, J. R., and Gruss, P. (1991). Pax-3, a novel murine DNA binding protein expressed during early neurogenesis. Embo J 10, 1135-47.

Goulding, M., Lumsden, A., Paquette, A. J. (1994). Regulation of Pax-3 expression in the dermomyotome and its role in muscle development. Development 120, 957-971.

Graham, F. L., van der Eb, A. J. (1973). Transformation of rat cells by DNA of human adenovirus 5. Virology 54, 536-539.

Graw, J. (1999). Cataract mutations and lens development. Prog Retin Eye Res 18, 235-67.

Grounds, M. D., and Yablonka-Reuveni, Z. (1993). Molecular and cell biology of skeletal muscle regeneration. Mol Cell Biol Hum Dis Ser 3, 210-56.

Gussoni, E., Soneoka, Y., Strickland, C. D., Buzney, E. A., Khan, M. K., Flint, A. F., Kunkel, L. M., and Mulligan, R. C. (1999). Dystrophin expression in the mdx mouse restored by stem cell transplantation. Nature 401, 390-4.

Heanue, T. A., Reshef, R., Davis, R. J., Mardon, G., Oliver, G., Tomarev, S., Lassar, A. B., and Tabin, C. J. (1999). Synergistic regulation of vertebrate muscle development by Dach2, Eya2, and Six 1, homologs of genes required for Drosophila eye formation. Genes Dev 13, 3231-43.

Heslop, L., Morgan, J. E., Partridge, T. A. (2000). Evidence for a myogenic stem cell that is exhausted in dystrophic muscle. J Cell Sci 113, 2299-2308.

Holst, B. D., Wang, Y., Jones, F. S., and Edelman, G. M. (1997). A binding site for Pax proteins regulates expression of the gene for the neural cell adhesion molecule in the embryonic spinal cord. Proc Natl Acad Sci USA 94, 1465-70.

Hubank, M., and Schatz, D. G. (1994). Identifying differences in mRNA expression by representational difference analysis of cDNA. Nucleic Acids Res 22, 5640-8.

Hurko, O., and Walsh, F. S. (1983). Human fetal muscle-specific antigen is restricted to regenerating myofibers in diseased adult muscle. Neurology 33, 737-43.

Irintchev, A., Zeschnigk, M., Starzinski-Powitz, A., and Wernig, A. (1994). Expression pattern of M-cadherin in normal, denervated, and regenerating mouse muscles. Dev Dyn 199, 326-37.

Jackson, K. A., Mi, T., and Goodell, M. A. (1999). Hematopoietic potential of stem cells isolated from murine skeletal muscle [see comments]. Proc Natl Acad Sci USA 96, 14482-6.

Jostes, B., Walther, C., and Gruss, P. (1990). The murine paired box gene, Pax7, is expressed specifically during the development of the nervous and muscular system. Mech Dev 33, 27-37.

Kablar, B. (1995). Structural study on the appearance of innervation in the stomach of mouse and rat embryos. Tissue Cell 27, 309-15.

Kay, P. H., Harmon, D., Fletcher, S., Robertson, T., Ziman, M., and Papadimitriou, J. M. (1998). Pax7 includes two polymorphic homeoboxes which contain rearrangements associated with differences in the ability to regenerate damaged skeletal muscle in adult mice. Int J Biochem Cell Biol 30, 261-9.

Kay, P. H., Harmon, D., Fletcher, S., Ziman, M., Jacobsen, P. F., and Papadimitriou, J. M. (1997). Variation in the methylation profile and structure of Pax3 and Pax7 among different mouse strains and during expression. Gene 184, 45-53.

Kay, P. H., Mitchell, C. A., Akkari, A., and Papadimitriou, J. M. (1995). Association of an unusual form of a Pax7-like gene with increased efficiency of skeletal muscle regeneration. Gene 163, 171-7.

Kay, P. H., and Ziman, M. R. (1999). Alternate Pax7 paired box transcripts which include a trinucleotide or a hexanucleotide are generated by use of alternate 3' intronic splice sites which are not utilized in the ancestral homologue. Gene 230, 55-60.

Khan, J., Bittner, M. L., Saal, L. H., Teichmann, U., Azorsa, D. O., Gooden, G. C., Pavan, W. J., Trent, J. M., and Meltzer, P. S. (1999). cDNA microarrays detect activation of a myogenic transcription program by the PAX3-FKHR fusion oncogene. Proc Natl Acad Sci USA 96, 13264-9.

Leenen, P. J., de Bruijn, M. F., Voerman, J. S., Campbell, P. A., and van Ewijk, W. (1994). Markers of mouse macrophage development detected by monoclonal antibodies. J Immunol Methods 174, 5-19.

Maniatis, T., Fritsch, E. F., and Sambrook, J. (1982). Molecular cloning : a laboratory manual (Cold Spring Harbor, N.Y.: Cold Spring Harbor Laboratory).

Mansouri, A., Chowdhury, K., and Gruss, P. (1998). Follicular cells of the thyroid gland require Pax8 gene function. Nat Genet 19, 87-90.

Mansouri, A., Goudreau, G., and Gruss, P. (1999). Pax genes and their role in organogenesis. Cancer Res 59, 1707s-1709s; discussion 1709s-1710s.

Mansouri, A., Hallonet, M., and Gruss, P. (1996). Pax genes and their roles in cell differentiation and development. Curr Opin Cell Biol 8, 851-7.

Mansouri, A., Stoykova, A., and Gruss, P. (1994). Pax genes in development. J Cell Sci Suppl 18, 35-42.

Mansouri, A., Stoykova, A., Torres, M., and Gruss, P. (1996). Dysgenesis of cephalic neural crest derivatives in Pax7-/- mutant mice. Development 122, 831-8.

Maroto, M., Reshef, R., Munsterberg, A. E., Koester, S., Goulding, M., and Lassar, A. B. (1997). Ectopic Pax-3 activates MyoD and Myf-5 expression in embryonic mesoderm and neural tissue. Cell 89, 139-48.

McKinney-Freeman, S. L., Jackson, K. A., Camargo, F. D., Ferrari, G., Mavilio, F., et al. (2002). Muscle-derived hematopoietic stem cells are hematopoietic in origin. Proc Natl Acad Sci USA 99, 1341-1346.

Megeney, L. A., Kablar, B., Garrett, K., Anderson, J. E., and Rudnicki, M. A. (1996). MyoD is required for myogenic stem cell function in adult skeletal muscle. Genes Dev 10, 1173-83.

Montarras, D., Lindon, C., Pinset, C., Domeyne, P. (2000). Cultured myf5 null and myoD null muscle precursor cells display distinct growth defects. Biol Cell 92, 565-572.

Morlet, K., Grounds, M. D., and McGeachie, J. K. (1989). Muscle precursor replication after repeated regeneration of skeletal muscle in mice. Anat Embryol 180, 471-8.

Munsterberg, A. E., Lassar, A. B. (1995). Combinatorial signals from the neural tube, floor plate and notochord induce myogenic bHLH gene expression in the somite. Development 121, 651-660.

Naldini, L., Blomer, U., Gallay, P., Ory, D., Mulligan, R., Gage, F. H., Verma, I. M., and Trono, D. (1996). In vivo gene delivery and stable transducti6n of nondividing cells by a lentiviral vector. Science 272, 263-7.

Ng, P., Parks, R. J., Cummings, D. T., Evelegh, C. M., Sankar, U., and Graham, F. L. (1999). A high-efficiency Cre/loxP-based system for construction of adenoviral vectors. Hum Gene Ther 10, 2667-72.

Noll, M. (1993). Evolution and role of Pax genes. Curr Opin Genet Dev 3, 595-605.

Nutt, S. L., Heavey, B., Rolink, A. G., and Busslinger, M. (1999). Commitment to the B-lymphoid lineage depends on the transcription factor Pax5 [see comments]. Nature 401, 556-62.

Nutt, S. L., Thevenin, C., and Busslinger, M. (1997). Essential functions of Pax-5 (BSAP) in pro-B cell development. Immunobiology 198, 227-35.

Pagel, C. N., Partridge, T. A. (1999). Covert persistence of mdx mouse myopathy is revealed by acute and chronic effects of irradiation. J Neurol Sci 164, 103-116.

Parker, M. H., Seale, P., Rudnicki, M. A. (2003). Looking back to the embryo: defining transcriptional networks in adult myogenesis. Nat Rev Genet 4, 497-507.

Peters, H., Wilm, B., Sakai, N., Imai, K., Maas, R., and Balling, R. (1999). Pax1 and Pax9 synergistically regulate vertebral column development. Development 126, 5399-408.

Petropoulos, H., Skerane, I. S. (2002). Beta -catenin is essential and sufficient for skeletal myogenesis in pl9 cells. J Biol Chem 277, 15393-15399.

Polesskaya, A., Seale, P., Rudnicki, M. A. (2003). Wnt Signaling Induces the Myogenic Specification of Resident CD45+ Adult Stem Cells during Muscle Regeneration. Cell 113, 841-852.

Pourquie, O., Coltey, M., Breant, C., Le Douarin, N. M. (1995). Control of somite patterning by signals from the lateral plate. Proc Natl Acad Sci USA 92, 3219-3223.

Pourquie, O., Fan, C. M., Coltey, M., Hirsinger, E., Watanabe, Y., et al. (1996). Lateral and axial signals involved in avian somite patterning: a role for BMP4. Cell 84, 461-471.

Qu-Petersen, Z., Deasy, B., Jankowski, R., Ikezawa, M., Cummins, J., et al. (2002). Identification of a novel population of muscle stem cells in mice: potential for muscle regeneration. J Cell Biol 157, 851-864.

Relaix, F., and Buckingham, M. (1999). From insect eye to vertebrate muscle: redeployment of a regulatory network. Genes Dev 13, 3171-8.

Represa, J., Frenz, D. A., and Van De Water, T. R. (2000). Genetic patterning of embryonic inner ear development. Acta Otolaryngol 120, 5-10.

Robertson, E., J. (1987). Embryo-Derived Stem Cell Lines. In Teratocarcinomas and embryonic stem cells: a practical approach, E. J. Robertson, ed. (Oxford: IRL Press Ltd.), pp. 71-112.

Rolink, A. G., Nutt, S. L., Melchers, F., and Busslinger, M. (1999). Long-term in vivo reconstitution of T-cell development by Pax5-deficient B-cell progenitors [see comments]. Nature 401, 603-6.

Rosenblatt, J. D., Yong, D., and Parry, D. J. (1994). Satellite cell activity is required for hypertrophy of overloaded adult rat muscle. Muscle Nerve 17, 608-13.

Sabourin, L. A., Girgis-Gabardo, A., Seale, P., Asakura, A., and Rudnicki, M. A. (1999). Reduced differentiation potential of primary MyoD-/- myogenic cells derived from adult skeletal muscle. J Cell Biol 144, 631-43.

Schafer, B. W., Czemy, T., Bemasconi, M., Genini, M., and Busslinger, M. (1994). Molecular cloning and characterization of a human PAX-7 cDNA expressed in normal and neoplastic myocytes. Nucleic Acids Res 22, 4574-82.

Schultz, E., and Jaryszak, D. L. (1985). Effects of skeletal muscle regeneration on the proliferation potential of satellite cells. Mech Ageing Dev 30, 63-72.

Schultz, E., Jaryszak, D. L., and Valliere, C. R. (1985). Response of satellite cells to focal skeletal muscle injury. Muscle Nerve 8, 217-22.

Schultz, E., Jaryszak, D. L., Gibson, M. C., Albright, D. J. (1986). Absence of exogenous satellite cell contribution to regeneration of frozen skeletal muscle. J Muscle Res Cell Motil 7, 361-367.

Schwarz, M., Alvarez-Bolado, G., Urbanek, P., Busslinger, M., and Gruss, P. (1997). Conserved biological function between Pax-2 and Pax-5 in midbrain and cerebellum development: evidence from targeted mutations. Proc Natl Acad Sci USA 94, 14518-23.

Seale, P., and Rudnicki, M. A. (2000). A new look at the origin, function, and "stem-cell" status of muscle satellite cells. Dev Biol 218, 115-24.

Seale, P., Sabourin, L. A., Girgis-Gabardo, A., Mansouri, A., Gruss, P., and Rudnicki, M. A. (2000). Pax7 is required for the specification of myogenic satellite cells [In Process Citation]. Cell 102, 777-86.

Sicinski, P., Geng, Y., Ryder-Cook, A. S., Bamard, E. A., Darlison, M. G., and Bamard, P. J. (1989). The molecular basis of muscular dystrophy in the mdx mouse: a point mutation. Science 244, 1578-80.

Soneoka, Y., Cannon, P. M., Ramsdale, E. E., Griffiths, J. C., Romano, G., Kingsman, S. M., and Kingsman, A. J. (1995). A transient three-plasmid expression system for the production of high titer retroviral vectors. Nucleic Acids Res 23, 628-33.

Sosa-Pineda, B., Chowdhury, K., Torres, M., Oliver, G., and Gruss, P. (1997). The Pax4 gene is essential for differentiation of insulin-producing beta cells in the mammalian pancreas. Nature 386, 399-402.

St-Onge, L., Sosa-Pineda, B., Chowdhury, K., Mansouri, A., and Gruss, P. (1997). Pax6 is required for differentiation of glucagon-producing alpha-cells in mouse pancreas. Nature 387, 406-9.Strachan, T., and Read, A. P. (1994). PAX genes. Curr Opin Genet Dev 4, 427-38.

Strachan, T., and Read, A. P. (1994). PAX genes. Curr Opin Genet Dev 4, 427-38.

Tajbakhsh, S., Bober, E., Babinet, C., Pournin, S., Arnold, H., and Buckingham, M. (1996). Gene targeting the myf-5 locus with nlacZ reveals expression of this myogenic factor in mature skeletal muscle fibres as well as early embryonic muscle. Dev Dyn 206, 291-300.

Tajbakhsh, S., Borello, U., Vivarelli, E., Kelly, R., Papkoff, J., et al. (1998). Differential activation of Myf5 and MyoD by different Wnts in explants of mouse paraxial mesoderm and the later activation of myogenesis in the absence of Myf5. Development 125, 4155-4162.

Tajbakhsh, S., Rocancourt, D., Cossu, G., and Buckingham, M. (1997). Redefining the genetic hierarchies controlling skeletal myogenesis: Pax-3 and Myf-5 act upstream of MyoD. Cell 89, 127-38.

Torban, E., Eccles, M. R., Favor, J., and Goodyer, P. R. (2000). PAX2 suppresses apoptosis in renal collecting duct cells. Am J Pathol 157, 833-42.

Torrente, Y., Tremblay, J. P., Pisati, F., Belicchi, M., Rossi, B., et al. (2001). Intraarterial injection of muscle-derived CD34(+)Sca-1 (+) stem cells restores dystrophin in mdx mice. J Cell Biol 152, 335-348.

Tremblay, P., Dietrich, S., Mericskay, M., Schubert, F. R., Li, Z., and Paulin, D. (1998). A crucial role for Pax3 in the development of the hypaxial musculature and the long-range migration of muscle precursors. Dev Biol 203, 49-61.

Wakeford, S., Watt, D. J., Partridge, T. A. (1991). X-irradiation improves mdx mouse muscle as a model of myofiber loss in DMD. Muscle Nerve 14, 42-50.

Williams, B. A., and Ordahl, C. P. (1994). Pax-3 expression in segmental mesoderm marks early stages in myogenic cell specification. Development 120, 785-96.

Wilm, B., Dahl, E., Peters, H., Balling, R., and Imai, K. (1998). Targeted disruption of PaxI defines its null phenotype and proves haploinsufficiency. Proc Natl Acad Sci USA 95, 8692-7.

Ziman, M. R., Fletcher, S., Kay, P. H. (1997). Alternate Pax7 transcripts are expressed specifically in skeletal muscle, brain and other organs of adult mice. Int J Biochem Cell Biol 29, 1029-1036.

What is claimed is:

1. An isolated CD45⁺:Sca1⁺ skeletal muscle stem cell transformed with a nucleotide sequence encoding Pax7.

2. The isolated cell of claim 1, wherein said cell is derived from a subject after birth.

3. The isolated cell of claim 1, said cell being an adult stem cell.

4. The isolated cell of claim 1, wherein said cell is a mammalian cell.

5. The isolated cell of claim 4, wherein said mammalian cell is selected from the group consisting of mice, cattle, sheep, goat, pig, dog, cat, rat, rabbit, primate, and human.

6. The isolated cell of claim 1, wherein said nucleotide sequence additionally encodes one or more wild-type muscle proteins, one or more wild-type muscle variant proteins, or a combination thereof.

7. The isolated cell of claim 1, further transformed with a second nucleotide sequence encoding one or more wild-type muscle proteins, one or more wild-type muscle variant proteins, or a combination thereof.

8. The isolated cell of claim 7, wherein said one or more wild-type muscle proteins or said one or more wild-type variant muscle proteins comprise dystrophin, calpain-3, one or more sarcoglycan complex members, α-sarcoglycan, β-sarcoglycan, γ-sarcoglycan and δ-sarcoglycan, laminin, actin, myosin, calcineurin, NFATc1, NFATc2, NFATc3, utrophin or a combination thereof.

9. A composition consisting of one or more cells as defined in claim 1 and an acceptable carrier.

10. The composition of claim 9, wherein said acceptable carrier is a cell culture medium, a cell growth medium, a cell cryopreservation medium, an assay medium, an isolation medium, or a delivery or administration medium.

* * * * *

UNITED STATES PATENT AND TRADEMARK OFFICE
CERTIFICATE OF CORRECTION

PATENT NO. : 7,384,784 B2
APPLICATION NO. : 10/835898
DATED : June 10, 2008
INVENTOR(S) : Rudnicki et al.

It is certified that error appears in the above-identified patent and that said Letters Patent is hereby corrected as shown below:

On Page 2, Under References Cited, Under OTHER PUBLICATIONS, in
    Grounds, replace "trerapy" with --therapy--.

On Page 2, Under References Cited, Under OTHER PUBLICATIONS, in
    Heanue et al., replace "requied" with --required--.

On Page 2, Under References Cited, Under OTHER PUBLICATIONS, in
    Torrente et al., replace "Injectin" with --Injection--.

Column 1,
    Line 28, replace "synthesises" with --synthesizes--.
    Line 56, replace "dystropy" with --dystrophy--.

Column 5,
    Line 50, replace "hybridisation" with --hybridization--.

Column 7,
    Line 18, replace "NP13002575" with --NP_002575--.
    Line 58, replace "regeneratingPax7" with --regenerating Pax7--.

Column 9,
    Line 63, replace "other" with --of the--.

Column 10,
    Line 61, replace "hetorologous" with --heterologous--.

Column 13,
    Line 54, replace "phenomenom" with --phenomenon--.
    Line 64, replace "phrmaceutically" with --pharmaceutically--.

Column 18,
    Line 41, replace "$CD45^{+:Sca}1^{+}$" with --$CD45^{+}:Sca1^{+}$--.
    Line 52, replace "composnets" with --components--.

Column 20,
    Line 51, replace "intraperitonally." with --intraperitoneally.--.

Column 21,
    Line 3, replace "protein (s)" with --protein(s)--.

CERTIFICATE OF CORRECTION (continued)
U.S. Pat. No. 7,384,784 B2

Column 23,
    Line 23, replace "(FIG. 28A-day" with --(FIG. 28A-day 0)--.
    Line 24, replace "0). Moreover," with --Moreover--.

Column 24,
    Line 1, replace "dystophin" with --dystrophin--.
    Line 64, replace "Immunohistochemisty" with --Immunohistochemistry--.

Column 25,
    Line 32, replace "nay" with --any--.

Column 29,
    Line 6, replace "Propidium-Iodide" with --Propidium-Iodide--.

Column 32,
    Line 56, replace "C2C 12" with --C2C12--.

Column 34,
    Line 34, replace "eitherAd-Pax7" with --either Ad-Pax7--.

Column 37,
    Line 11, replace "720C-45 sec);" with --72°C-45 Sec);--.

Signed and Sealed this

Twenty-sixth Day of January, 2010

David J. Kappos
*Director of the United States Patent and Trademark Office*

SEQUENCE LISTING

```
<160> NUMBER OF SEQ ID NOS: 13

<210> SEQ ID NO 1
<211> LENGTH: 520
<212> TYPE: PRT
<213> ORGANISM: Homo sapiens

<400> SEQUENCE: 1

Met Ala Ala Leu Pro Gly Thr Val Pro Arg Met Met Arg Pro Ala Pro
 1               5                  10                  15

Gly Gln Asn Tyr Pro Arg Thr Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
    50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
                85                  90                  95

Arg Pro Gly Ala Ile Gly Gly Ser Lys Pro Arg Gln Val Ala Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Arg Leu Leu Lys Asp Gly His Cys Asp
    130                 135                 140

Arg Ser Thr Val Pro Ser Gly Leu Val Ser Ser Ile Ser Arg Val Leu
145                 150                 155                 160

Arg Ile Lys Phe Gly Lys Glu Glu Glu Asp Glu Ala Asp Lys Lys
                165                 170                 175

Glu Asp Asp Gly Glu Lys Lys Ala Lys His Ser Ile Asp Gly Ile Leu
            180                 185                 190

Gly Asp Lys Gly Asn Arg Leu Asp Glu Gly Ser Asp Val Glu Ser Glu
        195                 200                 205

Pro Asp Leu Pro Leu Lys Arg Lys Gln Arg Arg Ser Arg Thr Thr Phe
    210                 215                 220

Thr Ala Glu Gln Leu Glu Glu Leu Glu Lys Ala Phe Glu Arg Thr His
```

```
                225                 230                 235                 240

Tyr Pro Asp Ile Tyr Thr Arg Glu Glu Leu Ala Gln Arg Thr Lys Leu
                245                 250                 255

Thr Glu Ala Arg Val Gln Val Trp Phe Ser Asn Arg Arg Ala Arg Trp
            260                 265                 270

Arg Lys Gln Ala Gly Ala Asn Gln Leu Ala Ala Phe Asn His Leu Leu
        275                 280                 285

Pro Gly Gly Phe Pro Pro Thr Gly Met Pro Thr Leu Pro Pro Tyr Gln
    290                 295                 300

Leu Pro Asp Ser Thr Tyr Pro Thr Thr Ile Ser Gln Asp Gly Gly
305                 310                 315                 320

Ser Thr Val His Arg Pro Gln Pro Leu Pro Pro Ser Thr Met His Gln
                325                 330                 335

Gly Gly Leu Ala Ala Ala Ala Ala Ala Ala Asp Thr Ser Ser Ala Tyr
            340                 345                 350

Gly Ala Arg His Ser Phe Ser Ser Tyr Ser Asp Ser Phe Met Asn Pro
        355                 360                 365

Ala Ala Pro Ser Asn His Met Asn Pro Val Ser Asn Gly Leu Ser Pro
    370                 375                 380

Gln Val Met Ser Ile Leu Gly Asn Pro Ser Ala Val Pro Pro Gln Pro
385                 390                 395                 400

Gln Ala Asp Phe Ser Ile Ser Pro Leu His Gly Gly Leu Asp Ser Ala
                405                 410                 415

Thr Ser Ile Ser Ala Ser Cys Ser Gln Arg Ala Asp Ser Ile Lys Pro
            420                 425                 430

Gly Asp Ser Leu Pro Thr Ser Gln Ala Tyr Cys Pro Pro Thr Tyr Ser
        435                 440                 445

Thr Thr Gly Tyr Ser Val Asp Pro Val Ala Gly Tyr Gln Tyr Gly Gln
    450                 455                 460

Tyr Gly Gln Ser Glu Cys Leu Val Pro Trp Ala Ser Pro Val Pro Ile
465                 470                 475                 480

Pro Ser Pro Thr Pro Arg Ala Ser Cys Leu Phe Met Glu Ser Tyr Lys
                485                 490                 495

Val Val Ser Gly Trp Gly Met Ser Ile Ser Gln Met Glu Lys Leu Lys
            500                 505                 510

Ser Ser Gln Met Glu Gln Phe Thr
        515                 520

<210> SEQ ID NO 2
<211> LENGTH: 518
<212> TYPE: PRT
<213> ORGANISM: Homo sapiens

<400> SEQUENCE: 2

Met Ala Ala Leu Pro Gly Thr Val Pro Arg Met Met Arg Pro Ala Pro
 1               5                  10                  15

Gly Gln Asn Tyr Pro Arg Thr Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
    50                  55                  60

His Gly Ile Arg Pro Cys Val Ile Ser Arg Gln Leu Arg Val Ser His
65                  70                  75                  80
```

-continued

Gly Cys Val Ser Lys Ile Leu Cys Arg Tyr Gln Glu Thr Gly Ser Ile
            85                  90                  95

Arg Pro Gly Ala Ile Gly Gly Ser Lys Pro Arg Gln Val Ala Thr Pro
            100                 105                 110

Asp Val Glu Lys Lys Ile Glu Glu Tyr Lys Arg Glu Asn Pro Gly Met
            115                 120                 125

Phe Ser Trp Glu Ile Arg Asp Arg Leu Leu Lys Asp Gly His Cys Asp
            130                 135                 140

Arg Ser Thr Val Pro Ser Val Ser Ser Ile Ser Arg Val Leu Arg Ile
145                 150                 155                 160

Lys Phe Gly Lys Lys Glu Glu Asp Glu Ala Asp Lys Lys Glu Asp
                165                 170                 175

Asp Gly Glu Lys Lys Ala Lys His Ser Ile Asp Gly Ile Leu Gly Asp
            180                 185                 190

Lys Gly Asn Arg Leu Asp Glu Gly Ser Asp Val Glu Ser Glu Pro Asp
            195                 200                 205

Leu Pro Leu Lys Arg Lys Gln Arg Arg Ser Arg Thr Thr Phe Thr Ala
210                 215                 220

Glu Gln Leu Glu Glu Leu Glu Lys Ala Phe Glu Arg Thr His Tyr Pro
225                 230                 235                 240

Asp Ile Tyr Thr Arg Glu Glu Leu Ala Gln Arg Thr Lys Leu Thr Glu
            245                 250                 255

Ala Arg Val Gln Val Trp Phe Ser Asn Arg Arg Ala Arg Trp Arg Lys
            260                 265                 270

Gln Ala Gly Ala Asn Gln Leu Ala Ala Phe Asn His Leu Leu Pro Gly
            275                 280                 285

Gly Phe Pro Pro Thr Gly Met Pro Thr Leu Pro Pro Tyr Gln Leu Pro
            290                 295                 300

Asp Ser Thr Tyr Pro Thr Thr Thr Ile Ser Gln Asp Gly Gly Ser Thr
305                 310                 315                 320

Val His Arg Pro Gln Pro Leu Pro Pro Ser Thr Met His Gln Gly Gly
            325                 330                 335

Leu Ala Ala Ala Ala Ala Ala Asp Thr Ser Ser Ala Tyr Gly Ala
            340                 345                 350

Arg His Ser Phe Ser Ser Tyr Ser Asp Ser Phe Met Asn Pro Ala Ala
            355                 360                 365

Pro Ser Asn His Met Asn Pro Val Ser Asn Gly Leu Ser Pro Gln Val
            370                 375                 380

Met Ser Ile Leu Gly Asn Pro Ser Ala Val Pro Pro Gln Pro Gln Ala
385                 390                 395                 400

Asp Phe Ser Ile Ser Pro Leu His Gly Gly Leu Asp Ser Ala Thr Ser
            405                 410                 415

Ile Ser Ala Ser Cys Ser Gln Arg Ala Asp Ser Ile Lys Pro Gly Asp
            420                 425                 430

Ser Leu Pro Thr Ser Gln Ala Tyr Cys Pro Pro Thr Tyr Ser Thr Thr
            435                 440                 445

Gly Tyr Ser Val Asp Pro Val Ala Gly Tyr Gln Tyr Gly Gln Tyr Gly
            450                 455                 460

Gln Ser Glu Cys Leu Val Pro Trp Ala Ser Pro Val Pro Ile Pro Ser
465                 470                 475                 480

Pro Thr Pro Arg Ala Ser Cys Leu Phe Met Glu Ser Tyr Lys Val Val
            485                 490                 495

Ser Gly Trp Gly Met Ser Ile Ser Gln Met Glu Lys Leu Lys Ser Ser

```
                     500                 505                 510
Gln Met Glu Gln Phe Thr
            515

<210> SEQ ID NO 3
<211> LENGTH: 520
<212> TYPE: PRT
<213> ORGANISM: Homo sapiens

<400> SEQUENCE: 3

Met Ala Ala Leu Pro Gly Thr Val Pro Arg Met Met Arg Pro Ala Pro
  1               5                  10                  15

Gly Gln Asn Tyr Pro Arg Thr Gly Phe Pro Leu Glu Val Ser Thr Pro
             20                  25                  30

Leu Gly Gln Gly Arg Val Asn Gln Leu Gly Gly Val Phe Ile Asn Gly
         35                  40                  45

Arg Pro Leu Pro Asn His Ile Arg His Lys Ile Val Glu Met Ala His
     50                  55                  60

His Gly Ile Arg Pro Cys Val Ile Ser Arg Gln Leu Arg Val Ser His
 65                  70                  75                  80

Gly Cys Val Ser Lys Ile Leu Cys Arg Tyr Gln Glu Thr Gly Ser Ile
                 85                  90                  95

Arg Pro Gly Ala Ile Gly Gly Ser Lys Pro Arg Gln Val Ala Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Arg Leu Leu Lys Asp Gly His Cys Asp
    130                 135                 140

Arg Ser Thr Val Pro Ser Gly Leu Val Ser Ser Ile Ser Arg Val Leu
145                 150                 155                 160

Arg Ile Lys Phe Gly Lys Lys Glu Glu Glu Asp Glu Ala Asp Lys Lys
                165                 170                 175

Glu Asp Asp Gly Glu Lys Lys Ala Lys His Ser Ile Asp Gly Ile Leu
            180                 185                 190

Gly Asp Lys Gly Asn Arg Leu Asp Glu Gly Ser Asp Val Glu Ser Glu
        195                 200                 205

Pro Asp Leu Pro Leu Lys Arg Lys Gln Arg Arg Ser Arg Thr Thr Phe
    210                 215                 220

Thr Ala Glu Gln Leu Glu Glu Leu Glu Lys Ala Phe Glu Arg Thr His
225                 230                 235                 240

Tyr Pro Asp Ile Tyr Thr Arg Glu Glu Leu Ala Gln Arg Thr Lys Leu
                245                 250                 255

Thr Glu Ala Arg Val Gln Val Trp Phe Ser Asn Arg Arg Ala Arg Trp
            260                 265                 270

Arg Lys Gln Ala Gly Ala Asn Gln Leu Ala Ala Phe Asn His Leu Leu
        275                 280                 285

Pro Gly Gly Phe Pro Pro Thr Gly Met Pro Thr Leu Pro Pro Tyr Gln
    290                 295                 300

Leu Pro Asp Ser Thr Tyr Pro Thr Thr Thr Ile Ser Gln Asp Gly Gly
305                 310                 315                 320

Ser Thr Val His Arg Pro Gln Pro Leu Pro Pro Ser Thr Met His Gln
                325                 330                 335

Gly Gly Leu Ala Ala Ala Ala Ala Ala Asp Thr Ser Ser Ala Tyr
            340                 345                 350
```

-continued

```
Gly Ala Arg His Ser Phe Ser Ser Tyr Ser Asp Ser Phe Met Asn Pro
            355                 360                 365

Ala Ala Pro Ser Asn His Met Asn Pro Val Ser Asn Gly Leu Ser Pro
        370                 375                 380

Gln Val Met Ser Ile Leu Gly Asn Pro Ser Ala Val Pro Pro Gln Pro
385                 390                 395                 400

Gln Ala Asp Phe Ser Ile Ser Pro Leu His Gly Gly Leu Asp Ser Ala
                405                 410                 415

Thr Ser Ile Ser Ala Ser Cys Ser Gln Arg Ala Asp Ser Ile Lys Pro
            420                 425                 430

Gly Asp Ser Leu Pro Thr Ser Gln Ala Tyr Cys Pro Pro Thr Tyr Ser
            435                 440                 445

Thr Thr Gly Tyr Ser Val Asp Pro Val Ala Gly Tyr Gln Tyr Gly Gln
    450                 455                 460

Tyr Gly Gln Ser Glu Cys Leu Val Pro Trp Ala Ser Pro Val Pro Ile
465                 470                 475                 480

Pro Ser Pro Thr Pro Arg Ala Ser Cys Leu Phe Met Glu Ser Tyr Lys
                485                 490                 495

Val Val Ser Gly Trp Gly Met Ser Ile Ser Gln Met Glu Lys Leu Lys
            500                 505                 510

Ser Ser Gln Met Glu Gln Phe Thr
            515                 520

<210> SEQ ID NO 4
<211> LENGTH: 520
<212> TYPE: PRT
<213> ORGANISM: Homo sapiens

<400> SEQUENCE: 4

Met Ala Ala Leu Pro Gly Thr Val Pro Arg Met Met Arg Pro Ala Pro
1               5                   10                  15

Gly Gln Asn Tyr Pro Arg Thr Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
    50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
                85                  90                  95

Arg Pro Gly Ala Ile Gly Gly Ser Lys Pro Arg Gln Val Ala Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Arg Leu Leu Lys Asp Gly His Cys Asp
    130                 135                 140

Arg Ser Thr Val Pro Ser Gly Leu Val Ser Ser Ile Ser Arg Val Leu
145                 150                 155                 160

Arg Ile Lys Phe Gly Lys Lys Glu Glu Asp Glu Ala Asp Lys Lys
                165                 170                 175

Glu Asp Asp Gly Glu Lys Lys Ala Lys His Ser Ile Asp Gly Ile Leu
            180                 185                 190

Gly Asp Lys Gly Asn Arg Leu Asp Glu Gly Ser Asp Val Glu Ser Glu
        195                 200                 205
```

```
Pro Asp Leu Pro Leu Lys Arg Lys Gln Arg Arg Ser Arg Thr Thr Phe
    210                 215                 220

Thr Ala Glu Gln Leu Glu Glu Leu Lys Ala Phe Glu Arg Thr His
225                 230                 235                 240

Tyr Pro Asp Ile Tyr Thr Arg Glu Glu Leu Ala Gln Arg Thr Lys Leu
                245                 250                 255

Thr Glu Ala Arg Val Gln Val Trp Phe Ser Asn Arg Arg Ala Arg Trp
            260                 265                 270

Arg Lys Gln Ala Gly Ala Asn Gln Leu Ala Ala Phe Asn His Leu Leu
        275                 280                 285

Pro Gly Gly Phe Pro Pro Thr Gly Met Pro Thr Leu Pro Pro Tyr Gln
    290                 295                 300

Leu Pro Asp Ser Thr Tyr Pro Thr Thr Thr Ile Ser Gln Asp Gly Gly
305                 310                 315                 320

Ser Thr Val His Arg Pro Gln Pro Leu Pro Pro Ser Thr Met His Gln
                325                 330                 335

Gly Gly Leu Ala Ala Ala Ala Ala Ala Asp Thr Ser Ser Ala Tyr
            340                 345                 350

Gly Ala Arg His Ser Phe Ser Ser Tyr Ser Asp Ser Phe Met Asn Pro
        355                 360                 365

Ala Ala Pro Ser Asn His Met Asn Pro Val Ser Asn Gly Leu Ser Pro
    370                 375                 380

Gln Val Met Ser Ile Leu Gly Asn Pro Ser Ala Val Pro Pro Gln Pro
385                 390                 395                 400

Gln Ala Asp Phe Ser Ile Ser Pro Leu His Gly Gly Leu Asp Ser Ala
                405                 410                 415

Thr Ser Ile Ser Ala Ser Cys Ser Gln Arg Ala Asp Ser Ile Lys Pro
            420                 425                 430

Gly Asp Ser Leu Pro Thr Ser Gln Ala Tyr Cys Pro Pro Thr Tyr Ser
        435                 440                 445

Thr Thr Gly Tyr Ser Val Asp Pro Val Ala Gly Tyr Gln Tyr Gly Gln
    450                 455                 460

Tyr Gly Gln Ser Glu Cys Leu Val Pro Trp Ala Ser Pro Val Pro Ile
465                 470                 475                 480

Pro Ser Pro Thr Pro Arg Ala Ser Cys Leu Phe Met Glu Ser Tyr Lys
                485                 490                 495

Val Val Ser Gly Trp Gly Met Ser Ile Ser Gln Met Glu Lys Leu Lys
            500                 505                 510

Ser Ser Gln Met Glu Gln Phe Thr
        515                 520

<210> SEQ ID NO 5
<211> LENGTH: 467
<212> TYPE: PRT
<213> ORGANISM: Homo sapiens

<400> SEQUENCE: 5

Met Ala Ala Leu Pro Gly Thr Val Pro Arg Met Met Arg Pro Ala Pro
  1               5                  10                  15

Gly Gln Asn Tyr Pro Arg Thr Gly Phe Pro Leu Glu Val Ser Thr Pro
             20                  25                  30

Leu Gly Gln Gly Arg Val Asn Gln Leu Gly Gly Val Phe Ile Asn Gly
         35                  40                  45

Arg Pro Leu Pro Asn His Ile Arg His Lys Ile Val Glu Met Ala His
```

-continued

```
            50                  55                  60
His Gly Ile Arg Pro Cys Val Ile Ser Arg Gln Leu Arg Val Ser His
 65                  70                  75                  80

Gly Cys Val Ser Lys Ile Leu Cys Arg Tyr Gln Glu Thr Gly Ser Ile
                 85                  90                  95

Arg Pro Gly Ala Ile Gly Ser Lys Pro Arg Gln Val Ala Thr Pro
                100                 105                 110

Asp Val Glu Lys Lys Ile Glu Glu Tyr Lys Arg Glu Asn Pro Gly Met
                115                 120                 125

Phe Ser Trp Glu Ile Arg Asp Arg Leu Leu Lys Asp Gly His Cys Asp
130                 135                 140

Arg Ser Thr Val Pro Ser Gly Leu Val Ser Ser Ile Ser Arg Val Leu
145                 150                 155                 160

Arg Ile Lys Phe Gly Lys Lys Glu Glu Glu Asp Glu Ala Asp Lys Lys
                165                 170                 175

Glu Asp Asp Gly Glu Lys Lys Ala Lys His Ser Ile Asp Gly Ile Leu
                180                 185                 190

Gly Asp Lys Gly Asn Arg Leu Asp Glu Gly Ser Asp Val Glu Ser Glu
    195                 200                 205

Pro Asp Leu Pro Leu Lys Arg Lys Gln Arg Arg Ser Arg Thr Thr Phe
210                 215                 220

Thr Ala Glu Gln Leu Glu Glu Leu Glu Lys Ala Phe Glu Arg Thr His
225                 230                 235                 240

Tyr Pro Asp Ile Tyr Thr Arg Glu Glu Leu Ala Gln Arg Thr Lys Leu
                245                 250                 255

Thr Glu Ala Arg Val Gln Val Trp Phe Ser Asn Arg Arg Ala Arg Trp
                260                 265                 270

Arg Lys Gln Ala Gly Ala Asn Gln Leu Ala Ala Phe Asn His Leu Leu
    275                 280                 285

Pro Gly Gly Phe Pro Pro Thr Gly Met Pro Thr Leu Pro Pro Tyr Gln
290                 295                 300

Leu Pro Asp Ser Thr Tyr Pro Thr Thr Thr Ile Ser Gln Asp Gly Gly
305                 310                 315                 320

Ser Thr Val His Arg Pro Gln Pro Leu Pro Pro Ser Thr Met His Gln
                325                 330                 335

Gly Gly Leu Ala Ala Ala Ala Ala Ala Asp Thr Ser Ser Ala Tyr
                340                 345                 350

Gly Ala Arg His Ser Phe Ser Tyr Ser Asp Ser Phe Met Asn Pro
    355                 360                 365

Ala Ala Pro Ser Asn His Met Asn Pro Val Ser Asn Gly Leu Ser Pro
370                 375                 380

Gln Val Met Ser Ile Leu Gly Asn Pro Ser Ala Val Pro Pro Gln Pro
385                 390                 395                 400

Gln Ala Asp Phe Ser Ile Ser Pro Leu His Gly Gly Leu Asp Ser Ala
                405                 410                 415

Thr Ser Ile Ser Ala Ser Cys Ser Gln Arg Ala Asp Ser Ile Lys Pro
                420                 425                 430

Gly Asp Ser Leu Pro Thr Ser Gln Ala Tyr Cys Pro Pro Thr Tyr Ser
                435                 440                 445

Thr Thr Gly Tyr Ser Val Asp Pro Val Ala Gly Tyr Gln Tyr Gly Gln
    450                 455                 460

Tyr Gly Gln
465
```

<210> SEQ ID NO 6
<211> LENGTH: 524
<212> TYPE: PRT
<213> ORGANISM: Gallus gallus

<400> SEQUENCE: 6

Met Ala Ala Leu Pro Gly Thr Val Pro Arg Met Met Arg Pro Ala Pro
1               5                   10                  15

Gly Gln Asn Tyr Pro Arg Thr Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
    50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
                85                  90                  95

Arg Pro Gly Ala Ile Gly Gly Ser Lys Pro Arg Gln Val Ala Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Arg Leu Leu Lys Asp Gly His Cys Asp
    130                 135                 140

Arg Ser Thr Val Pro Ser Val Ser Ser Ile Ser Arg Val Leu Arg Ile
145                 150                 155                 160

Lys Phe Gly Lys Lys Glu Glu Glu Asp Cys Asp Lys Lys Glu Glu
                165                 170                 175

Asp Gly Glu Lys Lys Ala Lys His Ser Ile Asp Gly Ile Leu Gly Asp
            180                 185                 190

Lys Gly Asn Arg Leu Asp Glu Gly Ser Asp Val Glu Ser Glu Pro Asp
        195                 200                 205

Leu Pro Leu Lys Arg Lys Gln Arg Arg Ser Arg Thr Thr Phe Thr Ala
    210                 215                 220

Glu Gln Leu Glu Glu Leu Glu Lys Ala Phe Glu Arg Thr His Tyr Pro
225                 230                 235                 240

Asp Ile Tyr Thr Arg Glu Glu Leu Ala Gln Arg Thr Lys Leu Thr Glu
                245                 250                 255

Ala Arg Val Gln Val Trp Phe Ser Asn Arg Arg Ala Arg Trp Arg Lys
            260                 265                 270

Gln Ala Gly Ala Asn Gln Leu Ala Ala Phe Asn His Leu Leu Pro Gly
        275                 280                 285

Gly Phe Pro Pro Thr Gly Met Pro Thr Leu Pro Pro Tyr Gln Leu Pro
    290                 295                 300

Asp Ser Thr Tyr Pro Thr Thr Thr Ile Ser Gln Asp Gly Gly Ser Thr
305                 310                 315                 320

Val His Arg Pro Gln Pro Leu Pro Pro Ser Thr Met His Gln Gly Gly
                325                 330                 335

Leu Ala Ala Ala Ala Ala Asp Ser Ser Ala Tyr Gly Ala Arg
            340                 345                 350

His Ser Phe Ser Ser Tyr Ser Asp Ser Phe Met Asn Ala Ala Pro
        355                 360                 365

Ala Asn His Met Asn Pro Val Ser Asn Gly Leu Ser Pro Gln Lys Gln

```
                370                 375                 380
Gly Ala Gln Asn Lys Met Gln Cys Ser Arg Trp Asn Leu Thr Ile Ala
385                 390                 395                 400

Leu Asn Asn Gln Val Met Ser Ile Leu Ser Asn Pro Ser Gly Val Pro
                405                 410                 415

Pro Gln Pro Gln Ala Asp Phe Ser Ile Ser Pro Leu His Gly Gly Leu
            420                 425                 430

Asp Thr Thr Asn Ser Ile Ser Ala Ser Cys Ser Gln Arg Ser Asp Ser
                435                 440                 445

Ile Lys Ser Val Asp Ser Leu Pro Thr Ser Gln Ser Tyr Cys Pro Pro
        450                 455                 460

Thr Tyr Ser Thr Thr Ser Tyr Ser Val Asp Pro Val Ala Gly Tyr Gln
465                 470                 475                 480

Tyr Gly Gln Tyr Gly Gln Thr Ala Val Asp Tyr Leu Thr Lys Asn Val
                485                 490                 495

Ser Leu Ser Thr Gln Arg Arg Met Lys Leu Gly Glu His Ser Ala Val
                500                 505                 510

Leu Gly Leu Leu Pro Val Glu Thr Gly Gln Ala Tyr
            515                 520

<210> SEQ ID NO 7
<211> LENGTH: 479
<212> TYPE: PRT
<213> ORGANISM: Homo sapiens

<400> SEQUENCE: 7

Met Thr Thr Leu Ala Gly Ala Val Pro Arg Met Met Arg Pro Gly Pro
1               5                   10                  15

Gly Gln Asn Tyr Pro Arg Ser Gly Phe Pro Leu Glu Val Ser Thr Pro
                20                  25                  30

Leu Gly Gln Gly Arg Val Asn Gln Leu Gly Gly Val Phe Ile Asn Gly
            35                  40                  45

Arg Pro Leu Pro Asn His Ile Arg His Lys Ile Val Glu Met Ala His
50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
                85                  90                  95

Arg Pro Gly Ala Ile Gly Gly Ser Lys Pro Lys Gln Val Thr Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Lys Leu Leu Lys Asp Ala Val Cys Asp
130                 135                 140

Arg Asn Thr Val Pro Ser Val Ser Ser Ile Ser Arg Ile Leu Arg Ser
145                 150                 155                 160

Lys Phe Gly Lys Gly Glu Glu Glu Glu Ala Asp Leu Glu Arg Lys Glu
                165                 170                 175

Ala Glu Glu Ser Glu Lys Lys Ala Lys His Ser Ile Asp Gly Ile Leu
            180                 185                 190

Ser Glu Arg Ala Ser Ala Pro Gln Ser Asp Glu Gly Ser Asp Ile Asp
        195                 200                 205

Ser Glu Pro Asp Leu Pro Leu Lys Arg Lys Gln Arg Arg Ser Arg Thr
210                 215                 220
```

-continued

```
Thr Phe Thr Ala Glu Gln Leu Glu Glu Leu Glu Arg Ala Phe Glu Arg
225                 230                 235                 240

Thr His Tyr Pro Asp Ile Tyr Thr Arg Glu Glu Leu Ala Gln Arg Ala
            245                 250                 255

Lys Leu Thr Glu Ala Arg Val Gln Val Trp Phe Ser Asn Arg Arg Ala
        260                 265                 270

Arg Trp Arg Lys Gln Ala Gly Ala Asn Gln Leu Met Ala Phe Asn His
    275                 280                 285

Leu Ile Pro Gly Gly Phe Pro Pro Thr Ala Met Pro Thr Leu Pro Thr
290                 295                 300

Tyr Gln Leu Ser Glu Thr Ser Tyr Gln Pro Thr Ser Ile Pro Gln Ala
305                 310                 315                 320

Val Ser Asp Pro Ser Ser Thr Val His Arg Pro Gln Pro Leu Pro Pro
            325                 330                 335

Ser Thr Val His Gln Ser Thr Ile Pro Ser Asn Pro Asp Ser Ser Ser
        340                 345                 350

Ala Tyr Cys Leu Pro Ser Thr Arg His Gly Phe Ser Ser Tyr Thr Asp
    355                 360                 365

Ser Phe Val Pro Pro Ser Gly Pro Ser Asn Pro Met Asn Pro Thr Ile
370                 375                 380

Gly Asn Gly Leu Ser Pro Gln Val Met Gly Leu Leu Thr Asn His Gly
385                 390                 395                 400

Gly Val Pro His Gln Pro Gln Thr Asp Tyr Ala Leu Ser Pro Leu Thr
            405                 410                 415

Gly Gly Leu Glu Pro Thr Thr Thr Val Ser Ala Ser Cys Ser Gln Arg
        420                 425                 430

Leu Asp His Met Lys Ser Leu Asp Ser Leu Pro Thr Ser Gln Ser Tyr
    435                 440                 445

Cys Pro Pro Thr Tyr Ser Thr Thr Gly Tyr Ser Met Asp Pro Val Thr
450                 455                 460

Gly Tyr Gln Tyr Gly Gln Tyr Gly Gln Ser Lys Pro Trp Thr Phe
465                 470                 475

<210> SEQ ID NO 8
<211> LENGTH: 215
<212> TYPE: PRT
<213> ORGANISM: Homo sapiens

<400> SEQUENCE: 8

Met Thr Thr Leu Ala Gly Ala Val Pro Arg Met Met Arg Pro Gly Pro
1               5                   10                  15

Gly Gln Asn Tyr Pro Arg Ser Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
    50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
            85                  90                  95

Arg Pro Gly Ala Ile Gly Gly Ser Lys Pro Lys Gln Val Thr Thr Pro
        100                 105                 110

Asp Val Glu Lys Lys Ile Glu Glu Tyr Lys Arg Glu Asn Pro Gly Met
    115                 120                 125
```

```
Phe Ser Trp Glu Ile Arg Asp Lys Leu Leu Lys Asp Ala Val Cys Asp
            130                 135                 140

Arg Asn Thr Val Pro Ser Val Ser Ser Ile Ser Arg Ile Leu Arg Ser
145                 150                 155                 160

Lys Phe Gly Lys Gly Glu Glu Glu Glu Ala Asp Leu Glu Arg Lys Glu
                165                 170                 175

Ala Glu Glu Ser Glu Lys Lys Ala Lys His Ser Ile Asp Gly Ile Leu
            180                 185                 190

Ser Glu Arg Gly Lys Arg Trp Arg Leu Gly Arg Arg Thr Cys Trp Val
        195                 200                 205

Thr Trp Arg Ala Ser Ala Ser
    210                 215

<210> SEQ ID NO 9
<211> LENGTH: 206
<212> TYPE: PRT
<213> ORGANISM: Homo sapiens

<400> SEQUENCE: 9

Met Thr Thr Leu Ala Gly Ala Val Pro Arg Met Met Arg Pro Gly Pro
1               5                   10                  15

Gly Gln Asn Tyr Pro Arg Ser Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
                85                  90                  95

Arg Pro Gly Ala Ile Gly Gly Ser Lys Pro Lys Gln Val Thr Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Lys Leu Leu Lys Asp Ala Val Cys Asp
            130                 135                 140

Arg Asn Thr Val Pro Ser Val Ser Ser Ile Ser Arg Ile Leu Arg Ser
145                 150                 155                 160

Lys Phe Gly Lys Gly Glu Glu Glu Glu Ala Asp Leu Glu Arg Lys Glu
                165                 170                 175

Ala Glu Glu Ser Glu Lys Lys Ala Lys His Ser Ile Asp Gly Ile Leu
            180                 185                 190

Ser Glu Arg Gly Lys Ala Leu Val Ser Gly Val Ser Ser His
        195                 200                 205

<210> SEQ ID NO 10
<211> LENGTH: 332
<212> TYPE: PRT
<213> ORGANISM: Homo sapiens

<400> SEQUENCE: 10

Pro Ser Val Ser Ser Ile Ser Arg Ile Leu Arg Ser Lys Phe Gly Lys
1               5                   10                  15

Gly Glu Glu Glu Glu Ala Asp Leu Glu Arg Lys Glu Ala Glu Glu Ser
            20                  25                  30
```

Glu Lys Lys Ala Lys His Ser Ile Asp Gly Ile Leu Ser Glu Arg Ala
            35                  40                  45

Ser Ala Pro Gln Ser Asp Glu Gly Ser Asp Ile Asp Ser Glu Pro Asp
        50                  55                  60

Leu Pro Leu Lys Arg Lys Gln Arg Arg Ser Arg Thr Thr Phe Thr Ala
65                  70                  75                  80

Glu Gln Leu Glu Glu Leu Glu His Val Ala Phe Glu Arg Thr His Tyr
                85                  90                  95

Pro Asp Ile Tyr Thr Arg Glu Glu Leu Ala Gln Arg Ala Lys Leu Thr
            100                 105                 110

Glu Ala Arg Val Gln Val Trp Phe Ser Asn Arg Arg Ala Arg Trp Arg
        115                 120                 125

Lys Gln Ala Gly Ala Asn Gln Leu Met Ala Phe Asn His Leu Ile Pro
    130                 135                 140

Gly Gly Phe Pro Pro Thr Ala Met Pro Thr Leu Pro Thr Tyr Gln Leu
145                 150                 155                 160

Ser Glu His Ser Tyr Gln Pro Thr Ser Ile Pro Gln Ala Val Ser Asp
                165                 170                 175

Pro Ser Ser Thr Val His Arg Pro Gln Pro Leu Pro Pro Ser Thr Val
            180                 185                 190

His Gln Ser Thr Ile Pro Ser Asn Pro Asp Ser Ser Ala Tyr Cys
        195                 200                 205

Leu Pro Ser Thr Arg His Gly Phe Ser Ser Tyr Thr Asp Ser Phe Val
    210                 215                 220

Pro Pro Ser Gly Pro Ser Asn Pro Met Asn Pro Thr Ile Gly Asn Gly
225                 230                 235                 240

Leu Ser Pro Gln Val Met Gly Leu Leu Thr Asn His Gly Gly Val Pro
                245                 250                 255

His Gln Pro Gln Thr Asp Tyr Ala Leu Ser Pro Leu Thr Gly Gly Leu
            260                 265                 270

Glu Pro Thr Thr Thr Val Ser Ala Ser Cys Ser Gln Arg Leu Asp His
        275                 280                 285

Met Lys Ser Leu Asp Ser Leu Pro Thr Ser Gln Ser Tyr Cys Pro Pro
    290                 295                 300

Thr Tyr Ser Thr Thr Gly Tyr Ser Met Asp Pro Val Thr Gly Tyr Gln
305                 310                 315                 320

Tyr Gly Gln Tyr Gly Gln Ser Lys Pro Trp Thr Phe
                325                 330

<210> SEQ ID NO 11
<211> LENGTH: 479
<212> TYPE: PRT
<213> ORGANISM: Mus musculus

<400> SEQUENCE: 11

Met Thr Thr Leu Ala Gly Ala Val Pro Arg Met Met Arg Pro Gly Pro
1               5                   10                  15

Gly Gln Asn Tyr Pro Arg Ser Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
    50                  55                  60

His Gly Ile Arg Pro Cys Val Ile Ser Arg Gln Leu Arg Val Ser His

```
                65                  70                  75                  80
Gly Cys Val Ser Lys Ile Leu Cys Arg Tyr Gln Glu Thr Gly Ser Ile
                    85                  90                  95
Arg Pro Gly Ala Ile Gly Ser Lys Pro Lys Gln Val Thr Thr Pro
                100                 105                 110
Asp Val Glu Lys Lys Ile Glu Glu Tyr Lys Arg Glu Asn Pro Gly Met
                115                 120                 125
Phe Ser Trp Glu Ile Arg Asp Lys Leu Leu Lys Asp Ala Val Cys Asp
    130                 135                 140
Arg Asn Thr Val Pro Ser Val Ser Ser Ile Ser Arg Ile Leu Arg Ser
145                 150                 155                 160
Lys Phe Gly Lys Gly Glu Glu Glu Ala Asp Leu Glu Arg Lys Glu
                165                 170                 175
Ala Glu Glu Ser Glu Lys Lys Ala Lys His Ser Ile Asp Gly Ile Leu
                180                 185                 190
Ser Glu Arg Ala Ser Ala Pro Gln Ser Asp Glu Gly Ser Asp Ile Asp
                195                 200                 205
Ser Glu Pro Asp Leu Pro Leu Lys Arg Lys Gln Arg Arg Ser Arg Thr
    210                 215                 220
Thr Phe Thr Ala Glu Gln Leu Glu Glu Leu Glu Arg Ala Phe Glu Arg
225                 230                 235                 240
Thr His Tyr Pro Asp Ile Tyr Thr Arg Glu Glu Leu Ala Gln Arg Ala
                245                 250                 255
Lys Leu Thr Glu Ala Arg Val Gln Val Trp Phe Ser Asn Arg Arg Ala
                260                 265                 270
Arg Trp Arg Lys Gln Ala Gly Ala Asn Gln Leu Met Ala Phe Asn His
    275                 280                 285
Leu Ile Pro Gly Gly Phe Pro Pro Thr Ala Met Pro Thr Leu Pro Thr
    290                 295                 300
Tyr Gln Leu Ser Glu His Ser Tyr Gln Pro Thr Ser Ile Pro Gln Ala
305                 310                 315                 320
Val Ser Asp Pro Ser Ser Thr Val His Arg Pro Gln Pro Leu Pro Pro
                325                 330                 335
Ser Thr Val His Gln Ser Thr Ile Pro Ser Asn Ala Asp Ser Ser Ser
                340                 345                 350
Ala Tyr Cys Leu Pro Ser Thr Arg His Gly Phe Ser Ser Tyr Thr Asp
                355                 360                 365
Ser Phe Val Pro Pro Ser Gly Pro Ser Asn Pro Met Asn Pro Thr Ile
    370                 375                 380
Gly Asn Gly Leu Ser Pro Gln Val Met Gly Leu Leu Thr Asn His Gly
385                 390                 395                 400
Gly Val Pro His Gln Pro Gln Thr Asp Tyr Ala Leu Ser Pro Leu Thr
                405                 410                 415
Gly Gly Leu Glu Pro Thr Thr Val Ser Ala Ser Cys Ser Gln Arg
                420                 425                 430
Leu Glu His Met Lys Asn Val Asp Ser Leu Pro Thr Ser Gln Pro Tyr
    435                 440                 445
Cys Pro Pro Thr Tyr Ser Thr Ala Gly Tyr Ser Met Asp Pro Val Thr
    450                 455                 460
Gly Tyr Gln Tyr Gly Gln Tyr Gly Gln Ser Lys Pro Trp Thr Phe
465                 470                 475

<210> SEQ ID NO 12
```

```
<211> LENGTH: 129
<212> TYPE: PRT
<213> ORGANISM: Gallus gallus

<400> SEQUENCE: 12

Gly Gln Gly Arg Val Asn Gln Leu Gly Gly Val Phe Ile Asn Gly Arg
 1               5                  10                  15

Pro Leu Pro Asn His Ile Arg His Lys Ile Val Gln Met Ala His His
            20                  25                  30

Gly Ile Arg Pro Cys Val Ile Ser Arg Gln Leu Arg Val Ser His Gly
        35                  40                  45

Cys Val Ser Lys Ile Leu Cys Arg Tyr Gln Glu Thr Gly Ser Ile Arg
 50                  55                  60

Pro Gly Ala Ile Gly Gly Ser Lys Pro Lys Gln Val Thr Thr Pro Asp
65                  70                  75                  80

Val Glu Lys Lys Ile Glu Glu Tyr Lys Arg Glu Asn Ala Gly Met Phe
                85                  90                  95

Ser Trp Glu Ile Arg Asp Arg Leu Leu Lys Asp Gly Val Cys Asp Arg
            100                 105                 110

Asn Thr Val Pro Ser Val Ser Ser Ile Ser Leu Ile Leu Arg Ser Lys
        115                 120                 125

Phe

<210> SEQ ID NO 13
<211> LENGTH: 4387
<212> TYPE: DNA
<213> ORGANISM: Mus musculus
<220> FEATURE:
<221> NAME/KEY: CDS
<222> LOCATION: (102)...(1613)

<400> SEQUENCE: 13
actcactata gggcaagcag tggtaacaac gcagagtacg cgggagagac gccaagaggt      60
ttatccagcg gactctggat tcgtctccag cgtgtgcaga a atg gcg gcg ctg ccc    116
                                             Met Ala Ala Leu Pro
                                              1               5 ggc gcg gtc ccc agg atg atg aga ccc ggc ccg ggg cag aac tac ccg      164
Gly Ala Val Pro Arg Met Met Arg Pro Gly Pro Gly Gln Asn Tyr Pro
            10                  15                  20 cgc acc ggc ttc ccc ctg gaa gtg tcc acc cct ctt ggc caa ggc cgg      212
Arg Thr Gly Phe Pro Leu Glu Val Ser Thr Pro Leu Gly Gln Gly Arg
        25                  30                  35 gtc aat cag ctt ggt ggg gtc ttc atc aat ggt cga ccc ctg ccg aac      260
Val Asn Gln Leu Gly Gly Val Phe Ile Asn Gly Arg Pro Leu Pro Asn
    40                  45                  50 cac atc cgt cac aag ata gtg gaa atg gcc cac cat ggc atc cgg ccc      308
His Ile Arg His Lys Ile Val Glu Met Ala His His Gly Ile Arg Pro
55                  60                  65 tgc gtc atc tcc cgt cag ctc cgt gtt tct cat ggt tgt gtc tcc aag      356
Cys Val Ile Ser Arg Gln Leu Arg Val Ser His Gly Cys Val Ser Lys
                75                  80                  85 att ctg tgc cga tat cag gag act ggg tcc atc cgg ccc ggg gct atc      404
Ile Leu Cys Arg Tyr Gln Glu Thr Gly Ser Ile Arg Pro Gly Ala Ile
            90                  95                 100 gga ggc agc aag ccc aga cag gtg gcg act ccg gat gtg gag aaa aag      452
Gly Gly Ser Lys Pro Arg Gln Val Ala Thr Pro Asp Val Glu Lys Lys
        105                 110                 115 att gag gag tat aag aga gag aac ccc ggg atg ttc agc tgg gaa atc      500
Ile Glu Glu Tyr Lys Arg Glu Asn Pro Gly Met Phe Ser Trp Glu Ile
```

-continued

```
              120                 125                 130
cgg gac cgg ctg ctg aag gac ggt cac tgc gac cga agc acg gtg ccc      548
Arg Asp Arg Leu Leu Lys Asp Gly His Cys Asp Arg Ser Thr Val Pro
        135                 140                 145 tca gtg agt tcg att agc cga gtg ctc aga atc aag ttc ggg aag aaa      596
Ser Val Ser Ser Ile Ser Arg Val Leu Arg Ile Lys Phe Gly Lys Lys
150                 155                 160                 165 gag gac gac gag gaa gga gac aag aaa gaa gaa gat ggc gag aag aaa      644
Glu Asp Asp Glu Glu Gly Asp Lys Lys Glu Glu Asp Gly Glu Lys Lys
                170                 175                 180 gcc aaa cac agc atc gat ggc atc ctg ggc gac aaa ggg aac cgt ctg      692
Ala Lys His Ser Ile Asp Gly Ile Leu Gly Asp Lys Gly Asn Arg Leu
            185                 190                 195 gat gag ggc tca gat gtg gaa tca gaa ccc gac ctc ccc ctg aag cgc      740
Asp Glu Gly Ser Asp Val Glu Ser Glu Pro Asp Leu Pro Leu Lys Arg
        200                 205                 210 aag cag cgc cgc agt cgg acc acg ttc aca gcc gag cag ctg gag gag      788
Lys Gln Arg Arg Ser Arg Thr Thr Phe Thr Ala Glu Gln Leu Glu Glu
    215                 220                 225 cta gag aag gcc ttt gag agg acc cac tac ccg gac atc tac acc cgg      836
Leu Glu Lys Ala Phe Glu Arg Thr His Tyr Pro Asp Ile Tyr Thr Arg
230                 235                 240                 245 gag gag ctg gca cag agg acc aag ctc acg gag gca cgc gtc cag gtc      884
Glu Glu Leu Ala Gln Arg Thr Lys Leu Thr Glu Ala Arg Val Gln Val
                250                 255                 260 tgg ttc agt aac cgg cgt gcc cgc tgg cgc aag cag gca gga gct aac      932
Trp Phe Ser Asn Arg Arg Ala Arg Trp Arg Lys Gln Ala Gly Ala Asn
            265                 270                 275 cag ctg gcc gcc ttc aac cac ctt ctg ccg gga ggt ttc cca ccc acc      980
Gln Leu Ala Ala Phe Asn His Leu Leu Pro Gly Gly Phe Pro Pro Thr
        280                 285                 290 ggc atg ccc acg ctg cca ccc tac cag ctg ccg gac tct acc tac ccc     1028
Gly Met Pro Thr Leu Pro Pro Tyr Gln Leu Pro Asp Ser Thr Tyr Pro
    295                 300                 305 acc acc acc atc tcc caa gat ggg ggc agc aca gta cac agg ccc cag     1076
Thr Thr Thr Ile Ser Gln Asp Gly Gly Ser Thr Val His Arg Pro Gln
310                 315                 320                 325 ccc ctt ccg cca tca acc atg cat cag ggt ggg ctg gct gcg gcc gct     1124
Pro Leu Pro Pro Ser Thr Met His Gln Gly Gly Leu Ala Ala Ala Ala
                330                 335                 340 gca gca gca gac acc agc tct gcc tac gga gcc cgc cac agc ttc tcc     1172
Ala Ala Ala Asp Thr Ser Ser Ala Tyr Gly Ala Arg His Ser Phe Ser
            345                 350                 355 agc tac tct gac agc ttc atg aac cct ggg gct ccc tcc aac cac atg     1220
Ser Tyr Ser Asp Ser Phe Met Asn Pro Gly Ala Pro Ser Asn His Met
        360                 365                 370 aac cct gtc agc aat ggc ctg tct cct cag gtc atg agc atc ctt agc     1268
Asn Pro Val Ser Asn Gly Leu Ser Pro Gln Val Met Ser Ile Leu Ser
    375                 380                 385 aac ccg agt gcc gtg cct cca cag ccc cag gcc gac ttc tcc atc tcc     1316
Asn Pro Ser Ala Val Pro Pro Gln Pro Gln Ala Asp Phe Ser Ile Ser
390                 395                 400                 405 ccg ctg cat gga ggc ctg gac tcg gct tcc tcc atc tca gcc agc tgc     1364
Pro Leu His Gly Gly Leu Asp Ser Ala Ser Ser Ile Ser Ala Ser Cys
                410                 415                 420 agc caa cgg gcc gac tcc atc aag cca gga gac agc ttg ccc acg tcc     1412
Ser Gln Arg Ala Asp Ser Ile Lys Pro Gly Asp Ser Leu Pro Thr Ser
            425                 430                 435 cag tct tac tgc cca ccc acc tac agc acc act ggc tac agt gtg gac     1460
Gln Ser Tyr Cys Pro Pro Thr Tyr Ser Thr Thr Gly Tyr Ser Val Asp
```

```
                                             -continued
Gln Ser Tyr Cys Pro Pro Thr Tyr Ser Thr Thr Gly Tyr Ser Val Asp
        440                 445                 450 cct gtg gct ggc tac cag tac agc cag tat ggc caa act gct gtt gat      1508
Pro Val Ala Gly Tyr Gln Tyr Ser Gln Tyr Gly Gln Thr Ala Val Asp
    455                 460                 465 tac ctg gcc aaa aac gtg agc ctg tcc aca cag cgc cgt atg aag ctt      1556
Tyr Leu Ala Lys Asn Val Ser Leu Ser Thr Gln Arg Arg Met Lys Leu
470                 475                 480                 485 ggg gaa cac tcc gct gtg ctg gga ctt ctt cct gtg gaa acg gga caa      1604
Gly Glu His Ser Ala Val Leu Gly Leu Leu Pro Val Glu Thr Gly Gln
                490                 495                 500 gcc tac tag ggtccctggg caacttgcc ccatccagtg gcccagccaa               1653
Ala Tyr  * cccttcccaa gccctgagtc tcctcacctc agtcccctca tccctctggg gttgcaggag    1713
gccaagggaa aaaaacccett tcccttccta caggaaaccc tctggagacg gaaaaccagt   1773
```

```
gtgccatcta cccatgctta gtgacccaga gtgaccccct gccttcccct ctttctccag    1833
aggggttcct aggcatcctg cagtgacctc cagctcacat ccaccttctc tgtgtcgtgg    1893
cctcggtcct gtcttcagtg cagagattga ggctcaattt gaaccaagca cctagttatc    1953
agaagaaaat ggtgccaaag acaaggccct ggagtccttg acctctgagt cgtgggtgcc    2013
ctggctatgg gtgtaggtgg agcccatggg tgtcctcagt cacagagctg ggagctctct    2073
ctcgctcgct tggcatcagg actgcagcct cttccactgg acactgagat gagtccccag    2133
ggtgttccca ggggagaaag caggtaacat cccagcttta cctaggaatc cagaggactt    2193
tgggactgtc ccaatgcacc ctgcagggca tcaggagacc aggaagggat tctagcagag    2253
ggtaggggc acagaggcag agctgattgg ccatgggcta tcccagaatg cctggtcctg     2313
aatctagcat caggaggtgc aggactccta ggctgcaatc tgacagaggc ttgcccactg    2373
tgtcaggcct gggcagccca cagaacctgt cactctcctc aattggtagg agaagaggtc    2433
ttgaggtgac aggaggcagc aggcaggctc agacagtcag agagcaccaa gttttcaagt    2493
ccgcacccct ggggttcggc ataccatctt gctggcagct ggaaacctgg ttccctgaaa    2553
gggggcctcc atcctccaga atgtaaggct cttgatgcca ccggatgcag agagccttct    2613
cgggccagac aaaattgctg ctccacccca gagaagatgt tccagccttc ttggcatctc    2673
ggaggaaggc catgtcgctg tccttttcag agtagcgtat ttttcagtga tggctgctca    2733
gtcaggaggc ttctgtcgcc ttacaaagca cagtgcgctc tgggcactgt ttctaagcca    2793
ccccatccca ccccaccccc cgccaccccg gggacagagg aagatgctaa aagtcccagc    2853
aaagaggaca aagcaccttt cttaagcact ccagagtctt ccttgtaccc cgccctctct    2913
tagagctggg tcttttgagg gaaacggatt gctgagccct ccccccaat cctctcctct     2973
gtggagctgt ttatcatcct ctatttatca aaatcgcatc catctttacc ctctccttca   3033
ctatagccta cttctggatc accctcatcc agtgctggta ccccacagca ctaaatccag    3093
gaaccctggg cttgatcacc tgttgccacc tgtacacatg aaaccacctg ctggcccggc    3153
ccatgtctcc tgccctcagc cagcaagaca ttcctagaga gaggaactat gggctcaaaa    3213
gccccaactg acttccttttt gcctggggac ctgaaccgac aagacaccag ggacacttgt   3273
ctacatgaac atgtgaccaa tgtacaccga tttctcatct ctagacctat tatctgaagc    3333
ctgtcccggg ccatgactag aatggcttgt atctgtggtt tagagaagtc taataataac    3393
tgagggcaaa ctgactctct ggtagcatgg agcaccaggc ggatgagct caccagctct     3453
gtccaggttt caaaggagga gactgttggg ctcttcaagg tctggacaag aggaaagcca    3513
```

```
cattgccccc ttgggaaccc aggttctcct tttgaacttc tcacagctgc aagcacccct    3573
ttcaaagacc aaatgcatcc tcctccacat tccttgctcc ctggaggcct ggctctggat    3633
acacctgagt cttcgttcac ctactacact ttaggagcag gaacttcaag caggtgacat    3693
ccacagggcc cagtcccagc caagggagca acattccaac gcttggacca atcataatga    3753
tctgcccgtg agggtaaccg caactagaga cctgcttggg agaaaacaaa atgacttctc    3813
attccatgcc atgcctctga acgctccccc aagctgccat cttggtataa aatgggactt    3873
gtgttgtggg ggaccccttg accccaacag gttttcccaa ctgtctcatg cttttgtgaa    3933
tctgtctgct ttgatctgta aaactcagcc ttgtttgggc agcttgtaat ttcaacagtg    3993
aggcgacatc gattagatga gaggcaccag gcctctccgc cgccgtccct ctgtggccgt    4053
ccctctgtgg ccgtccctct gtggccgtcc ctctgtggcc gtccctctgt ggccgtccct    4113
ctggggttga gcagaaccta gaagaaggcc gatttccagt ggccagactg gaccagaaac    4173
agcccccacc ccaatccctg taaatagagt caatagcaaa ataagagggg cgccctccat    4233
gtcacctcaa gtagctactg gttcttccgt ggaggcccct ctgaactcat tgtctggtag    4293
ttgaaaatgt gatgttgtgc tgtttgttta tagaacattg gcttttata tataaatcta    4353 tatacttaaa aacaaaaacc cgctggttcc ctga                                4387
```